(12) United States Patent
Sugawara et al.

(10) Patent No.: US 6,319,902 B1
(45) Date of Patent: *Nov. 20, 2001

(54) PEPTIDE DERIVATIVES HAVING THIAZOLYL-ALANINE RESIDUE

(75) Inventors: Tamio Sugawara; Takayoshi Yoshikawa, both of Hyogo; Yukio Tada, Osaka, all of (JP)

(73) Assignee: Shionogi & Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/230,821

(22) PCT Filed: Aug. 22, 1997

(86) PCT No.: PCT/JP97/02917

§ 371 Date: May 12, 1999

§ 102(e) Date: May 12, 1999

(87) PCT Pub. No.: WO98/08867

PCT Pub. Date: Mar. 5, 1998

(51) Int. Cl.$^7$ ..................................... C07K 5/06
(52) U.S. Cl. .............................. 514/19; 548/535; 562/553
(58) Field of Search .............................. 514/19; 548/535; 562/553

(56) References Cited

FOREIGN PATENT DOCUMENTS 96 11209    4/1996  (WO) .

OTHER PUBLICATIONS

Abstract of JP–116466, 1977.*
Abstract of JP–62–234029, 1987.*
Abstract of JP–3–236397, 1991.*
M. Miyamoto et al, Eur. J. Pharmacol. (1994) vol. 271, p. 357–366.

* cited by examiner

Primary Examiner—Christopher S. F. Low
Assistant Examiner—David Lukton
(74) Attorney, Agent, or Firm—Birch, Stewart, Kolasch & Birch, LLP

(57) ABSTRACT

A peptide derivation of the formula (I) or its pharmaceutically acceptable salt or hydrate thereof is disclosed.

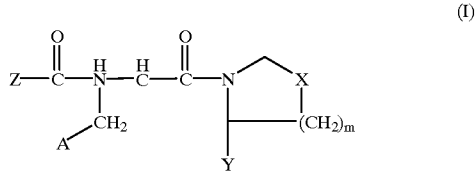

These compounds have superior ability over thyroid stimulating hormone (TRH) and its derivatives to activate the central nervous system, such as, for example, sustained acetylcholine releasing action, anti-reserpine action and locomotor increment.

14 Claims, 2 Drawing Sheets

The transition of the blood glucose level by intravenous injection to rats

PEPTIDE DERIVATIVES HAVING THIAZOLYL-ALANINE RESIDUE

This application is the national phase under 35 U.S.C. §371 of PCT International Application No. PCT/JP97/02917 which has an International filing date of Aug. 22, 1997 which designated the United States of America.

1. Technical Field

This invention relates to a new peptide derivative having the residue of 3-(4-thiazolyl or 5-thiazolyl)-alanine and having an effect of activating the central nervous system. The compound of this invention is useful as a medicament.

2. Background Art

The compound of this invention is derived from L-pyroglutamyl-L-histidyl-L-prolineamide (p-Glu-His-Pro-NH$_2$), known as TRH (thyrotropin releasing hormone) isolated from hypothalamus.

TRH is a hormone consisting of 3 amino acid residues isolated from hypothalamus, and seems to show the activities through a TRH receptor. It is known not only to promote the secretion of TSH (thyroid stimulating hormone) and prolactin, but also to have the following activity; brain nervous system activation such as motor stimulating activity etc., sympathetic activity such as blood pressure elevation, respiratory stimulation, etc., spinal activity such as spinal motor nerve stimulation etc., central nervous activity such as antidepression etc., and peripheral activity such as gastrin secretion suppression, glucagon secretion stimulation, etc. Because TRH has such various activity, it has been investigated on the clinical use, and is being used as an intravenous injection for treating spinocerebellar degeneration for purposes of improvement of motility disturbance and cognitive disturbance accompanied by brain functional disturbance (Sofue, Kanazawa, Ogawa, "Neuropeptide"'91, Medicalreview).

However, there are various problems barring the clinical application of TRH. Typical ones are described below:

1) TRH shows very short half-time in blood and is required to be administered frequently, because it is digested by enzymes such as pyroglutamyl peptidase, TRH amidase, etc. in a living body.

2) Excessive secretion of TSH is caused by repeated administration of TRH due to the activity of stimulating secretion of TSH.

3) A slight mount of TRH is transferred into brain by peripheral administration because of its low hydrophobicity.

In order to solve the above problems concerning TRH, the development of TRH derivatives which have more potent activity than TRH in view of activation of the central nervous system (for example, awaking stimulation, anti-reserpine activity (hyperthermia), locomotor increment, spinal reflex increase, dopamine action potentiation, anti-anesthetic action, etc.) and have long duration of action has been attempted. Such compounds reported at the present time are illustrated below.

For example, 1-methyl-L-4,5-dihydroorotyl-L-hystidlyl-L-prolineamide (JP-B 2-36574), 2,3,4,5-tetrahydro-2-oxo-L-5-furancarbonyl-L-histidyl-L,-prolineamide (JP-A 52-116465), (1S, 2R)-2-methyl-4-oxocyclolentylcarbonyl-L-histidyl-L-prolineamide (JP-B-3-236397), orotyl-L-histydyl-L-prolineamide (JP-B 59-36612), TRH-SR (Eur. J. Pharmacol., 271, 357 (1994)), etc. are known However, the above TRH derivatives do not have enough continuous action. Additionally, intravenous injection of these compounds makes it difficult to improve the compliance to the periodical administration of them and QOL (Quality of Life) of patients having the motor disturbance.

DISCLOSURE OF INVENTION

In the above situation, the inventors of the present invention found the compounds having superior activity known TRH and its derivatives in view of the activation of the central nervous system, for example, sustained acetylcholine releasing action, anti-reserpine action and locomotor increment activity. The present invention relates to a) A peptide derivative of the formula (I):

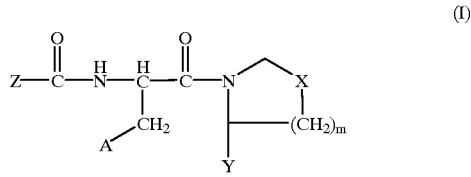

wherein A is 4-thiazolyl or 5-thiazolyl wherein the nitrogen in the thiazolyl ring may be quarternary nitrogen which is formed with optionally substituted alkyl or alkenyl, X is a bond, oxygen, or sulfur, m is an integer of 0 to 4, Y is optionally substituted alkyl, optionally substituted carboxy, cyano, or the substituent represented by the formula:

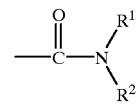

wherein $R^1$ and $R^2$ are independently hydrogen or optionally substituted alkyl, or $R^1$ and $R^2$ taken together with may form a non-aromatic heterocyclic ring the adjacent nitrogen which may contain oxygen, nitrogen, or sulfur and may be substituted, Z is the substituent represented by the formula:

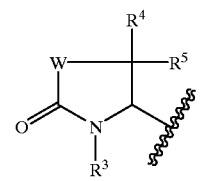

wherein $R^3$ is hydrogen, optionally substituted alkyl, optionally substituted carboxy, or optionally substituted acyl, $R^4$ and $R^5$ are each independently hydrogen or optionally substituted alkyl, and W is —(CH$_2$)n— wherein n is 0, 1, 2, or 3, oxygen, sulfur, or optionally substituted imino, or the substituent, represented by the formula:

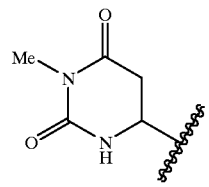

its pharmaceutically acceptable salt, or hydrate thereof.

b) A peptide derivative of the formula (II):

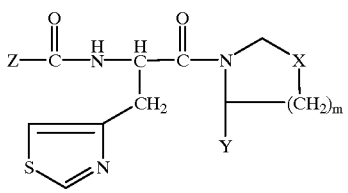

(II)

wherein X, Y, Z, and m are as defined above, and the nitrogen in the thiazolyl ring may be quarternary nitrogen which is formed with optionally substituted alkyl or alkenyl, its pharmaceutically acceptable salt, or hydrate thereof.

c) A peptide derivative of the formula (III):

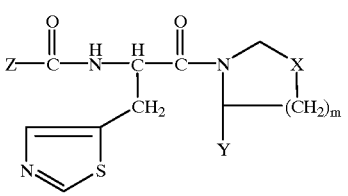

(III)

wherein X, Y, Z, and m are as defined above, and the nitrogen in the thiazolyl ring may be quarternary nitrogen which is formed with optionally substituted alkyl or alkenyl, its pharmaceutically acceptable salt, or hydrate thereof.

d) A peptide derivative of the formula (IV):

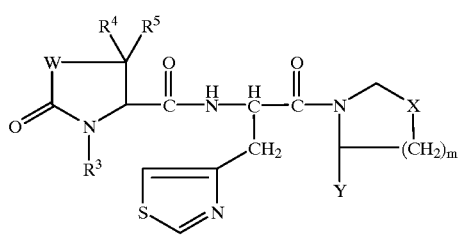

(IV)

wherein W, X, Y, m, $R^3$, $R^4$, and $R^5$ are as defined above, its pharmaceutically acceptable salt, or hydrate thereof.

e) A peptide derivative of the formula (V):

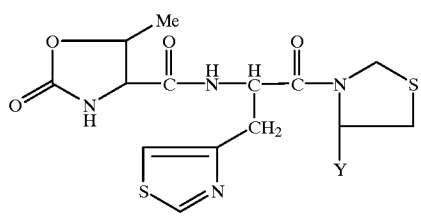

(V)

wherein Y is as defined above, its pharmaceutically acceptable salt, or hydrate thereof.

f) A peptide derivative of the formula (VI):

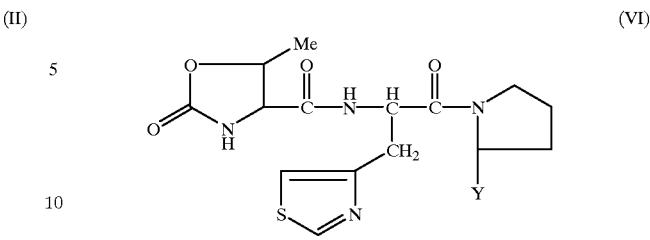

(VI)

wherein Y is as defined above, its pharmaceutically acceptable salt, or hydrate thereof.

g) A peptide derivative of any one of a) to d) wherein m is 1 or 2, provided that X is not a bond when m is 1, its pharmaceutically acceptable salt, or hydrate thereof.

h) A peptide derivative of any one of a) to d) wherein m is 1 and Y is optionally substituted alkyl, optionally substituted carboxy, or optionally substituted carbamoyl, its pharmaceutically acceptable salt, or hydrate thereof.

i) A peptide derivative of any one of a) to d) wherein m is 2 or 3 and Y is optionally substituted alkyl, optionally substituted carboxy, or optionally substituted carbamoyl, its pharmaceutically acceptable salt, or hydrate thereof.

j) A pharmaceutical composition which contains any one of the compounds a) to i) as an active ingredient.

k) A composition for activating the central nervous system which contains any one of the compounds a) to i) as an active ingredient.

l) A TRH derivative having such effect that the ratio represented by the blood glucose level of the active substance-administered group/the blood glucose level of the physiological saline-administered group is 0.7 to 1.3 in the rat to which an effective amount of it for exhibiting the main activity is intravenously administered.

All of the compounds represented by the above formula have superior activity of activating the central nervous system. Specifically, the compounds having the substituents shown below in the formula (IV) are preferable.

1) A peptide derivative wherein W is oxygen, X is oxygen or sulfur, Y is carbamoyl or optionally substituted alkyl, m is 1, $R^3$ is hydrogen, $R^4$ is optionally substituted alkyl, and $R^5$ is hydrogen, its pharmaceutically acceptable salt, or hydrate thereof.

2) A peptide derivative wherein W is oxygen, X is a bond, Y is carbamoyl or optionally substituted alkyl, m is 2, $R^3$ is hydrogen, $R^4$ is optionally substituted alkyl, and $R^5$ is hydrogen, its pharmaceutically acceptable salt, or hydrate thereof.

As further preferable compounds, the compounds having the substituents shown below in the formula (IV) are exemplified.

1') A peptide derivative wherein W is oxygen, X is oxygen or sulfur, Y is carbamoyl or alkyl, m is 1, $R^3$ is hydrogen, $R^4$ is alkyl, and $R^5$ is hydrogen, its pharmaceutically acceptable salt, or hydrate thereof.

2') A peptide derivative wherein W is oxygen, X is a bond, Y is carbamoyl or alkyl, m is 2, $R^3$ is hydrogen, $R^4$ is alkyl, and $R^5$ is hydrogen, its pharmaceutically acceptable salt, or hydrate thereof.

As further preferable compounds, the compounds having the substituents shown below in the formula (IV) are exemplified.

1") A peptide derivative wherein W is oxygen, X is sulfur, Y is carbamoyl or $C_1$–$C_6$ straight or branched chain alkyl, m is 1, $R^3$ is hydrogen, $R^4$ is $C_1$–$C_3$ straight or branched chain alkyl, and $R^5$ is hydrogen, its pharmaceutically acceptable salt, or hydrate thereof.

2") A peptide derivative wherein W is oxygen, X is a bond, Y is carbamoyl or $C_1$–$C_6$ straight or branched chain alkyl, m is 2, $R^3$ is hydrogen, $R^4$ is $C_1$–$C_3$ straight or branched chain alkyl, and $R^5$ is hydrogen, its pharmaceutically acceptable salt, or hydrate thereof.

As a preferable configuration, the configuration represented by the formula (IV') for the formula (IV) (when one of $R^4$ and $R^5$ is hydrogen, the configuration shows the other one than shown in the formula)

The term "halogen" herein used means fluoro, chloro, bromo, and iodo.

The term "alkyl" herein used includes $C_1$–$C_6$ straight or branched chain alkyl and $C_3$–$C^6$ cyclic alkyl. Preferably, $C_1$–$C^6$ straight or branched chain alkyl is exemplified. Further preferably, $C_1$–$C_3$ straight, or branched chain alkyl is exemplified. Examples of alkyl are methyl, ethyl, n-propyl, iso-propyl, n-butyl, iso-butyl, sec-butyl, tert-butyl, cyclopropyl, cyclopentyl, cyclohexyl, and the like.

The term "alkenyl" herein used includes $C_2$–$C_8$ straight or branched chain alkenyl. Preferably, $C_3$–$C_6$ straight or branched chain alkenyl is exemplified. Further preferably, $C_2$–$C_5$ straight or branched chain alkenyl is exemplified. Examples of alkenyl are n-propenyl, n-butenyl, n-hexenyl, and the like.

The term "aryl" herein used includes monocyclic or condensed ring aromatic hydrocarbons. Preferably, monocyclic aromatic hydrocarbons are exemplified. Examples of aryl are phenyl, naphthyl, and the like.

The term "heteroaryl" includes a 5 to 6 membered aromatic heterocyclic group which contains one or more hetero atoms selected from the group consisting of nitrogen, oxygen and sulfur atoms in the ring, may be fused with a carbocyclic ring or an other heterocyclic ring, and may be substituted at any possible position. Examples of the heteroaryl are pyrrolyl (e.g., 1-pyrrolyl), indolyl (e.g., 2-indolyl), carbazolyl (e.g., 3-carbazolyl), imidazolyl (e.g., 4-imidazolyl), pyrazolyl (e.g., 1-pyrazolyl), benzimidazolyl (e.g., 2-benzimidazolyl), indazolyl (e.g., 3-indazolyl), indolizinyl (e.g., 6-indolizinyl), pyridyl (e.g., 4-pyridyl), quinolyl (e.g., 5-quinolyl), isoquinolyl (e.g., 3-isoquinolyl), acridinyl (e.g., 1-acridinyl), phenanthridinyl (e.g., 2-phenanthridinyl), pyridazinyl (e.g., 3-pyridazinyl), pyrimidinyl (e.g., 4-pyrimidinyl), pyrazinyl (e.g., 2-pyrazinyl), cinnolinyl (e.g., 3-cinnolinyl), phthalazinyl (e.g., 2-phthalazinyl), quinazolinyl (e.g., 2-quinazolinyl), isoxazolyl (e.g., 3-isoxazolyl), benzisoxazolyl (e.g., 3-benzisoxazolyl), oxazolyl (e.g., 2-oxazolyl), benzoxazolyl (e.g., 2-benzoxazolyl), benzisoxazolyl (e.g., 4-benzisoxazolyl), isothiazolyl (e.g., 3-isothiazolyl), benzisothiazolyl (e.g., 2-benzisothiazolyl), thiazolyl (e.g., 2-thiazolyl), benzothiazolyl (e.g., 2-benzothiazolyl), furyl (e.g., 3-furyl), benzofuryl (e.g., 3-benzofuryl), thienyl (e.g., 2-thienyl), benzothienyl (e.g., 2-benzothienyl), tetrazolyl, and the like.

The term "non-aromatic heterocyclic group" herein used means a 5 to 7 membered non-aromatic heterocyclic group which contains one or more hetero atoms selected from the group consisting of nitrogen, oxygen and sulfur atoms in the ring, and may bind at any possible position. Examples of the non-aromatic heterocyclic group are morpholino, piperidino, 1-pyrrolidinyl, 2-pyrroline-3-yl, and the like.

The term "acyl" herein used includes alkanoyl of which alkyl part is the above mentioned "alkyl" and aroyl of which aryl part is the above mentioned "aryl". Examples of acyl are acetyl, benzoyl, and the like.

The term "alkyloxy" herein used includes alkyloxy of which alkyl part is the above mentioned "optionally substituted alkyl". Examples of alkyloxy are methyloxy, ethyloxy, n-propyloxy, iso-propyloxy, n-butyloxy, iso-butyloxy, sec-butyloxy, tert-butyloxy, and the like.

The term "optionally substituted alkyl" for $R^1$ and $R^2$ herein used includes the above mentioned "alkyl" which is optionally substituted at any possible position with one or more substituents, for example, hydroxy, alkyloxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, carbamoyl, $C_1$–$C_{20}$ alkyloxycarbonyl (e.g., methoxycarbonyl, iso-propyloxycarbonyl, tetradecanyloxycarbonyl, and pentadecanyloxycarbonyl), aryloxycarbonyl (e.g., phenyloxycarbonyl), nitro, cyano, $SO_pR^A$ (p is an integer of 1 to 3, and $R^A$ is hydrogen or alkyl), $PO(OH)_2$ or $PO(O)OH$ which is optionally substituted with alkyl, substituted or unsubstituted amino (e.g., methylamino, dimethylamino, and carbamoylamino), optionally substituted aryl (e.g., phenyl and tolyl), optionally substituted heteroaryl, an optionally substituted non-aromatic-heterocyclic group, aryloxy, acyloxy, acyloxycarbonyl, alkylcarbonyl, arylcarbonyl, non-aromatic heterocyclic carbonyl, hydrazino, hydroxyamino, alkyloxyamino, and formyl. Examples of optionally substituted alkyl are methyl, ethyl, n-propyl, iso-propyl, n-butyl, iso-butyl, sec-butyl, tert-butyl, cyclopropyl, cyclopentyl, cyclohexyl, benzyl, iso-propyloxycarbonylmethyl, tetradecanyloxycarbonylmethyl, pentadecanyloxycarbonylmrthyl, and the like. As the preferred substituent, $C_1$–$C_{20}$ alkyloxycarbonyl and phenyl are exemplified.

The term "optionally substituted alkyl" for Y, $R^3$, $R^4$, and $R^5$ herein used includes the above mentioned "alkyl" which is optionally substituted at any possible position with one or more substituents, for example, hydroxy, alkyloxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, carbamoyl, alkyloxycarbonyl (e.g., methoxycarbonyl and ethoxycarbonyl), aryloxycarbonyl (e.g., phenyloxycarbonyl), nitro, cyano, $SO_pR^A$ (p is an integer of 1 to 3, and $R^A$ is hydrogen or alkyl), $PO(OH)_2$ or $PO(O)OH$ which is optionally substituted with alkyl, substituted or unsubstituted amino (e.g., methylamino, dimethylamino, and carbamoylamino), optionally substituted aryl (e.g., phenyl and tolyl), optionally substituted heteroaryl, an optionally substituted non-aromatic-heterocyclic group, aryloxy, acyloxy, acyloxycarbonyl, alkylcarbonyl, non-aromatic heterocyclic carbonyl, heterocyclic imino, hydrazino, hydroxyamino, alkyloxyamino, and formyl. For example, methyl, ethyl, n-propyl, iso-propyl, n-butyl, iso-butyl, sec-butyl, tert-butyl, cyclopropyl, cyclopentyl, cyclohexyl, benzyl, hydroxymethyl, tert-butylcarbonyloxymethyl, morpholinomethyl, piperidinomethyl, N-methyl-1-piperazinylmethyl, ethylcarbonylmethyl, morpholinocarbonylmethyl, acetyloxymethyl, and the like are exemplified. As a preferable substituent, phenyl, hydroxy, alkylcarbonyloxy, morpholino, piperidino, N-alkyl-substituted piperazinyl, alkylcarbonyl, morpholinocarbonyl, acyloxy are exemplified.

The term "optionally substituted alkyl" for nitrogen in the thiazolyl ring herein used includes $C_1$–$C_3$ straight or branched chain alkyl which is optionally substituted with phenyl optionally substituted with halogen or alkyl. For example, methyl, ethyl, n-propyl, n-butyl, benzyl, 4-methylbenzyl are exemplified.

The terms "optionally substituted aryl", "optionally substituted heteroaryl", and "an optionally substituted non-aromatic heterocyclic group" herein used include the above mentioned "aryl", "heteroaryl", and "a non-aromatic heterocyclic group", respectively, which are optionally substituted with one or more substituents, for example, hydroxy, alkyloxy (e.g. methoxy and ethoxy), mercapto, alkylthio (e.g., methylthio), halogen (e.g., fluoro, chloro, bromo, and iodo), carboxy, alkyloxycarbonyl (e.g., methoxycarbonyl and ethoxycarbonyl), nitro, cyano, haloalkyl (e.g., trifluoromethyl), aryloxy (e.g., phenyloxy), substituted or unsubstituted amino (e.g., methylamino, dimethylamino, diethylamino, and bezylideneamino), guanizino, alkyl (e.g., methyl, ethyl, n-propyl, iso-propyl, n-butyl, iso-butyl, sec-butyl, tert-butyl, n-pentyl, iso-pentyl, neo-pentyl, tert-pentyl, cyclopropyl, cyclobutyl, and cyclopentyl), alkenyl (e.g., vinyl and propenyl), alkynyl (e.g., ethynyl and phenylethynyl), alkanoyl (e.g., formyl, acetyl and propionyl), acyloxy (e.g., acetyloxy) acylamino, alkylsulfonyl (e.g., methylsulfonyl), phenyl, benzyl, an azo group (e.g., phenylazo), optionally substituted heteroaryl (e.g., 3-pyridyl), optionally substituted ureido (e.g., ureido and phenylureido), and the like.

The substituents for "optionally substituted carboxy" of Y are, for example, straight or branched chain $C_1$–$C_{20}$ alkyl, cyclic $C_3$–$C_8$ alkyl, and aryl. Further, these alkyl and aryl are optionally substituted with one or more substituents which are exemplified as those for the above "optionally substituted alkyl" and "optionally substituted aryl". Examples of the "optionally substituted carboxy" are carboxy, alkyloxycarbonyl and aryloxycarbonyl, for example, methoxycarbonyl, iso-propyloxycarbonyl, hexyloxycarbonyl, decyloxycarbonyl, phenyloxycarbonyl, tetradecyloxycarbonyl, icosanyloxycarbonyl, phenoxymethylcarbonyl, benzyloxycarbonyl, tolyloxycarbonyl, and the like. As a preferable substituent, straight or branched chain $C_1$–$C_{20}$ alkyl and benzyl are exemplified.

The substituents for "optionally substituted carbamoyl" of Y are, for example, straight or branched chain $C_1$–$C_6$ alkyl (e.g., methyl, ethyl, n-propyl, and iso-propyl). Further, this alkyl is optionally substituted with one or more substituents which are exemplified as those for the above "optionally substituted alkyl". Examples of the "optionally substituted carbamoyl" are carbamoyl, methylcarbamoyl, ethylcarbamoyl, n-propylcarbamoyl, methylethylcarbamoyl, benzylcarbamoyl, iso-propyloxycarbonylmethylcarbamoyl, tetradecanyloxycarbonylmethylcarbamoyl, benzyloxycarbonylmethylcarbamoyl, acetyloxymethylcarbamoyl, acetylcarbamoyl, and the like. As a preferable substituent, $C_1$–$C_{20}$ alkyloxycarbonylalkyl and acyloxyalkyl are exemplified.

The substituents for "optionally substituted carboxy" of $R^3$ are, for example, the above mentioned "optionally substituted alkyl" and "optionally substituted aryl". Examples of the "optionally substituted carboxy" are carboxy, alkyloxycarbonyl, and aryloxycarbonyl, for example, methoxycarbonyl, ethoxycarbonyl, phenoxycarbonyl, phenyloxymethylcarbonyl, tolyloxycarbonyl, and the like.

The term "optionally substituted acyl" herein used includes alkanoyl of which alkyl part is the above mentioned "optionally substituted alkyl" and aroyl of which aryl part is the above mentioned "optionally substituted aryl". Examples of the "optionally substituted acyl" are toluoyl and the like.

The term "optionally substituted imino" herein used includes the imino which is optionally substituted with the above mentioned "optionally substituted lower alkyl", "optionally substituted aryl", alkyloxycarbonyl, and the like.

BEST MODE FOR CARRYING OUT THE INVENTION

Figure 1:
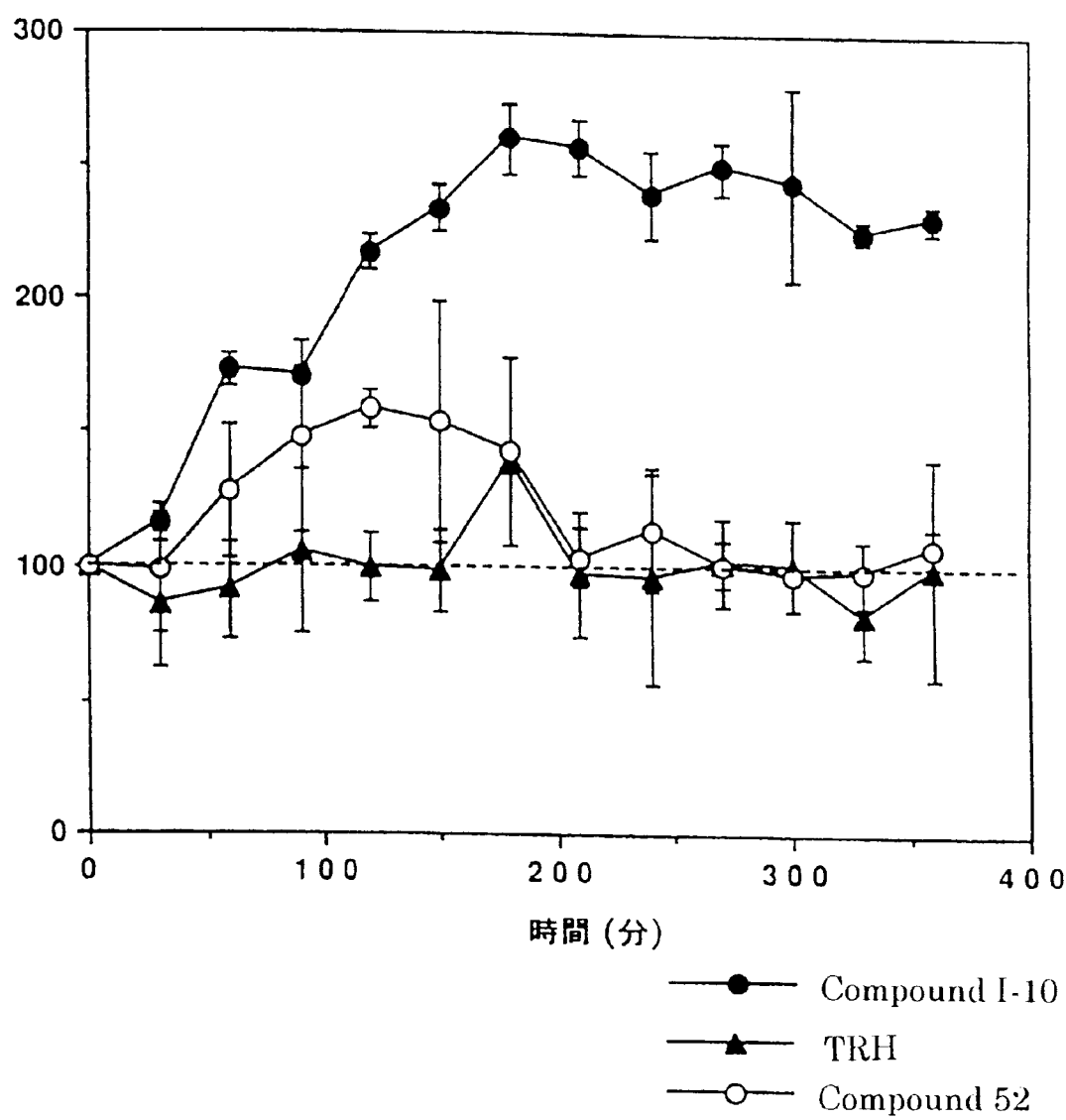
FIG. 1 shows the effect of releasing acetylcholine in cerebral cortex when the test compound is orally administered to rats (the horizontal axis shows time course and the vertical axis shows a concentration of acetylcholine in cerebral cortex.).

The compounds of this invention are able to be synthesized by means of the following methods A and B as a usual method of the peptide synthesis. The substituents, for example, Y and the like are able to be introduced by alkylation, acylation, esterification, etc. after the tripeptide was synthesized in the same manner as the method A or B.

The compound represented by the formula (VII):

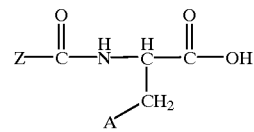

(VII)

wherein A and Z are as defined above, and the compound of the formula (VIII):

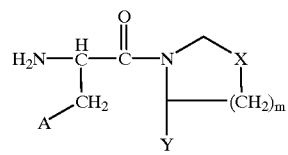

(VIII)

wherein A, X, Y, and m are as defined above, which are intermediates for the methods A and B, are novel.

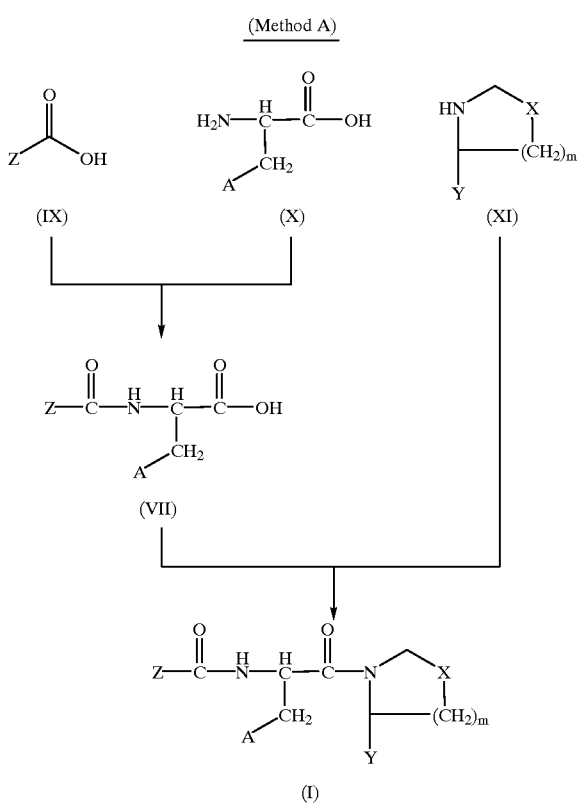

(Method A)

wherein A, X, Y, Z and m are as defined above.

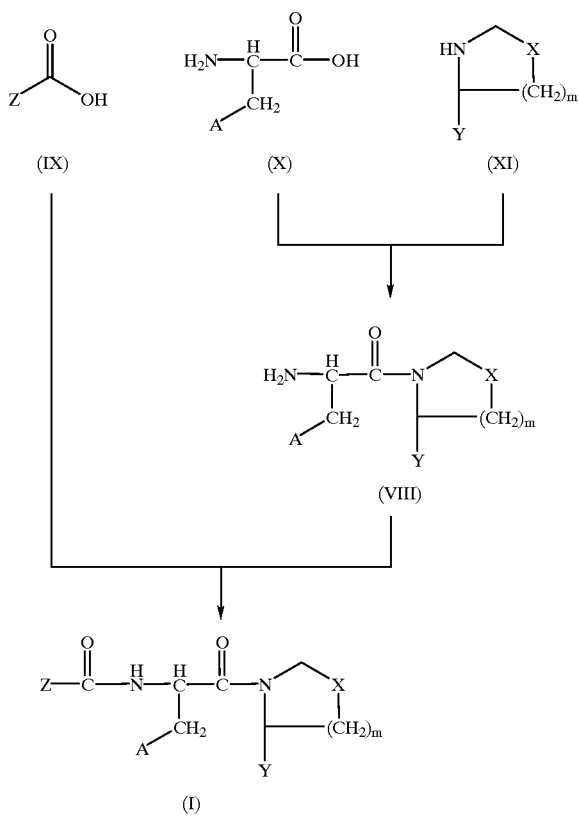

(Method B)

wherein A, X, Y, Z, and m are as defined above.

The methods A and B are to obtain the aimed compound of tripeptide (I) using the amino acid derivatives represented by the formulas (IX), (X), and (XI) as a starting material. In the method A the compound (IX) is reacted with the compound (X) to give the compound (VII), which is further reacted with the compound (XI). In the method B the compound (X) is reacted with the compound (XI) to give the compound (VIII), which is then reacted with t,he compound (IX). Each reaction is carried out in accordance with a usual peptide synthetic reaction, for example, the method described in "The peptide". vol. 1, "Peptide Synthesis", Nobuo Izumiya, Maruzen and the like.

As a usual peptide synthetic reaction, exemplified are the method of using a condensing agent such as N,N-dicyclohexylcarbodiimide (DCC) and the like, the azide method, the acid chloride method, the acid anhydride method, the activated ester method, and the like. When the starting material has a substituent interfering this peptide synthetic reaction, for example, amino, carboxy, hydroxy, etc., the substituent can previously be protected in accordance with the method of "Protective Groups in Organic Synthesis" Theodora W. Green (John Wiley & Sons), and then deprotected at an appropriate step.

Examples of an amino protective group are t-butyloxycarbonyl, benzyloxycarbonyl, 9-fluorenylmethoxycarbonyl, phthaloyl, tritluoroacetyl, and the like.

Examples of a carboxy protective group are esters such as methyl ester, ethyl ester, benzyl ester, t-butyl ester, 2-(trimethylsilyl)ethyl ester, etc.

As the method to activate the carboxy concerning the reactions of the compounds (VII), (IX), and (X), the following methods are exemplified; 1) the method to give activated esters such as N-hydroxysuccinimide ester, N-hydroxybenzotriazole ester, p-nitrophenol ester, and the like, 2) the method to give acid chlorides using chlorination agents such as phosphorus oxychloride, phosphorous trichloride, thionyl chloride, oxalyl chloride, and the like, 3) the method to give azides, 4) the method to give acid anhydrides. These methods are able to be carried out in the presence or absence of a deoxidizer in an appropriate solvent such as N,N-dimethylformamide, acetonitrile, tetrahydrofuran, methylene chloride, and the like at −50° C. to reflux.

The active derivatives of carboxylic acids which are produced by the above methods are isolated and are able to be reacted with the compounds (VIII), (X), and (XI) having an amino group concerning this reaction. Without isolating the active derivatives of carboxylic acids in the above methods, the compounds (VIII), (X), and (XI) having an amino group concerning this reaction may be added to the reaction solution of the above methods. 1-Hydroxybenzotriazole may be added to the reaction mixture to expedite these reactions.

In this way, the compounds of this invention are able to be synthesized from amino acid derivatives of the compounds (IX), (X), and (XI) by two peptide synthetic reactions. The starting material of the amino acid derivatives are able to be obtained as known natural compounds and to be synthesized from them easily. The compound (IX) is able to be synthesized in accordance with the methods described in J. Med. Chem., 33, 2130 (1990), Int. J. Peptide Protein Res., 14, 216 (1979), Chem. Lett., 1171 (1982), and Tetrahedron Lett., 36, 6569 (1995). The compound (X) is able to be synthesized in accordance with the methods described in Synthetic Commun., 20, 3507 (1990) and EP 417454. The compound (XI) is able to be synthesized in accordance with the method described in J. Med. Chem., 24, 692 (1981).

The term "the compounds of this invention" herein used includes pharmaceutically acceptable salts or hydrates of the compounds. For example, salts with alkali metals (e.g., lithium, sodium, and potassium), alkaline earth metals (e.g., magnesium and calcium), ammonium, organic bases, amino acids, mineral acids (e.g., hydrochloric acid, hydrobromic acid, phosphoric acid, and sulfuric acid), or organic acids (e.g., acetic acid, citric acid, maleic acid, fumaric acid, benzenesulfonic acid, and p-toluenesulfonic acid) and hydrates of them are exemplified. These salts and hydrates can be formed by the usual method.

The compound of this invention is TRH derivative of which the histidine residue is converted into the residue of 3-(4-thiazolyl)alanine or 3-(5-thiazolyl)alanine and has strong, continuous, and selective action on the central nervous system. Administration of TRH and conventional TRH derivatives acutely raises up the blood glucose level and acutely let it fall down by the rebound, which are not observed in the compound of this invention. This fact may lead to the less side effect.

Since the compound of this invention has superior hyperthermia and locomotor increment effects caused by activation of the neurones such as dopamine system, norepinephrine system, and acetylcholine system in brain, it is useful for treatment of disorders accompanied with dysfunction of these nervous systems. Especially, as it remarkably activates the acetylcholine neurone system in cerebral cortex, it may be useful as a therapeutic agent of disorders such as motor disturbance, disturbance of consciousness, senile dementia, sopor, decline of concentration, speech dysfunction, and the like accompanied with the dysfunction of the acetylcholine neurone.

When the compound of this invention is administered to a person for treatment or prevention of the above diseases, it can be administered by oral administration such as powder, granules, tablets, capsules, pilulae, and liquid medicine, or by parenteral administration such as injections, suppository, percutaneous formulations, insufflation. or the like. An effective amount of the compound of this invention is formulated by being mixed with medicinal admixture such as excipient, binder penetrant, disintegrators, lubricant, and the like if necessary. When parenteral injection is prepared, the compound of this invention and an appropriate carrier are sterilized to prepare it.

An appropriate dosage varies with the conditions of the patients, an administration route, their age, and their body weight. In the case of oral administration to adult, a dosage can generally be between 0.1–100 mg/kg/day, preferably 1–20 mg/kg/day.

The following examples are provided to further illustrate the present invention and are not to be construed as limiting the scope thereof.

Abbreviations described below are used in the following examples.
c-: cyclo
Me: methyl
Et: ethyl
Pr: propyl
Bu: butyl
Pen: pentyl
Hex: hexyl
Ph: phenyl
Ac: acetyl
BOC: tert-butyloxycarbonyl
Bzl: benzyl
Cbz: benzyloxycarbonyl
p-TsOH: p-toluenesulfonic acid
DCC: N,N-dicyclohexylcarbodiimide
HOBT: 1-hydroxybezotriazole

EXAMPLE

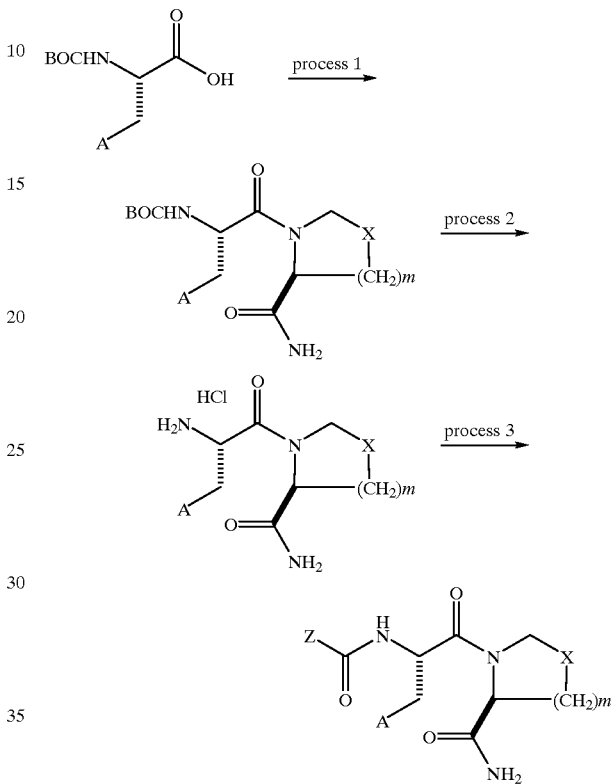

Example 1

Process 1

Preparation of N-(tert-butoxycarbonyl)-3-(4-thiazolyl)-L-alanyl-L-prolineamide (1)

N-(tert-butyloxycarbonyl)-3-(4-thiazolyl)-L-alanine (8.17 g, 30 mmol) which was synthesized in accordance with the method described in the literature (Synthetic Commun., 20, 3507 (1990)) and L-prolineamide (3.42 g, 30 mmol) were dissolved in N, N-dimethylformamide (100 ml). To this solution was added the solution of dicyclohexylcarbodiimide (DCC, 6.81 g, 33 mmol) in N,N-dimethylformamide (10 ml) and 1-hydroxybenzotriazole (405 mg, 3 mmol) under ice-cooling with stirring and the resulting mixture was stirred overnight, at room temperature. To the reaction mixture was added ethyl acetate (200 ml) and the precipitation which appeared was filtered off. The filtrate was concentrated in vacuo. The residue (15.98 g) was subjected to silica gel column chromatography (chloroform: methanol=98:2 to 97:3) to give the compound (1) (10.01 g, 90.6%).

The compounds (2) an(d (3) were synthesized in a manner similar to that described in the above method. The results were shown in Table 1.

TABLE 1

[Structure: Boc—NH—CH(CH₂—A)—C(=O)—N-pyrrolidine ring with X and C(=O)NH₂ substituents]

| Example No. | Compound No. | A | X | [α]D | melting point (° C.) | NMR |
|---|---|---|---|---|---|---|
| 1-1 | 1 | 4-thiazolyl | CH₂ | -57.1° (c = 1.004, CHCl₃, 23.5° C.) | | (CD₃OD) 1.38(9H, s), 1.8–2.3 (4H, m), 3.19(2H, ddd), 3.47 (1H, m), 3.76(1H, m), 4.44 (1H, dd), 4.68(1H, dd, J=6.2, 7.4Hz), 7.33, 7.40(total 1H, d, J=1.6Hz), 8.93(1H, d, J=1.6Hz) |
| 2-1 | 2 | 4-thiazolyl | S | -81.8° (c = 0.501, MeOH, 23° C.) | | (CD₃OD) 8.95(bs, 1H), 7.40 (bs, 1H), 4.6–5.0(3H), 4.44 (d, J=8.6Hz, 1H), 3.0–3.4 (4H), 1.39(s, 9H) |
| 3-1 | 3 | 5-thiazolyl | CH₂ | -53.5° (c = 1.000, MeOH, 23.5° C.) | 216–218 | (CDCl₃) 8.88(1H, s), 7.70 and 7.73 (total 1H, s), 4.57 (1H, dd, J=4.4, 9.9Hz), 4.43 (1H, dd, J=4.2, 8.2Hz), 3.72 (2H, m), 3.40(1H, dd, J=4.4, 15.2Hz), 3.12(1H, dd, J=9.8, 15.2Hz), 2.40–1.80 (4H, m), 1.38(9H, s) |

Example 1
Process 2

Preparation of 3-(4-thiazolyl)-L-alanyl-L-prolineamide dihydrochloride (4)

To a solution of the compound (1, 5.53 g. 15 mmol) in ethyl acetate (30 ml) was added a solution of 4N-hydrochloride in ethyl acetate (75 ml, 300 mmol) under ice-cooling and the resulting mixture was stirred for 2.5 h at the same temperature. To the reaction mixture was added diethyl ether (400 ml) and the precipitation which appeared was filtered off. The precipitation was washed with diethyl ether and dried in vacuo with vacuum pump to give 6.67 g of the compound (4). This compound was used in the next reaction without purification.

The compounds (5) and (6) were synthesized in a manner similar to that described in the above method. The results were shown in Table 2.

TABLE 2

[Structure: H₂N—CH(CH₂—A)—C(=O)—N-pyrrolidine ring with X and C(=O)NH₂ substituents · 1 or 2 HCl]

| Example No. | Compound No. | A | X | [α]D | NMR |
|---|---|---|---|---|---|
| 1-2 | 4 | 4-thiazolyl | CH₂ | -29.0° (c = 1.006, MeOH, 26° C.) | (D₂O) 9.53(1H, d, J=2.1Hz), 7.89 (1H, d, J=2.1Hz), 4.66(1H, t, J=5.7Hz), 4.53(1H, dd, J=5.4, 8.4 Hz), 3.50–3.7(4H, m), 2.5–1.8(4H, m) |
| 2-2 | 5 | 4-thiazolyl | S | | (D₂O) 9.12 and 9.10(total 1H, s), 7.61 and 7.56(total 1H, s), 4.9–4.7 (3H, m), 4.41(1H, d, J=9.6Hz), 3.4–3.6(3H, m), 3.20(1H, dd, J=5.8, 12.6Hz) |
| 3-2 | 6 | 5-thiazolyl | CH₂ | | (CD₃OD) 8.40 and 8.23(total 1H, s), 4.72(1H, t, J=5.4Hz), 4.51(1H, dd, J=5.4, 8.6Hz), 4.20–3.40(4H, m), 2.5–1.8(4H, m) |

Example 1

Process 3

Preparation of L-pyroglutamyl-3-(4-thiazolyl)-L-alanyl-L-prolineamide dihydrochloride (I-1)

L-Pyroglutamic acid (1.76 g, 13.64 mmol) and N-hydroxysuccinimide (1.73 g, 15 mmol) were dissolved in N,N-dimethylformamide (50 ml). To this solution was added the solution of DCC (3.09 g, 15 mmol) in N,N-dimethylformamide (10 ml) under ice-cooling and the resulting mixture was stirred for 2 h at, the same temperature. 3-(4-thiazolyl)-L-alanyl-L-prolineamide dihydrochloride (4) (6.67 g, 15 mmol) and triethylamine (4.6 ml. 33 mmol) were added successively to the solution and the reaction mixture was stirred overnight. After the precipitation which appeared was filtered off, to the filtrate was added sodium hydrogencarbonate aq. to adjust pH 8. The reaction mixture was subjected to gel filtration column chromatography (MCI gel CHP-20P, 200 ml, aq. MeOH) to give the compound (I-1) (2.54 g, 49%).

The compounds (I-2) to (I-12) were synthesized in a manner similar to that described in the above method. The results were shown in Tables 3 to 6.

TABLE 3

| Example No. | Compound No. | A | X | $[\alpha]D$ | IR (cm$^{-1}$) | NMR |
|---|---|---|---|---|---|---|
| 1-3 | I-1 | 4-thiazolyl | CH$_2$ | −42.9° (c = 1.003, MeOH, 24° C.) | (KBr) 3294, 1683, 1639, 1541, 1518, 1444, 1263 | (CD$_3$OD) 8.95(1H, d, J=2 Hz), 7.43 and 7.34(total 1H, d, J=2Hz), 4.95(1H, t, J=7 Hz), 4.42 and 4.34(total 1H, m), 4.17(1H, m), 3.80(1H, m), 3.1–3.6(3H, m), 1.8–2.5 (8H, m). |
| 2-3 | I-2 | 4-thiazolyl | S | −87.6° (c = 1.012, H$_2$O, 23° C.) | (KBr) 3301, 2936, 1685, 1518, 1419, 1330, 1262 | (CD$_3$OD) 8.95(1H, d, J=1.8 Hz), 7.43 and 7.37(total 1H, d, J=1.8Hz), 5.05(1H, t, J=6.8Hz), 4.99(1H, d, J=8.6 Hz), 4.86(1H, m), 4.45(1H, d, J=8.6Hz), 4.18(1H, dd, J=5, 8.6Hz), 3.1–3.5(4H, m), 1.9–2.5(4H, m) |
| 3-3 | I-3 | 5-thiazolyl | CH$_2$ | −53.6° (c = 1.002, MeOH, 23° C.) | (KBr) 3393, 3081, 1684, 1639, 1540, 1443, 1247 | (CD$_3$OD) 8.86(1H, s), 7.75 and 7.71(total 1H, d, J=0.6 Hz), 4.90(1H, m), 4.42(1H, dd, J=4.5, 8.4Hz), 4.18(1H, dd, J=4.8, 8.7Hz), 3.95–3.60 (2H, m), 3.50(1H, dd, J=4.5, 15.3Hz), 3.24(1H, dd, J=9.3, 15.3Hz), 2.60–1.80 (8H, m). |

TABLE 4

| Example No. | Compound No. | A | X | $[\alpha]D$ | IR (cm$^{-1}$) | NMR |
|---|---|---|---|---|---|---|
| 4-3 | I-4 | 4-thiazolyl | CH$_2$ | −10.4° | (KBr) | (D$_2$O) 8.93(1H, s), 7.35 and |

TABLE 4-continued

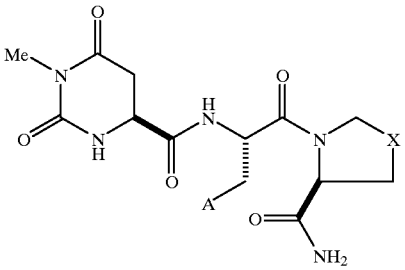

| Example No. | Compound No. | A | X | [α]D | IR (cm⁻¹) | NMR |
|---|---|---|---|---|---|---|
| | | | | (c = 1.005, H₂O, 24° C.) | 3397, 2954, 1719, 1676, 1542(w), 1519(w), 1448 | 7.29(1H, s), 5.03(1H, m), 4.39(1H, m), 4.21(1H, m), 3.76(1H, m), 3.57(1H, m), 2.7–3.4(4H, m), 3.04 and 3.4 (4H, m), 3.04 and 3.01(total 3H, s), 1.8–2.4(4H, m). |
| 5-3 | I-5 | 4-thiazolyl | S | −37.3° (c = 1.005, H₂O, 23° C.) | (KBr) 3313, 2931, 1720, 1675, 1517, 1468, 1435, 1305, 1125. | (CD₃OD) 8.93(1H, d, J=1.8 Hz), 7.39 and 7.33(total 1H, d, J=1.8Hz), 5.02(1H, t, J=6.8Hz), 4.95(1H, d, J=8.8 Hz), 4.86(1H, m), 4.46(1H, d, J=8.8Hz), 4.09(1H, dd, J=4.4, 7.2Hz), 3.1–3.5(4H, m), 3.06(3H, s), 2.97(1H, dd, J=7.2, 16.6Hz), 2.78 (1H, dd, J=4.2, 16.6Hz) |
| 6-3 | I-6 | 5-thiazolyl | CH₂ | −12° (c = 1.011, MeOH, 23° C.) | (KBr) 3318, 1720, 1675, 1523, 1448, 1356, 1304, 1270. | (CD₃OD) 8.87(1H, s), 7.67 and 7.73(total 1H, s), 4.90 (1H, m), 4.42(1H, dd, J=4.4, 8.2Hz), 4.09(1H, dd, J=3.6, 7Hz), 3.70(2H, m), 3.49 (1H, dd, J=4.2, 15.4Hz), 3.21(1H, dd, J=9.2, 15.4 Hz), 3.08 and 3.05(total 3H, s), 2.92(1H, dd, J=7, 12.6 Hz), 2.78(1H, dd, J=3.6, 12.6Hz), 2.4–1.8(4H, m). |

TABLE 5

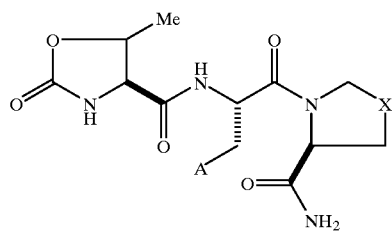

| Example No. | Compound No. | A | X | [α]D | IR (cm⁻¹) | NMR |
|---|---|---|---|---|---|---|
| 7-3 | I-7 | 4-thiazolyl | CH₂ | −30.3° (c = 1.003, H₂O, 25° C.) | (KBr) 3398, 1752, 1677, 1641, 1517, 1445, 1229. | (CD₃OD) 8.95(1H, d, J=2 Hz), 7.43 and 7.33(1H, d, J=2Hz), 4.97(1H, t, J=7 Hz), 4.3–4.6(2H, m), 3.93 (1H, d, J=5.4Hz), 3.78(1H, m), 3.1–3.6(3H, m), 1.7–2.3 (4H, m), 1.45(3H, d, J=6.6 Hz). |
| 8-3 | I-8 | 4-thiazolyl | S | −58.8° (c = 1.010, H₂O, 23° C.) | (KBr) 3397, 2980, 2932, 1752, | (CD₃OD) 8.95(1H, d, J=1.8 Hz), 7.43 and 7.36(1H, d, J=1.8Hz), 5.07(1H, t, J=6.6 Hz), 4.98(1H, d, J=8.6Hz), 4.86(1H, m), 4.4–4.6(1H, |

TABLE 5-continued

| Example No. | Compound No. | A | X | [α]D | IR (cm⁻¹) | NMR |
|---|---|---|---|---|---|---|
| | | | | | 1677, 1649, 1519, 1413, 1227 | m), 4.45(1H, d, J=8.6Hz), 3.95(1H, d, J=5Hz), 3.1–3.5 (4H, m), 1.46(3H, d, J=6.2 Hz). |
| 9-3 | I-9 | 5-thiazolyl | $CH_2$ | −25.8° (c = 1.009, $H_2O$, 23° C.) | (KBr) 3397, 1753, 1677, 1639, 1527, 1446, 1403, 1301, 1230 | ($CD_3OD$) 8.89(1H, s), 7.76 and 7.71(total 1H, s), 4.90 (2H, m), 4.43(1H, dd, J=5.4, 6.3Hz), 3.93(1H, d, J=5.4 Hz), 4.1–3.6(2H, m), 3.50 (1H, dd, J=4.2, 15Hz), 3.25 (1H, dd, J=9.3, 15Hz), 2.4– 1.8(4H, m), 1.44(3H, d, J=6.3Hz). |

TABLE 6

| Example No. | Compound No. | A | X | [α]D | IR (cm⁻¹) | NMR |
|---|---|---|---|---|---|---|
| 10-3 | I-10 | 4-thiazolyl | $CH_2$ | −52.1° (c = 1.006, $H_2O$, 26° C.) | (KBr) 3392, 1751, 1676, 1638, 1542, 1519, 1446, 1407, 1235, 1097 | ($CD_3OD$) 8.95(1H, d, J=1.8 Hz), 7.43 and 7.35(total 1H, d, J=1.8Hz), 5.02(1H, t, J=7.1Hz, 1H), 4.90(1H, m), 4.38(1H, m), 4.33(1H, d, J=8.6Hz), 3.88(1H, m), 3.1– 3.6(3H, m), 1.9–2.3(4H, m), 1.26 and 1.20(total 3H, d, J=6.6Hz). |
| 11-3 | I-11 | 4-thiazolyl | S | −80.3° (c = 1.010, $H_2O$, 23° C.) | (KBr) 3308, 2985, 2936, 1752, 1678, 1651, 1518, 1414, 1333, 1231, 1096 | ($CD_3OD$) 8.99 and 8.95(total 1H, d, J=2Hz), 7.43 and 7.39(total 1H, d, J=2Hz,), 5.11(1H, t, J=6.5Hz), 5.10 (1H, d, J=8.6Hz), 4.7–5.0 (2H, m), 4.48(1H, d, J=8.6 Hz), 4.34(1H, d, J=8.8Hz), 3.1–3.5(4H, m), 1.22(3H, d, J=6.6Hz) |
| 12-3 | I-12 | 5-thiazolyl | $CH_2$ | −46.2° (c = 1.002, MeOH, 23° C.) | (KBr) 3406, 1752, 1677, 1638, | ($CD_3OD$) 8.89 and 8.80(total 1H, s), 7.73 and 7.77(total 1H, s), 4.90(1H, m), 4.90 (1H, m), 4.41(1H, dd, J=5.2 and 9Hz), 4.35(1H, d, J=8.7 |

TABLE 6-continued

| Example No. | Compound No. | A | X | [α]D | IR (cm⁻¹) | NMR |
|---|---|---|---|---|---|---|
| | | | | | 1542, 1447, 1404, 1343, 1300, 1237 | Hz), 3.90(1H, m), 3.71(1H, m), 3.50(1H, dd, J=4.2, 15.3 Hz), 3.25(1H, dd, J=9.6, 15.3Hz), 2.4–1.8(4H, m), 1.26 and 1.18(total 3H, d, J=6.3Hz). |

Example 13

Preparation of L-2-oxo-oxazolidine4-yl-carbonyl-3-(4-thiazolyl)-L-alanyl-L-prolineamide (I-13)

The compound (I-13) was obtained in a manner similar to that described in the method of Example 1-3.

Example 14

Preparation of trans-L-N-benzyl-5-methyl-2-oxo-oxazolidine-4-yl-carbonyl-3-(4-thiazolyl)-L-alanyl-L-prolineamide (I-14).

(1) trans-L-5-Methyl-2-oxo-oxazolidine-4-carboxylic acid benzyl ester (706 mg, 3 mmol) which was synthesized in accordance with the method described in Tetrahedron Lett., 36, 6569 (1995) was dissolved in N,N-dimethylformamide (8 ml). After benzyl bromide (0.39 ml, 3.28 mmol) was added to the solution, 60% sodium hydride (120 mg, 3 mmol) was added to the mixture over 5 min. with stirring. The mixture was stirred for 3 h at room temperature. The reaction mixture was partitioned between ice-water and ethyl acetate. The organic layer was washed with water, dried over magnesium sulphate, and concentrated in vacuo. The residue was subjected to Lobar® column B (Merck inc.) and the fractions eluting with toluene:acetone=30:1 were collected to yield trans-L-N-benzyl-5-methyl-2-oxo-oxazolidine-4-carboxylic acid benzyl ester (859 mg. 88%) as colorless oil.

NMR (CDCl₃): 7.1–7.5 (10H, m), 5.17 (2H, s),4.92 (1H, d, J=14.6 Hz),4.56 (1H, m),4.14(1H, d, J=14.6 Hz), 3.63 (1H, d, J=5.2 Hz), 1.39 (3H, d, J=6.4 Hz).

The compound (860 mg, 2.61 mmol) obtained in the above process was dissolved in mixed solvents of tetrahydrofuran (18 ml) and 1,2-dimethoxyethane (2.7 ml). To the mixture was added the solution of lithium hydroxide monohydrate (548 mg, 13.1 mmol) in water (10 ml) and the resulting mixture was stirred for 30 min. at room temperature. The reaction mixture was poured into ice-water and extracted with diethyl ether three times. To the alkali layer was added 5N hydrochloric acid (3 ml) for adjusting pH 1 and the mixture was extracted with ethyl acetate twice. The organic layer was washed with water, dried over magnesium sulphate, and concentrated in vacuo. The residue (574 mg. 93.5%) was recrystallized from acetone-hexane to give trans-L-N-benzyl-5-methyl-2-oxo-oxazolidine-4-carboxylic acid (493 mg, 80.3%).

mp: 127° C.

$[\alpha]_D$=−7.8° (c=1.003, CHCl₃, 24° C.)

IR (KBr) cm⁻¹: 2716, 2601, 1740, 1692, 1497, 1442, 1421, 1369, 1248, 1201, 1186, 1078.

IR (CHCl₃) cm⁻¹: 1758, 1496, 1455, 1415, 1227, 1223, 1212, 1205.

NMR (DMSO-d6): 7.2–7.5 (5H, m), 4.69 (1H, d, J=15.4 Hz), 4.62 (1H, m),4.15 (1H, d, J=15.4 Hz), 3.71 (1H, d, J=4.4 Hz), 1.32 (3H, d, J=6.2 Hz).

Elemental analysis ($C_{12}H_{13}NO_4$) Calcd.: C,61.27; H,5.57; N,5.96. Found: C,61.30; H,5.61; N,5.91.

Compound (I-14) was obtained in a manner similar to that described in the Example 1–3.

Example 15

Preparation of trans-L-N,5-dimethyl-2-oxo-oxazolidine-4-yl-carbonyl-3-(4-thiazolyl)-L-alanyl-L-prolineamide (I-15)

To a solution of trans-L-5-methyl-2-oxo-oxazolidine-4-carboxylic acid benzyl ester (488 mg, 2.075 mmol) in N,N-dimethylformamide (6 ml) was added iodomethane (0.17 ml, 2.73 mmol) under ice-cooling in nitrogen atmosphere with stirring. Subsequently, 60% sodium hydride (83 mg, 2.075 mmol) was added to the mixture over 10 min. The reaction mixture was stirred for 3 h at the same temperature. The reaction mixture was partitioned between ice-water and ethyl acetate. The organic layer was washed with water, dried over magnesium sulphate, and concentrated in vacuo. The residue (503 mg) was subjected to Lobar® column B (Merck inc.) and the fractions eluting with toluene:acetone=30:1 were collected to yield trans-L-N,5-dimithyl-2-oxo-oxazolidine-4-carboxylic acid benzyl ester (444 mg. 85.8%) as colorless oil.

NMR(CDCl₃): 7.37 (5H, m), 5.27 (1H, d, J=12.2 Hz), 5.20 (1H, d, J=12.2 Hz), 4.51 (1H, m), 3.86 (1H, d, J=5.4 Hz), 2.92(3H, s), 1.50 (3H, d, J=6.2 Hz).

A solution of the compound (551 mg, 2.21 mmol) which was obtained the above process in mixed solvents of methanol (10 ml)-water (1 ml) was hydrogenated using 5% Pd/C (150 mg) for 1 h at room temperature. The catalyst, was filtered off and the filtrate was concentrated in vacuo to obtain trans-L-N,5-dimethyl-2-oxo-oxazolidine-4-carboxylic acid (345 mg, 98%).

mp: 125–127° C.
[α]$_D$=−11.1° (c=1.005, MeOH, 24° C.)
IR(KBr)cm$^{-1}$: 3433, 2585, 1743, 1697, 1483, 1443, 1408, 1227, 1034.
NMR(DMSO-d6): 4.51 (1H,m), 3.99 (1H, d J=5.4 Hz), 2.79 (3H, s), 1.38 (3H, d, J=6.2 Hz).

Elemental analysis (C$_6$H$_9$NO$_4$) Calcd.: C,45.28; H,5.70; N,8.80. Found: C,45.40; H,5.63; N,8.74.

The compound (I-15) was obtained in a manner similar to that described in the method of Example 1–3. The results were shown in Table 7.

TABLE 7

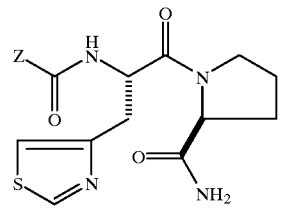

| Example No. | Compound No. | Z | [α]D | IR (cm$^{-1}$) | NMR |
|---|---|---|---|---|---|
| 13 | I-13 | (oxazolidinone, NH) | −53.0° (c = 1.009, H$_2$O, 25° C.) | (KBr) 3294, 1752, 1676, 1637, 1542, 1519, 1446, 1407, 1237 | (CD$_3$OD) 8.95(1H, d, J=2 Hz), 7.43 and 7.33(total 1H, d, J=2Hz), 4.96(1H, t, J=7.1Hz), 4.2–4.6(4H, m), 3.80(1H, m), 3.1–3.6 (3H, m), 1.9–2.3(4H, m) |
| 14 | I-14 | (oxazolidinone, N-CH$_2$Ph, Me) | −43.7° (c = 1.008, H$_2$O, 24.5° C.) | (KBr) 3412, 1752, 1679, 1644, 1543, 1516, 1442, 1415, 1227, 1206, 1092, 1066. | (CD$_3$OD) 8.99(1H, d, J=2 Hz), 7.41(1H, d, J=2.1 Hz), 7.1–7.5(5H, m), 4.95 (1H, m), 4.73(1H, d, J=15.2Hz), 4.42(2H, m), 3.87(2H, d, J=15.2Hz), 3.78(1H, m), 3.68(1H, d, J=5.1Hz), 3.0–3.6(3H, m), 1.8–2.3(4H, m), 1.35 (3H, d, J=6.4Hz). |
| 15 | I-15 | (oxazolidinone, N-Me, Me) | −31.9° (c = 1.000, H$_2$O, 23° C.) | (KBr) 3412, 1751, 1678, 1519, 1544, 1519, 1437, 1401, 1237. | (CD$_3$OD) 8.96(1H, d, J=2 Hz), 7.44 and 7.35(total 1H, d, J=2Hz), 5.04(1H, dd, J=6.2, 7.8Hz), 4.40 (2H, m), 3.88(1H, d, J=5.4Hz), 3.80(1H, m), 3.1–3.6(3H, m), 2.67(3H, s), 1.8–2.3(4H, m), 1.43 (3H, d, J=6.4Hz) |

Example 16

Preparation of 4-[2-L-pyroglutamyl-2-{(S)-2-carbamoylpyrrolidine-1-ylcarbonyl}ethyl]-3-methylthiazolium iodide (I-16)

To a solution of the compound (I-1)(5 g, 13.18 mmol) in acetonitrile (500 ml) was added iodomethane (67 ml, 1.07 mol) and the resulting mixture was heated at reflux on oil bath (80° C.) for 20 h. After the reaction mixture was cooled at 0° C., the supernatant liquid was removed by decanting. The precipitate was washed with cold acetonitrile and was added diethyl ether. The crystal powder was collected by filtration to give 6.64 g of compound (I-16) as yellow powder. Using a procedure analogous to that described above, the compounds (I-17) to (I-27) were synthesized. The results were shown in Table 8 to Table 10.

TABLE 8

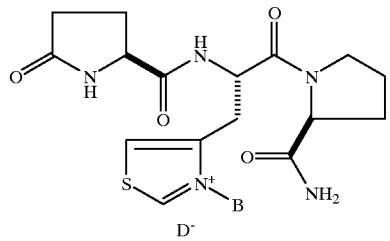

| Example No. | Compound No. | B | D | NMR (CD$_3$OD) |
|---|---|---|---|---|
| 16-3 | I-16 | Me | I | 8.03 and 7.96(total 1H, s), 5.13(1H, t, J=7 Hz), 4.58 and 4.42(total 1H, m), 4.31 and 4.26 (total 3H, s), 4.20(1H, m), 3.66(2H, m), 3.50 (1H, dd, J=6.6 and 15.6 Hz), 3.25(1H, dd, J=7.4, 15.6Hz), 1.8–2.5(8H, m) |
| 17-3 | I-17 | Et | I | 10.08(1H, s), 8.04 and 7.97(total 1H, s), 5.12 (1H, t, J=7.6Hz), 4.62(2H, q, J=7.2Hz), 4.42 (1H, m), 4.19(1H, m), 3.2–3.7(4H, m), 2.32 (4H, m), 1.98(4H, m), 1.66(3H, t, J=7.2Hz). |
| 18-3 | I-18 | n-Pr | I | 10.08(1H, d, J=2.6Hz), 8.06 and 8.00(total 1H, d, J=2.6Hz), 5.12 and 4.98(total 1H, t, J=7.0Hz), 4.56(2H, t, J=7.8Hz), 4.43(1H, m), 4.20(1H, m), 3.2–3.9(4H, m), 2.34(4H, m), 2.02(6H, m), 1.18 and 1.07(total 3H, t, J=7.4 Hz). |
| 19 | I-19 | n-Bu | I | 10.07(1H, d, J=2.6Hz), 8.06 and 7.99(total 1H, d, J=2.6Hz), 5.12 and 4.99(total 1H, t, J=7.0Hz), 4.59(2H, t, J=7.8Hz), 4.43(1H, m), 4.20(1H, m), 3.2–3.9(4H, m), 2.34(4H, m), 2.02(6H, m), 1.49(2H, m), 1.04(3H, t, J=7.0 Hz). |

TABLE 9

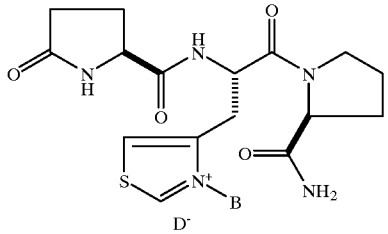

| Example No. | Compound No. | A | X | [α]$_D$ | NMR (CD$_3$OD) |
|---|---|---|---|---|---|
| 20 | I-20 | allyl | Br | | 8.65 (1H, d, J=9.3 Hz), 8.08 (1H, d, J=2.7 Hz), 6.17 (1H, m), 5.47 (2H, m), 5.25 (2H, m), 5.11 (1H, m), 4.41 (1H, dd, J=4.2, 8.8 Hz), 4.19 (1H, dd, J=4.8, 8.8 Hz), 3.66 (2H, m), 3.50 (1H, dd, J=7.2, 15 Hz), 3.25 (1H, m), 1.8–2.5 (8H, m). |
| 21 | I-21 | CH$_2$–Ph | Br | −70.5° (c = 1.005, H$_2$O, 24° C.) | 9.90 and 9.86 (total 1H, d, J=2.4 Hz), 8.12 and 8.03 (total 1H, d, J=2.4 Hz), 7.47 (5H, m), 5.89 (1H, d, J=15.2 Hz), 5.80 (1H, d, J=15.2 Hz), 5.04 (1H, t, J=7 Hz), 4.40 (1H, m), 4.20 (1H, m), 3.1–3.7 (4H, m), 2.35 (4H, m), 1.97 (4H, m). |

TABLE 9-continued

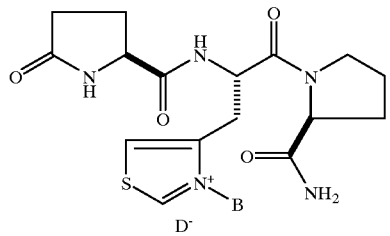

| Example No. | Compound No. | A | X | $[\alpha]_D$ | NMR (CD$_3$OD) |
|---|---|---|---|---|---|
| 22 | I-22 | CH$_2$—C$_6$H$_4$—Me | Br | −65.4° (c = 1.001, H$_2$O, 24° C.) | 9.12 and 8.02 (total 1H, d, J=2.4 Hz), 7.32 (4H, m), 5.82 (1H, d, J=15 Hz), 5.73 (1H, d, J=15 Hz), 5.02 (1H, t, J=7 Hz), 4.40 (1H, m), 4.20 (1H, m), 3.1–3.7 (4H, m), 2.37 (3H, s), 2.34 (4H, m), 1.97 (4H, m). |
| 23 | I-23 | CH$_2$—(2,6-Br$_2$-4-Me-C$_6$H$_2$) | Br | | 9.71 (1H, d, J=2.4 Hz), 7.02 (1H, d, J=2.7 Hz), 5.62 (2H, d, J=4.2), 5.04 (1H, m), 4.42 (1H, m), 4.19 (1H, dd, J=4.2, 8.5 Hz,), 3.66 (2H, m), 3.50 (1H, m), 3.25 (1H, m), 2.22 (6H, s), 1.8–2.5 (8H, m). |

TABLE 10

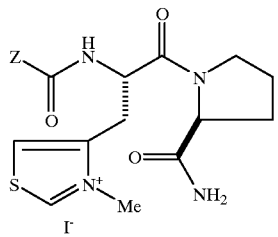

| Example No. | Compound No. | Z | $[\alpha]_D$ | NMR (CD$_3$OD) |
|---|---|---|---|---|
| 24 | I-24 | 1-methyl-2,4-dioxohexahydropyrimidin-6-yl | −26.9° (c = 1.001, H$_2$O, 22.5° C.) | 7.91 and 7.88 (total 1H, s), 5.12 (1H, dd, J=5.1 and 9.9 Hz), 4.44 and 4.55 (total 1H, m), 4.13 and 4.26 (total 1H, m), 4.23 (3H, s), 3.63 (2H, m), 3.48 (1H, dd, J=4.5 and 15.6 Hz), 3.31 (1H, dd, J=9.6 and 15.6 Hz), 3.11 (1H, dd, J=6.9, 16.8 Hz), 3.05 (3H, s), 2.76 (1H, dd), 1.8–2.4 (4H, m). |
| 25 | I-25 | 5-methyl-2-oxo-oxazolidin-4-yl | −42.9° (c = 1.013, H$_2$O, 24.5° C.) | 8.04 and 7.94 (total 1H, s), 5.16 (1H, dd, J=6.4, 7.8 Hz), 4.4–4.6 (2H, m), 4.30 and 4.26 (total 3H, s), 3.98 and 3.90 (total 1H, d, J=5.4 Hz), 3.66 (2H, m), 3.52 (1H, dd, J=6.6, 16.0 Hz), 3.27 (1H, dd, J=8.2, 16 Hz), 1.8–2.4 (4H, m), 1.46 (3H, d, J=6.2 Hz). |

TABLE 10-continued

[Structure shown: Z-NH-CH(CH2-thiazolium-Me)-C(O)-N-pyrrolidine-C(O)NH2, I⁻ counterion]

| Example No. | Compound No. | Z | $[\alpha]_D$ | NMR (CD$_3$OD) |
|---|---|---|---|---|
| 26 | I-26 | [oxazolidinone with Me substituent] | −50.0° (c = 1.006, H$_2$O, 24.5° C.) | 8.09 and 8.02 (total 1H, s), 5.19 (1H, t, J=7 Hz), 4.8–5.0 (1H, m), 4.3–4.5 (2H, m), 4.30 and 4.24 (total 3H, s), 3.82 (1H, m), 3.64 (1H, m), 3.53 (1H, dd, J=7, 15.6 Hz), 3.26 (1H, m), 1.8–2.4 (4H, m), 1.27 (3H, d, J=6.4 Hz). |
| 27 | I-27 | [oxazolidinone] | −59.2° (c = 1.006, H$_2$O, 24.5° C.) | 8.03 and 7.95 (total 1H, s), 5.15 (1H, dd, J=6.4, 7.8 Hz), 4.58 (1H, dd, J=8.4, 9 Hz), 4.42 (1H, dd, J=4.6, 9 Hz), 4.2–4.5 (2 H, m), 4.30 and 4.26 (total 3H, s), 3.67 (2H, m), 3.52 (1H, dd, J=7.4, 15.8 Hz), 3.27 (1H, dd, J=8, 15.8 Hz), 1.8–2.4 (4H, m). |

Example 28

Preparation of 5-[2-L-pyroglutamylamino-2-{(S)-2-carbamoylpyrrolidine-1-ylcarbonyl}ethyl]-3-methylthiazolium iodide (I-28)

The compound (I-28) was obtained 56.4% yield in a manner similar to that, described in the method of Example 16 using the compound (I-3) as a starting material.

$[\alpha]_D$ = −40.6° (c=1.001, MeOH, 21° C.)

IR(KBr)cm$^{-1}$: 3412, 1677, 16:39, 15:3:3, 14:39, 1262.

NMR(CD$_3$OD): 8.20 and 8.21 (total 1H, s), 502 (1H, dd, J=6,7 Hz), 4.41 (1H, dd, J=4,8.4 Hz), 4.25 (1H, dd, J=3, 5.8 Hz), 4.22 (3H, s), 3.68 (2H, m), 3.53 (1H, dd, J=7, 15 Hz), 3.34 (1H, dd, J=6, 15 Hz), 1.8–2.4 (4H, m), 2.02 (4H, m).

Elemental analysis (C$_{17}$H$_{24}$N$_5$O$_4$IS 3H$_2$O) Calcd.: C,35.48; H,5.25; N,12.17; I,22.05; S,5.57. Found: C,35.36; H,5.15; N,12.43; I,21.97; S,5.75. Found: C,35.36; H,5.15; N,12.43; I,21.97; S,5.75.

CbzNHCH$_2$COOH $\xrightarrow{\text{Process 1-i}}$

CbzNHCH$_2$COOR$^6$ $\xrightarrow{\text{Process 1-ii}}$

H$_2$NCH$_2$COOR$^6$ p-TsOH $\xrightarrow{\text{Process 1-iii}}$

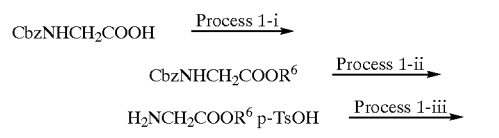

$\xrightarrow{\text{Process 1-iv}}$

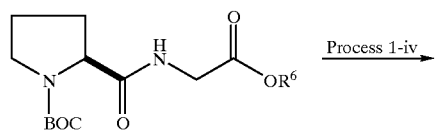

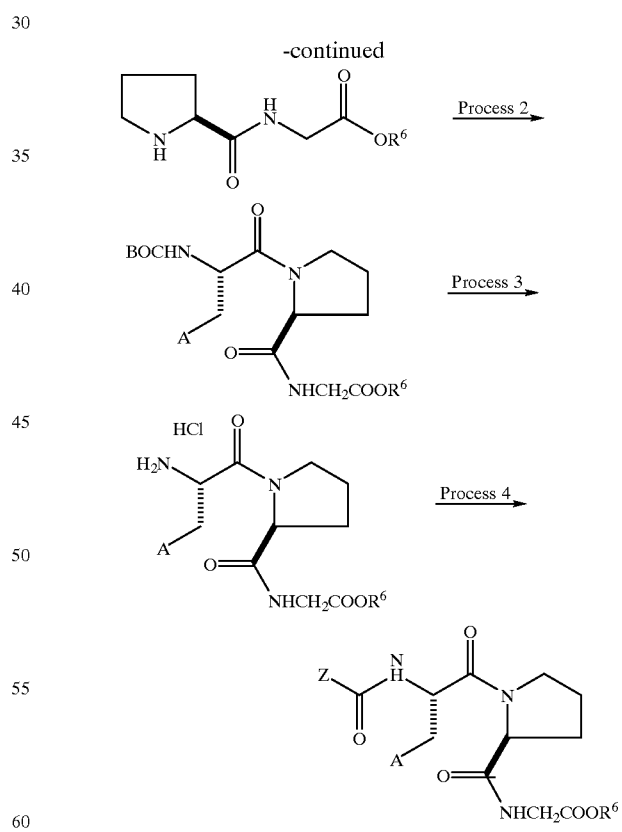

Example 29
Process 1

Preparation of tetradecyl L-prolyl-glycinate (10)
(i) To a solution of N-benzyloxycarbonyl glycine (3 g, 14.3 mmol), tetradecylalcohol (3.07 g, 14.3 mmol) an N,N- dimethylaminopyridine (87 mg, 10.3 mmol) in ethyl acetate (100 ml) was added DCC (2.98 g, 2.34 mmol) and the resulting mixture was stirred for 2 h at room temperature. After the precipitation which appeared was filtered off, the filtrate was concentrated in vacuo. The residue was washed with ethanol to give N-benzyloxycarbonylglycine tetradecyl ester (7) (3.46 g, 59.5%) as crystal.

mp: 57–58° C.

NMR(CDCl$_3$): 7.36 (5H, s), 5.22 (1H, m), 5.13 (2H, s), 4.14 (2H, t, J=6.6 Hz), 3.84 (2H, d, J=5.4 Hz), 1.60 (2H, m), 1.26 (22H, br.s), 0.88 (3H, t, J=6.6 Hz).

Elemental analysis (C$_{24}$H$_{39}$NO$_4$) Calcd.: C,71.07; H,9.69; N,3.45. Found: C,70.94; H,9.60; N,3.74.

(ii) A solution of the compound (7) and p-toluenesulfonic acid hydrate (1.4 g, 7.39 mmol) in mixed solvents of water (2 ml)-methanol (70 ml) was hydrogenated using 5% pd/C (500 mg) for 3 h at room temperature. After the catalyst was filtered off, the filtrate was concentrated in vacuo. The residue was recrystallized from ethyl acetate to give tetradecanylglycinate p-toluensulfonate (8) (2.76 g, 84%).

mp: 85.5–86.56° C.

NMR(CD$_3$OD): 7.70 (2H, d, J=8.2 Hz), 7.23 (2H, d, J=8.2 Hz), 4.23 (2H, d, J=6.6 Hz), 3.82 (2H, s), 2.37 (3H, s), 1.65 (2H, m), 1.29 (22H, m), 0.90 (3H, t, J=6.6 Hz).

Elemental analysis (C$_{23}$H$_{41}$NSO$_5$) Calcd.: C,62.12; H,9.29; N,3.15; S,7.21. Found: C,61.90; H,9.15; N,3.18; S,7.72.

(iii) To a solution of the compound (8) (2.06 g, 4.64 mmol), N-(tert-butyloxycarbonyl)-L-proline (1 g, 4.64 mmol), N-hydroxybenzotriazole (18 mg, 0.139 mmol), and triethylamine (0.71 ml) in N,N-dimethylformamide (30 ml) was added DCC (1 g, 4.87 mmol) and the resulting mixture was stirred for 18 h at room temperature. After the precipitation which appeared was filtered off. the filtrate was concentrated in vacuo. The residue was partitioned between water and ethyl acetate. The organic layer was washed with water, dried over magnesium sulphate, and concentrated in vacuo. The residue was subjected to silica gel column chromatography (toluene: ethyl acetate=3:1) to give tetradecyl N-(tert-butyloxycarbonyl)-L-prolyl-glycinate (9) (1.94 g, 89.4%).

[α]$_D$=−54.4° (c=1.008, CHCl$_3$, 23° C.)

NMR(CDCl$_3$): 4.31 (1H, m), 4.13 (2H, t, J=6.6 Hz), 4.05 (2H, dd, J=5.8, 7.7 Hz), 3.45 (2H, m), 1.90 (2H, m), 1.47 (9H, s), 1.26 (22H, br.s), 0.88 (3H, t, J=7 Hz).

Elemental analysis (C$_{26}$H$_{48}$N$_2$O$_5$) Calcd.: C,66.63; H,10.32; N,5.98. Found: C,66.62; H, 10.24; N,6.05.

(iv) A suspension of the compound (9) (1.47 g, 3.02 mmol) in trifluoroacetic acid (14 ml) was stirred for 2 h under ice-cooling. The reaction mixture was diluted with toluene and the resulting mixture was concentrated in vacuo. The residue was partitioned between ethyl acetate and sodium hydrogencarbonate aq. The organic layer was washed with water and concentrated in vacuo to give 1.08 g of tetradecyl L-prolyl-glycinate (10) as powder.

The compounds (11) and (12) were synthesized in a manner similar to that described in the above method. The results were shown in Table 11.

TABLE 11

| Example No. | Compound No. | R$^6$ | [α]$_D$ | NMR |
|---|---|---|---|---|
| 29-1 | 10 | (CH$_2$)$_{13}$CH$_3$ | −45.7° (c = 1.004, MeOH, 23° C.) | (CDCl$_3$) 8.10 (1H, m), 4.13 (2H, t, J=6.6 Hz), 4.03 (2H, d, J=5.6 Hz), 3.79 (1H, dd, J=5.4, 9 Hz), 3.00 (2H, m), 1.8–2.2 (2H, m), 1.70 (4H, m), 1.26 (22H, m), 0.88 (3H, t, J=6.8 Hz). |
| 30-1 | 11 | CH (CH$_3$)$_2$ | | (CD$_3$OD) 7.36 (5H, s), 5.18 (1H, d, J=7 Hz), 4.31 (1H, m), 4.08 (2H, m), 3.35 (2H, m), 2.44 (1H, m), 2.05 (3H, m) |
| 31-1 | 12 | CH$_2$Ph | | (CD$_3$OD) 5.03 (1H, m), 4.33 (1H, m), 4.00 (2H, m), 3.35 (2H, m), 2.48 (1H, m), 2.06 (3H, m), 1.24 (6H, d, J=6 Hz) |

Example 29

Process 2

Preparation of tetradecyl N-(tert-butyloxycarbonyl)-3-(4-thiazolyl)-L-alanyl-L-prolyl-glycinate (13)

To a solution of N-(tert-butoxycarbonyl)-3-(4-thiazolyl)-L-alanine (1, 480 mg, 1.76 mmol) which was synthesized in accordance with the method described in the literature (Synthtic Commun., 20, 3507, (1990)), the compound (10) (650 mg, 1.76 mmol), and N-hydroxybenzotriazole (70 mg, 0.528 mmol) in N,N-dimethylformamide (20 ml) was added DCC (380 mg, 1.848 mmol) and the resulting mixture was stirred overnight at room temperature. After the precipitation which appeared was filtered off, the filtrate was concentrated in vacuo. The residue was dissolved in ethyl acetate and the precipitation which appeared was filtered off again. The filtrate was concentrated in vacuo. The residue was subjected to silica gel column chromatography (ethyl acetate:toluene=9:1) to give 1.02 g of the compound (13).

The compounds (14) and (15) were synthesized in a manner similar to that described in the above method. The results were shown in Table 12.

TABLE 12

| Example No. | Compound No. | $R^6$ | $[\alpha]_D$ | NMR (CDCl$_3$) |
|---|---|---|---|---|
| 29-2 | 13 | (CH$_2$)$_{13}$CH$_3$ | −44.9° (c = 1.012, CHCl$_3$, 23° C.) | 8.78 (1H, d, J=1.8 Hz), 7.22 (1H, d, J=2 Hz), 5.54 (1H, d, J=8.2 Hz), 4.67 (2H, m), 4.41 (1H, dd, J=7.4, 17.6 Hz), 4.14 (2H, t, J=7 Hz), 3.74 (1H, dd, J=5.5, 17.6 Hz), 3.50 (1H, m), 3.30 (2H, m), 2.97 (1H, m), 1.45 (9H, s), 2.30 (1H, m), 1.95 (3H, m), 1.27 (22H, m), 0.89 (3H, t, J=6.6 Hz). |
| 30-2 | 14 | CH (CH$_3$)$_2$ | −43.2° (c = 1.012, CHCl$_3$, 23° C.) | 8.80 (1H, s), 8.60 (1H, m), 7.22 (1H, s), 5.78 (1H, m), 5.07 (1H, m, COOCH), 4.64 (2H, m), 1.45 (9H, s), 1.29 (3H, d, J=6 Hz), 1.27 (3H, d, J=6Hz) |
| 31-2 | 15 | CH$_2$Ph | −49.4° (c = 1.01, CHCl$_3$, 23° C.) | 8.58 (1H, d, J=2 Hz), 7.36 (5H, s), 7.18 (1H, d, J=1.8 Hz), 5.50 (1H, d, J=6.8 Hz), 4.64 (2H, m), 4.47 (1H, dd, J=6.8, 17.5 Hz), 3.77 (1H, dd, J=5, 17.5 Hz), 3.50 (1H, m), 3.30 (2H, m), 2.95 (1H, m), 2.2–1.7 (4H, m), 1.44 (9H, s) |

Example 29

Process 3

Preparation of tetradecyl 3-(4-thiazolyl)-L-alanyl-L-prolyl-glycinate hydrochloride (16)

To a solution of the compound (13) (1.2 g, 1.92 mmol) in ethyl acetate (20 ml) was added the solution of 4N-hydrogen chloride in ethyl acetate (20 ml) under ice-cooling and the resulting mixture was stirred for 2 h at the same temperature. The reaction mixture was concentrated in vacuo to give the compound (16) (1.27 g, quantitative). This compound used in the next, reaction without purification.

Example 30

Process 3

Preparation of isopropyl 3-(4-thiazolyl)-L-alanyl-L-prolyl-glycinate hydrochloride (17)

In a manner similar to that described in the method of Example 29-3, the compound (17) (590 mg, quantitative) was obtained by de-tert-butoxycarbonylation of compound (14) (580 mg, 1.24 mmol). This compound was used in the next reaction without purification.

Example 31

Process 3

Preparation of benzyl 3-(4-thiazolyl)-L-alanyl-L-prolyl-glycinate hydrochloride (18)

In a manner similar to that described in the method of Example 29-3, the compound (18) (700 mg, quantitative)- was obtained by de-tert-butoxycarbonylation of the compound (15) (750 mg, 1.45 mmol). This compound was used in the next, reaction without purification.

Example 29

Process 4

Preparation of tetradecyl cis-L-5-methyl-2-oxo-oxazolidine-4-ylcarbonyl-3-(4-thiazolyl)-L-alanyl-L-prolyl-glycinate (I-29)

Cis-5-methyl-2-oxazolidine-4-yl carboxylic acid (139 mg, 0.96 mmol), which was synthesized in accordance with the method described in Chem. Lett., 1982. 1171. and N-hydroxysuccinimide (110 mg, 0.96 mmol) were dissolved in N, N-dimethylformamide (2 ml). To this solution was added DCC (200 mg, 0.97 mmol) and the resulting mixture was stirred for 2 h at, room temperature. To the reaction mixture was added the free base of the compound (16) prepared by filtering off the salt which was precipitated by adding triethylamine (0.53 ml, 3.8 mmol) to the solution of the compound (16) (635 mg, 0.96 mmol) in N,N-dimethylformamide (15 ml) under ice-cooling. The reaction mixture was stirred for 72 h at room temperature. After the precipitation which appeared was filtered off and the filtrate was concentrated in vacuo. Mixed solvents of methanol:water=3:1 was added to the residue and the precipitation which appeared was filtered off. The filtrate was subjected to gel filtration column chromatography (MCI Gel CHP 20P 200 ml, methanol-water) and successively to silica gel column chromatography (chloroform:methanol=7:1) to give 381 mg of the compound (I-29).

The compounds (I-30) and (I-31) was synthesized in a manner similar to that described in the above method. The results were shown in Table 13.

Example 32

Preparation of cis-L-5-methyl-2-oxo-oxazolidine-4-ylcarbonyl-3-(4-thiazolyl)-L-alanyl-L-prolyl-glycine (I-32)

To a solution of the compound (I-31) (500 mg, 0.919 mmol) in mixed solvents of methanol (20 ml)-water (20 ml) was added lithium hydroxide (193 mg, 4.56 mmol) and the resulting mixture was stirred for 30 min at room temperature. After the reaction mixture was neutralized by adding the diluted hydrochloric acid, the mixture was concentrated in vacuo. The residue was subjected to gel filtration column chromatography (MCI Gel CHP 20P, 200 ml, methanol-water) and further lyophilized to give 218 mg of the compound (I-32). The result was shown in Table 13.

TABLE 13

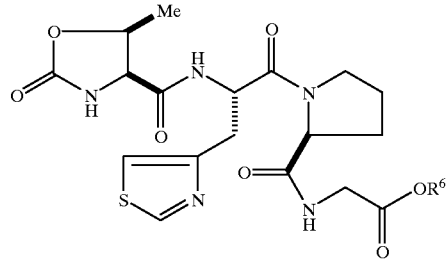

| Example No. | Compound No. | $R^6$ | $[\alpha]_D$ | NMR (CD$_3$OD) |
|---|---|---|---|---|
| 29-4 | I-29 | (CH$_2$)$_{13}$CH$_3$ | −54.7° (c = 0.505, MeOH, 23° C.) | 8.95 (1H, d, J=1.2 Hz), 8.58 (2H, m), 7.45 (1H, s), 4.90 (2H, m), 4.49 (1H, m), 4.34 (1H, d, J=8.6 Hz), 4.14 (2H, t, J=6.6 Hz), 3.96 (2H, d), 3.87 (1H, m), 3.30 (3H, m), 1.28 (3H, d, J=6.6 Hz), 0.89 (3H, t, J=6.6 Hz). |
| 30-4 | I-30 | CH(CH$_3$)$_2$ | −68.7° (c = 0.504, MeOH, 25° C.) | 8.78 (1H, d, J=1.8 Hz), 7.22 (1H, d, J=2 Hz), 5.54 (1H, d, J=8.2 Hz), 4.67 (2H, m), 4.41 (1H, dd, J=7.4, 17.6 Hz), 4.14 (2H, t, J=7 Hz), 3.74 (1H, dd, J=5.5, 17.6 Hz), 3.50 (1H, m), 3.30 (2H, m), 2.97 (1H, m), 1.45 (9H, s), 2.30 (1H, m), 1.95 (3H, m), 1.27 (22H, m), 0.89 (3H, t, J=6.6 Hz). |
| 31-4 | I-31 | CH$_2$Ph | −61.8° (c = 0.508, MeOH, 23° C.) | 8.88 (1H, s), 7.42 (1H, s), 7.35 (5H, m), 5.18 (2H, s), 4.95 (2H, m), 4.47 (1H, dd, J=4.2, 8.6 Hz), 4.33 (1H, d, J=8.7 Hz), 4.07 (1H, d, J=17.7 Hz), 3.99 (1H, d, J=17.7 Hz), 3.80 (1H, m), 3.60 (1H, dd, J=6.9, 14 Hz), 3.35 (1H, m), 3.22 (1H, m), 2.2–1.9 (4H, m), 1.21 (3H, d, J=6.6 Hz) |
| 32 | I-32 | H | −69.2° (c = 0.507, H$_2$O, 22.5° C.) | 8.99 (1H, d, J=1.4 Hz), 7.44 (1H, d, J=1.4 Hz), 4.95 (2H, m), 4.47 (1H, t, J=5.4 Hz), 4.34 (1H, d, J=8.8 Hz), 3.87 (1H, d, J=17.2 Hz), 3.67 (1H, d, J=17.2 Hz), 3.80–3.20 (4H, m), 2.2–1.8 (4H, m), 1.21 (3H, d, J=6.2 Hz) |

Example 33

Preparation of tetradecyl L-pyroglutamyl-3-(4-thiazolyl)-L-alanyl-L-prolyl-glycinate (I-33)

In a manner similar to that described in the method of Example 29-4, N-hydroxysuccinimide ester of L-pyroglutamic acid which are prepared by the reaction of L-pyroglutamic acid (124 mg, 0.96 mmol), N-hydroxysuccinimide (110 mg, 0.96 mmol), and DCC (200 mg, 0.97 mmol) was reacted with the free base of the compound (16) which was prepared by the compound (16) (635 mg, 0.96 mmol) and triethylamine (0.53 ml, 3.84 mmol) to give 497 mg (81.7%) of the compound (I-33).

$[\alpha]_D = -52.4°$ (c=0.508, MeOH, 23° C.)

NMR(CD$_3$OD): 8.95 (1H, d, J=2.1 Hz), 7.44 (1H, d, J=2.1 Hz), 4.92 (1H, t, J=6.9 Hz), 4.49 (1H, dd, J=3.6, 8.5 Hz), 4.14 (3H, m), 3.97 (2H, s), 3.75 (1H, m), 3.40 (1H, m), 3.20 (2H, m), 2.4–1.8 (8H, m), 1.62 (2H, m), 1.32 (22H, m), 0.89 (3H, t, J=6.9 Hz).

Elemental analysis (C$_{32}$H$_{51}$N$_5$O$_6$S 0.4H$_2$O)

Calcd.: C,59.96; H,8.14; N,10.92; S,5.00. Found: C,59.97; H,8.18; N,11.02; S,5.07.

Example 34
Process 1

Preparation of benzyl cis-L-3-ethoxycarbonyl-5-methyl-2-oxo-oxazolidine-4-carboxylate (19)

A solution of cis-5-methyl-2-oxo-oxazolidine-4-carboxylic acid benzyl ester (706 mg, 3 mmol) which was synthesized in accordance with the method described in Chem. Lett., 1982, 1171 in tetrahydrofuran (12 ml) was cooled in a dry ice-acetone bath (−50° C.) under nitrogen atmosphere. To the solution was added potassium tert-butoxide (337 mg, 3 mmol) and the resulting mixture was stirred for 20 min. at the same temperature. To the mixture was added dropwise a solution of ethyl chlorocarbonate (0.46 ml, 4.83 mmol) in tetrahydrofuran (2 ml) over 10 min. The reaction mixture was stirred for 3 h at −50 to −14° C.(bath temperature). The reaction mixture was partitioned between ice-water and ethyl acetate. The organic layer was washed with water, dried over magnesium sulfate, and concentrated in vacuo. The residue was subjected to Lober® column (Merck inc.) and recrystallized from diethyl ether-hexane to give 847 mg of the compound (19) as colorless needle crystal.

Example 34
Process 2 preparation of cis-L-3-ethoxycarbonyl-5-methyl-2-oxo-oxazolidine-4-carboxylic acid (20)

A solution of the compound (19) (718 mg, 2.34 mmol) in 50% aqueous methanol (3 ml) was hydrogenated using 5% Pd/C (200 mg) for 2 h at room temperature. The catalyst was filtered off and the filtrate was concentrated in vacuo to give 516 mg of compound (20) as powder.

Example 35
Process 1

Preparation of benzyl cis-L-3-pivaloyloxymethyl-5-methyl-2-oxo-oxazolidine-4-carboxylate (21)

In a manner similar to that described in the method of Example 34-1, cis-L-5-methyl-2-oxo-oxazolidine-4-carboxylic acid benzyl ester (706 mg, 3 mmol) was pivaloyloxymethylatied with pivalic acid iodomethyl (1.19 g, 4.92 mmol) in the presence of potassium tert-butoxide (337 mg, 3 mmol) in tetrahydrofuran (12 ml) to give 893 mg of the compound (21) as colorless needle crystal.

Example 35
Process 2

Preparation of benzyl cis-L-3-pivaloyloxymethyl-5-methyl-2-oxo-oxazolidine-4-carboxylic acid (22)

In a manner similar to that described in the method of Example 34-2, the compound (21) (892 mg, 2.55 mmol) was de-benzylesterificated by hydrogenating in the presence of 5% Pd/C (250 mg) in aqueous methanol to give 642 mg of the compound (22) as colorless needle crystal.

Example 36
Process 1

Preparation of cis-L-5-methyl-N-(4-morpholinylcarbonylmethyl)-2-oxo-oxazolidine-4-carboxylic acid benzyl ester (23)

In a manner similar to that described in the method of Example 34-1, to a solution of cis-L-5-methyl-2-oxo-oxazolidine-4-carboxylic acid benzyl ester (706 mg, 3 mmol) in THF (14 ml) was added potassium tert-butoxide (337 mg, 3 mmol) at −53° C. in nitrogen atmosphere and the resulting mixture was stirred for 20 min. at the same temperature. To the reaction mixture was added a solution of N-iodoacetylmorpholine (1.15 g, 4.51 mmol) in THF (1 ml) and the resulting mixture was stirred for 4 h at −53° C. to −15° C. The reaction mixture was partitioned between ethyl acetate and cooled sodium thiosulfate aq. The organic layer was washed with water, dried over magnesium sulfate, and concentrated in vacuo. The residue was subjected to Lobar® column (Merck inc.) and the fractions eluting with toluene:acetone=5:1 were collected to yield the compound (23) (873 mg) as crystal.

Example 36
Process 2

Preparation of cis-L-5-methyl-N-(4-morpholinylcarbonylmethyl)-2-oxo-oxazolidine-4-carboxylic acid (24)

In a manner similar to that, described in the method of Example 34-2, the compound (23) (846 mg, 2.33 mmol) was de-benzylesterificated by hydrogenating in the presence of 5% Pd/C (250 mg) in aqueous methanol to give 740 mg of the compound (24) as colorless needle crystal.

Example 37
Process 1

Preparation of cis-L-5-methyl-N-(4-morpholinocarbonyl)-2-oxo-oxazolidine-4-carboxylic acid benzylester (25)

In a manner similar to that described in the method of Example 34-1, cis-L-5-methyl-2-oxo-oxazolidine-4-carboxylic acid benzyl ester (470 mg, 2 mmol) was reacted with 4-morpholine-carbonylchloride (0.35 ml, 3 mmol) in the presence of potassium tert-butoxide (224 mg, 2 mmol) in THF to give 630 mg of the compound (25).

Example 37
Process 2

Preparation of cis-L-5-methyl-N-(4-morpholinocarbonyl)-2-oxo-oxazolidine-4-carboxylic acid (26)

In a manner similar to that described in the method of Example 34-2, the compound (25) (1.08 g, 3.10 mmol) was de-benzylesterificated by hydrogenating in the presence of 5% Pd/C (200 mg) in aqueous methanol to give 706 mg of the compound (26).

Example 38
Process 1

Preparation of cis-L-5-methyl-N-(4-oxo-butyl)-2-oxo-oxazolidine-4-carboxylic acid benzyl ester (27)

In a manner similar to that described in the method of Example 34-1, cis-L-5-methyl-2-oxo-oxazolidine-4-carboxylic acid benzyl ester (3 g, 12.9 mmol) was reacted with 1-iodo-2-butanone (3.83 g, 19.3 mmol) in the presence of potassium tert-butoxide (1.45 g, 12.9 mmol) in THF to give 2.15 g of the compound (27).

Example 38
Process 2

Preparation of cis-L-5-methyl-N-(2-oxo-butyl)-2-oxo-oxazolidine-4-carboxylic acid (28)

In a manner similar to that described in the method of Example 34-2, the compound (27) (1.67 g, 5.47 mmol) was de-benzylesterificated by hydrogenating in the presence of 5% Pd/C (480 mg) in aqueous methanol to give 0.65 g of the compound (28). The above results were shown in Tables 14 and 15.

TABLE 14

| Example No. | Compound No. | $R^3$ | $R^7$ | $[\alpha]_D$ | NMR |
|---|---|---|---|---|---|
| 34-1 | 19 | COOEt | Bzl | −63.1° (c = 1.015, CHCl$_3$, 23° C.) | (CDCl$_3$): 7.37 (5H, bs), 5.29 (1H, d, J=12 Hz), 5.22 (1H, d, J=12 Hz), 4.79 (2H, m), 4.26 and 4.25 (2H, q, J=7.2 Hz), 1.30 (3H, d, J=6 Hz), 1.25 (3H, t, J=7.2 Hz). |
| 34-2 | 20 | COOEt | H |  | (DMSO-d$_6$): 4.93 (1H, m), 4.76 (1H, d, J=8.4 Hz), 4.21 (2H, m), 1.30 (3H, d, J=6.3 Hz), 1.22 (3H, t, J=7.2 Hz). |
| 35-1 | 21 | CH$_2$OC(O)—CMe$_3$ | Bzl | −41.1° (c = 1.003, CHCl$_3$, 22° C.) | (CDCl$_3$): 7.38 (5H, s), 5.43 (1H, d, J=11.2 Hz), 5.30 (1H, d, J=12 Hz), 5.24 (1H, d, J=11,2 Hz), 5.20 (1H, d, J=12 Hz), 4.79 (1H, m), 4.58 (1H, d, J=8.8 Hz), 1.23 (3H, d, J=6.4 Hz), 1.20 (9H, s). |
| 35-2 | 22 | CH$_2$OC(O)—CMe$_3$ | H | −32.0° (c = 1.007, MeOH, 22° C.) | (DMSO-d$_6$): 5.31 (1H, d,J=11 Hz, 5.17 (1H, d, J=11 Hz), 4.89 (1H, dq, J=8.6, 6.8 Hz), 4.48 (1H, d, J=8.6 Hz), 1.26 (3H, d, J=6.8 Hz), 1.14 (9H, s). |
| 36-1 | 23 | H$_2$C—C(O)—N(morpholine) | Bzl | −112.1° (c = 1.009, MeOH, 25° C.) | (CDCl$_3$): 7.38 (5H, s), 5.29 (1H, d, J=12 Hz), 5.15 (1H, d, J=12 Hz), 4.90 (2H, m), 4.55 (1H, d), 3.74 (1H, d) 3.3–3.7 (8H, m), 1.26 (3H, m) |

TABLE 15

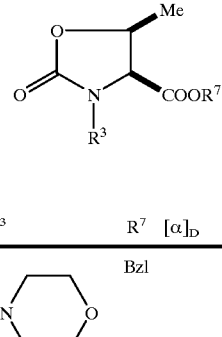

| Example No. | Compound No. | R³ | R⁷ | [α]_D | NMR |
|---|---|---|---|---|---|
| 36-2 | 24 | 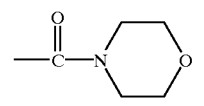 | Bzl | | (CDCl₃): 5.01 (1H, dq, J=6.4, 9.0 Hz), 4.62 (1H, d, J=9 Hz), 4.46 (1H, d, J=17.2 Hz), 3.95 (1H, d, J=17.2 Hz), 3.4–3.8 (8H, m), 1.39 (3H, d, J=6.4 Hz) |
| 37-1 | 25 | 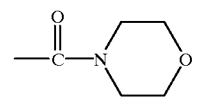 | Bzl | −68.4° (c = 1.012, CHCl₃, 25° C.) | (CDCl₃): 7.37 (5H, s), 5.30 (1H, d, J=11.6 Hz), 5.15 (1H, d, J=11.6 Hz), 5.00 (1H, d, J=8.6 Hz), 4.89 (1H, m), 3.8–3.4 (8H, m), 1.26 (3H, d, J=6.4 Hz) |
| 37-2 | 26 | 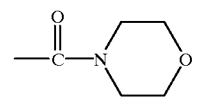 | H | −48.8° (c = 0.510, MeOH, 26° C.) | (CD₃OD): 4.99 (1H, m), 4.87 (1H, d, J=6 Hz), 3.72 (4H, m), 3.54 (4H, m), 1.38 (3H, d, J=6 Hz) |
| 38-1 | 27 | 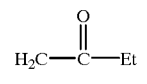 | Bzl | −129.5° (c = 1.018, CHCl₃, 26° C.) | (CDCl₃): 7.37 (5H, s), 5.20 (2H, dd, J=11.6 Hz), 4.91 (1H, m), 4.73 (1H, d, J=9 Hz), 4.54 (1H, d, J=19.2 Hz), 3.79 (1H, d, J=19.2 Hz), 2.41 (2H, dq, J=2, 7.4 Hz), 1.06 (3H, t, J=7.4 Hz) |
| 38-2 | 28 | 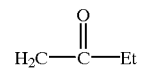 | H | −110.3° (c = 1.006, MeOH, 26° C.) | (CDCl₃): 4.98 (1H, m), 4.70 (1H, J=9 Hz), 4.52 (1H, d, J=18.8 Hz), 3.91 (1H, d, J=18.8 Hz), 2.47 (2H, q, J=7.4 Hz), 1.44 (3H, d, J=6.6 Hz), 1.09 (3H, t, J=7.4 Hz) |

Example 34

Process 3

Preparation of cis-L-3-ethoxycarbonyl-5-methyl-2-oxo-oxazolidine-4-yl-carbonyl-3-(4-thiazolyl)-L-alanyl-L-prolineamide (I-34)

To the compound (20) (236 mg, 1.08 mmol) was added oxalyl chloride (0.15 ml, 1.72 mmol) and N,N-dimethylformamide (2 drops) and the resulting mixture was stirred for 2.5 h. The reaction mixture was concentrated in vacuo. The residue was dissolved in tetrahydrofuran (3 ml) and to the solution was added a solution of 3-(4-thiazolyl)-L-alanyl-L-prolineamide (6,688 mg, 1.2 mmol) and triethylamine (0.61 ml, 4.35 mmol) in N,N-dimethylformamide (9 ml) under ice-cooling with stirring. The reaction mixture was stirred overnight at room temperature. After the percipitation was filtered off, the filtrate was concentrated in vacuo. After the residue was dissolved in water and the solution was subjected to gel filtration column chromatography (MCI Gel CHP-20P, 200 ml, methanol-water) to give the crude compound (248 mg). The crude compound was subjected to silica gel column chromatography (chloroform:methanol=9:1) to give 188 mg of the compound (I-34).

The compound (I-35) to (I-39) were synthesized in a manner similar to that described in the above method. The results were shown in Tables 16 and 17. When the compounds I-36, 38, and 39 were synthesized, DCC was used instead of oxalyl chloride as an activating agent.

TABLE 16

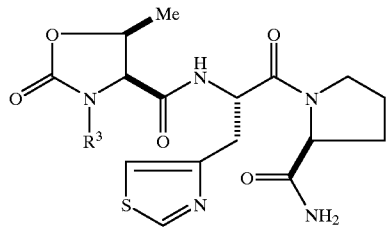

| Example No. | Compound No. | R³ | mp (° C.) | [α]_D | NMR |
|---|---|---|---|---|---|
| 34-3 | I-34 | COOEt | 126–130 | −94.5° (c = 0.511, H₂O, 23° C.) | (CD₃OD): 8.97 and 8.96 (total 1H, d, J=2.1 Hz), 7.45 and 7.38 (total 1H, d, J=2.1 Hz), 5.01 (1H, t, J=6.9 Hz), 4.84 (1H, m), 4.78 (1H, d, J=8.4 Hz), 4.41 (1H, dd, J=4.2, 8.7 Hz), 4.20 (2H, q, J=7.2 Hz), 3.88 (1H, m), 3.48 (1H, m), 3.40 (1H, dd, J=6.9, 14.7 Hz), 3.20 (1H, dd, J=7.2, 14.7 Hz), 2.19 (1H, m), 1.99 (3H, m), 1.37 and 1.30 (total 3H, d, J=6.3 Hz), 1.25 and 1.20 (total 3H, t, J=7.2 Hz). |
| 35-3 | I-35 | CH₂OC(O)—CMe₃ | 212–213 | −66.3° (c = 0.514, MeOH, 22.5° C.) | (CD₃OD): 8.97 and 8.94 (total 1H, d, J=2.1 Hz), 7.48 and 7.40 (total 1H, d, J=2.1 Hz), 5.33 and 5.31 (total 1H, d, J=11.1 Hz), 5.03 (1H, t, J=6.9 Hz), 5.01 and 4.96 (total 1H, d, J=11.1 Hz), 4.84 (1H, m), 4.58 and 4.54 (total 1H, d, J=8.7 Hz), 4.41 and 4.32 (1H, dd, J=3.9, 8.1 Hz), 3.89 (1H, m), 3.52 (1H, m), 3.41 (1H, dd, J=6.6, 14.7 Hz), 3.22 (total 1H, dd, J=7.2, 14.7 Hz), 2.29 (1H, m), 2.00 (3H, m), 1.30 and 1.25 (total 3H, d, J=6.6 Hz), 1.21 and 1.96 (total 9H, s). |

TABLE 17

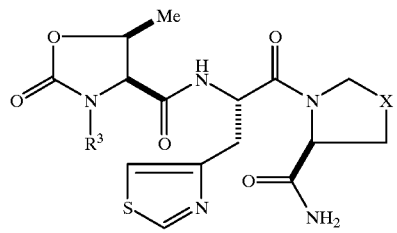

| Example No. | Compound No. | R³ | X | [α]_D | NMR |
|---|---|---|---|---|---|
| 36-3 | I-36 | H₂C—C(=O)—N(morpholine) | CH₂ | −79.1° (c = 1.004, H₂O, 25° C.) | (CD₃OD): 8.98 and 8.96 (total 1H, d, J=2 Hz), 7.46 and 7.37 (total 1H, d, J=2 Hz), 4.9–5.1 (2H, m), 4.53 and 4.52 (total 1H, d, J=9 Hz), 4.40 (1H, 4.36 (1H, d, J17.2 Hz), 3.86 (1H, m), 3.86 (1H, d, J17.2 Hz), 3.3–3.7 (10H, m), 3.18(1H, dd, J=7.8, 14.4 Hz), 1.8–2.3 (4H, m), 12.4 and 1.17 (total 3H, d, J=6.4Hz) |

TABLE 17-continued

| Example No. | Compound No. | R³ | X | [α]_D | NMR |
|---|---|---|---|---|---|
| 37-3 | I-37 | —C(=O)—N(morpholine) | CH₂ | −69.7° (c = 0.505, MeOH, 26° C.) | (CD₃OD): 8.93 and 8.72 (total 1H, d, J=1.8 Hz), 7.48 and 7.39 (total 1H, d, J=1.8 Hz), 4.9–5.1 (3H, m), 4.42 (1H, dd, J=4.4, 8.4 Hz), 3.85 (1H, m), 3.70 (4H, m), 3.50 (4H, m), 1.8–2.3 (4H, m) 1.28 (3H, d, J=5.8 Hz) |
| 38-3 | I-38 | H₂C—C(=O)—Et | CH₂ | −80.4° (c = 1.012, MeOH, 26° C.) | (CD₃OD): 8.96 and 8.98 (total 1H, d, J=2.1 Hz), 7.35 and 7.43 (total 1H, d, J=2.1 Hz), 5.02 (1H, dd, J=6.6 Hz), 4.92 (1H, m), 4.48 and 4.49 (toal 1H, d, J=4.4, 8.4 Hz), 4.40 (1H, dd, J=4.2, 8.4 Hz), 4.34 (1H, d, J=18.6 Hz), 3.76 (1H, d, J=18.6 Hz), 3.85 (1H, m), 3.51 (1H, m), 3.38 (1H, dd, J=6.6, 14.9 Hz), 3.17 (1H, dd, J=6.6, 14.9 Hz), 2.48 (2H, m), 1.80–2.30 (4H, m), 1.26 (3H, d, J=6.9 Hz), 1.21 (3H, d, J=6.9 Hz), 1.06 (3H, t, J=1.78 Hz), 1.05 (3H, t, J=4.8 Hz) |
| 39-3 | I-39 | H₂C—C(=O)—N(morpholine) | S | −103.9° (c = 1.004, H₂O, 25° C.) | (CD₃OD): 8.97 (1H, d, J=2 Hz), 7.47 and 7.42 (total 1H, d, J=2 Hz), 4.8–5.2 (4H, m), 4.4–4.62 (4H, m), 437(1H, d, J=17.2 Hz), 3.86 (1H, d, J17.2 Hz), 3.67 (4H, m), 3.50 (4H, m), 3.1–3.4 (4H, m), 1.19 (3H, d, J=6.6 Hz) |

Example 40

Preparation of cis-L-3-morpholinomethyl-5-methyl-2-oxo-oxazolidine-4-yl-carbonyl-3-(4-thiazolyl)-L-alanyl-L-prolineamide (I-40)

To a ethanol (3.6 ml) solution of the compound (I-10) (237 mg, 0.6 mmol) was added morpholine (180 mg, 2.07 mmol) and 37% formalin (0.22 ml) and the resulting mixture was stirred for 3 h on oil bath (60° C.). The reaction mixture was concentrated in vacuo. The residue was dissolved in a mixed solvents of chloroform and methanol and the solution was subjected to alumina column chromatography (chloroform:methanol=973) to give the fractions containing the aimed compound (258 mg). The fractions were dissolved in methanol and a large amount of diethyl ether was added to the solution. The precipitation which appeared was filtered off to give 195 mg of the compound (I-40).

The compound (I-41) was synthesized in a manner similar to that described in the above method. The results were shown in Table 18.

Example 42

Preparation of cis-L-3-(N-methylpiperazinyl)methyl-5-methyl-2-oxo-oxazolidine-4-yl-carbonyl-3-(4-thiazolyl)-L-alanyl-L-prolineamide hydrochrolide (I-43)

i) In a manner similar to that described in the method of Example 40, the compound (I-10) (395 mg, 1 mmol) was treated with N-methylpiperazine (0.2 ml, 2.34 mmol) and 37% formalin (0.24 ml) in ethanol (10 ml) to form Mannich base, giving 350 mg of the compound (I-42) which was free base of the compound (I-43).

The detailed date was shown in Table 18.

ii) After the compound (I-42) (120 mg, 0.244 mmol) was dissolved in methanol (1 ml), to this solution was added a solution 4N hydrogen chloride in ethyl acetate (0.15 ml). Subsequently, to the mixture was added diethyl ether and the precipitation which appeared was filtered off to give 138 mg of the compound (I-43).

[α]_D=−82° (c=0.51, H₂O, 23° C.)

IR(KBr)cm⁻¹: 3412, 1764, 1677, 1647, 1544, 1446, 1342, 1298, 1221.

Elemental analysis (C₂₂H₃₂N₆O₅S 1.8HCl 0.3Et₂O 1.2H₂O) Calcd.: C,46.28; H,6.56; N,13.96; Cl,10.60; S,5.33. Found: C,46.08; H,6.38; N,14.27; Cl,10.88; S,5.37.

TABLE 18

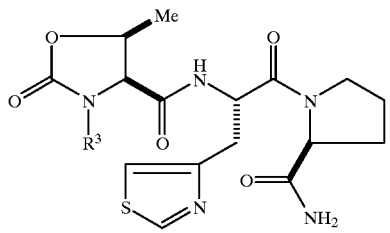

| Example No. | Compound No. | R³ | [α]_D | NMR |
|---|---|---|---|---|
| 40 | I-40 | H₂C—N(morpholine) | −61° (c = 0.503, H₂O, 23.5° C.) | (CD₃OD): 8.98 and 8.96 (total 1H, d, J=1.8 Hz), 7.43 and 7.36 (total 1H, d, J=1.8 Hz), 5.08 (1H, dd, J=6.0, 7.8 Hz), 4.84 (1H, m), 4.46 (1H, d, J=8.4 Hz), 4.42 (1H, dd, J=3.9, 8.4 Hz), 4.07 (1H, d, J=12.6 Hz), 3.91 (1H, m), 3.63 (5H, m), 3.56 (1H, d, J=12.6 Hz), 3.41 (1H, dd, J=6.0, 14.4 Hz), 2.47 (4H, m), 2.21 (1H, m), 2.01 (2H, m), 1.30 and 1.24 (total 3H, d, J=6.9 Hz). |
| 41 | I-41 | H₂C—N(piperidine) | −69.1° (c = 0.966, H₂O, 23.5° C.) | (CD₃OD): 8.98 and 8.96 (total 1H, d, J=2 Hz), 7.43 and 7.36 (total 1H, d, J=2 Hz), 5.07 (1H, dd, J=6.4, 8.2 Hz), 4.80 (1H, m), 4.44 (1H, d, J=8.6 Hz), 4.41 (1H, dd, J=48.2 Hz), 4.11 and 4.10 (total 1H, d, J=13 Hz), 3.90 (1H, m), 3.40 (1H, dd, J=6.4, 14.4 Hz), 2.3–2.6 (8H, m), 2.27 and 2.15 (total 3H, s), 2.20 (1H, m), 2.01 (2H, m), 1.29 and 1.24 (total 3H, d, J=6.2 Hz) |
| 42 | I-42 | H₂C—N(piperazine)N—Me | −62.3° (c = 0.514, H₂O, 23.5° C.) | (DMSO-d₆): 9.06 and 9.02 (total 1H, d, J=2 Hz), 8.81 and 8.59 (total 1H, d, J=8 Hz), 7.43 (1H, d, J=2 Hz), 7.34 (1H, br. s), 7.16 and 6.90 (1H, br.s), 4.96 (1H, m), 4.74 (1H, m), 4.50 and 4.37 (total 1H, d, J=8.2 Hz), 4.22 (1H, m), 3.95 (1H, d, J=12.8 Hz), 3.72 (1H, m), 3.60 (1H, m), 3.26 (1H, d, J=12.8 Hz), 3.20 (1H, dd, J=5.14 Hz), 3.04 (1H, dd, J=9.8, 14 Hz), 2.31 (4H, m), 1.6–2.1 (4H, m), 1.40 (6H, m), 1.16 and 1.09 (total 3H, d, J=6.4 Hz). |

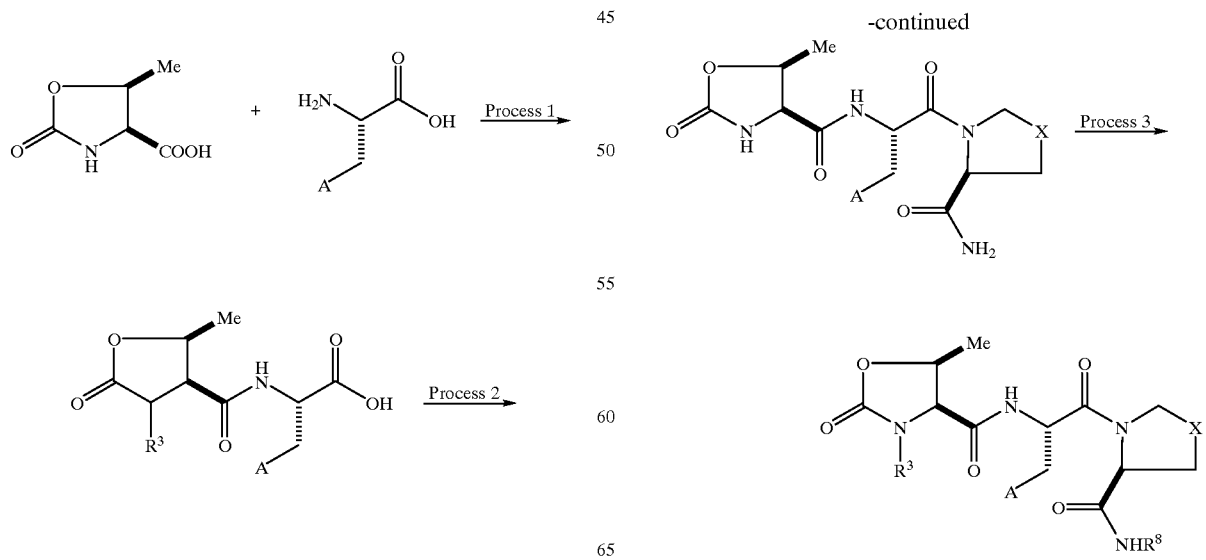

Example 44 and 45
Process 1

Preparation of cis-L-5-methyl-2-oxo-oxazolidine-4-yl-carbonyl-3-(4-thiazolyl)-L-alanine (29)

A solution of cis-L-5-methyl-2-oxo-oxazolidine-4-carboxylic acid (1.08 g, 7.5 mmol) in N,N-dimethylformamide (30 ml) was added N-hydroxysuccinimide (650 mg, 8.25 mmol) and DCC (1.70 g, 8.25 mmol) and the resulting mixture was stirred for 3 h at room temperature. After the precipitation which appeared was filtered off, to the filtrate was added 3-(4-thiazolyl)-L-alanine trifluoroacetate (4.64 g, 7.5 mmol) and triethylamine (5.23 ml, 37.5 mmol). The reaction mixture was stirred for 16 h at room temperature. The reaction mixture was concentrated in vacuo. The residue was subjected to gel filtration column chromatography (MCI GEL CHP-20P, 200 ml, aq. MeOH) and to silica gel column chromatography (chloroform:methanol=10:1) to give 890 mg (39.7%) of the compound (29).

NMR(CD$_3$OD): 9.02 (1H, J=1.8 Hz), 8.46 (1H, d, J=7.8 Hz), 7.74 (1H, s), 7.38 (1H, d, J=1.8 Hz), 4.77 (1H, dq, J=8.7, 6.6 Hz), 4.66 (1H, m), 4.21 (1H, d, J=8.7 Hz), 3.24 (1H, dd, J=5.1, 15 Hz), 3.13 (1H, dd, J=8.4, 15 Hz), 1.13 (3H, d, J=6.6 Hz).

Elemental analysis ($C_{11}H_{13}N_3O_5S$ 0.2$H_2O$) Calcd.: C,43.62; H,4.46; N,13.87; S,10.59. Found: C,43.66; H,4.45; N,13.73; S,10.39.

Example 44 and 45
Process 2

Preparation of cis-L-5-methyl-2-oxo-oxazolidine-4-yl-carbonyl-3-(4-thiazolyl)-L-alanyl-L-prolineamide (I-10)

To a solution of the compound (29) (150 mg, 0.5 mmol) and N-hydroxysuccinimide (63 mg, 0.55 mmol) in N,N-dimethylformamide (5 ml) was added DCC (114 mg, 0.55 mmol) under ice-cooling and the resulting mixture was stirred for 60 min. Subsequently, to the mixture was added L-prolineamide (63 mg, 0.55 mmol) and the resulting mixture was stirred for additional 16 h at room temperature. After the precipitation which appeared was filtered off, the filtrate was concentrated in vacuo. The residue was dissolved in water and was subjected to gel filtration column chromatography (MCL GEL CHP-20P, 200 ml, aq. MeOH) to give 164 mg (82.8%) of the same compound which are synthesized in Example 10-3.

Example 44 and 45
Process 3

Preparation of cis-L-3-acetoxymethyl-5-methyl-2-oxo-oxazolidine-4-yl-carbonyl-3-(4-thiazolyl)-L-alanyl-N-(acetoxymethyl)-L-prolineamide (I-44) and cis-L-3-acetoxymethyl-5-methyl-2-oxo-oxazolidine-4-yl-carbonyl-3-(4-thiazolyl)-L-alanyl-L-prolineamlde (I-45)

A solution of the compound (I-10) (198 mg, 0.5 mmol) in ethanol (1 ml) was added 0.1 ml of the solution of triethylamine (0.5 ml) in ethanol (10 ml) and 37% formalin (0.13 ml, 1.6 mmol) and the resulting mixture was heated at reflux on oil bath (105° C.) for 2 h. The reaction mixture was concentrated in vacuo. After the residue was dissolved in pyridine (9 ml) to the mixture was added acetic anhydride (0.9 ml) and was stood for 1 h at room temperature. After toluene was added to the reaction mixture, the resulting mixture was concentrated in vacuo. The residue was subjected to silica gel column chromatography (chloroform:methanol=19:1) to give 143 mg of the compound (I-44) and 71 mg of the compound (I-45).

Example 46

Preparation of cis-L-3-acetyl-5-methyl-2-oxo-oxazolidine-4-yl-carbonyl-3-(4-thiazolyl)L-alanyl-L-prolineamide (I-46)

After the compound (I-10) (125 mg, 0.316 mmol) was dissolved in pyridine (5 ml), to the mixture was added acetic anhydride (0.6 ml) and the resulting mixture was stood for 16 h at room temperature. Additionally, to the mixture was added acetic anhydride (0.6 ml) and the resulting mixture was stood for 2 days at room temperature. After toluene was added to the reaction mixture, the mixture was concentrated in vacuo. The residue was subjected to silica gel column chromatography (chloroform:methanol=19:1) to give 94 mg of the compound (I-46).

Example 47

Preparation of cis-L-3-acetoxy-5-methyl-2-oxo-oxazolidine-4-yl-carbonyl-3-(4-thiazolyl)-L-alanyl-L-thaiazolidine-4-carboxyamide (I-47)

In a manner similar to that described in the method of Example 44 and 45-3, after the compound (I-11) (210 mg, 0.5 mmol) was hydroxymethylated by treating with 37% formalin (0.13 ml) and triethylamine (0.05 ml), the resulting compound was acetylated by treating with acetic anhydride - pyridine to give 140 mg of the compound (I-47). The above results were shown in Table 19.

TABLE 19

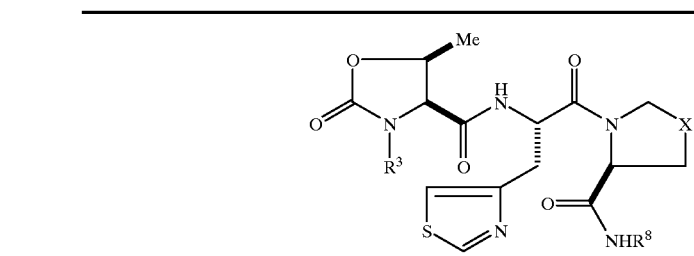

| Example No. | Compound No. | R$^3$ | R$^8$ | X | NMR |
|---|---|---|---|---|---|
| 44-3 | I-44 | CH$_2$OAc | CH$_2$OAc | CH$_2$ | (CDCl$_3$): 9.02 and 8.97 (total 1H, d, J=2.1 |

TABLE 19-continued

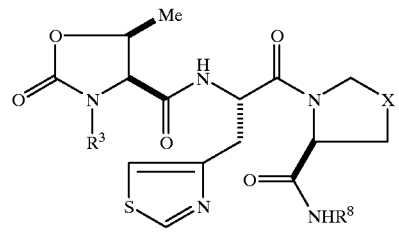

| Example No. | Compound No. | R³ | R⁸ | X | NMR |
|---|---|---|---|---|---|
| | | | | | Hz), 7.47 and 7.36 (1H, d, J=2.1 Hz), 5.31 (1H, d, J=11.4 Hz) 5.24 (1H, d, J=10.2 Hz), 5.20 (1H, d, J=10.2 Hz), 5.01 (1H, d, J=11.4 Hz), 5.00 (1H, t, J=6.9 Hz), 4.80 (1H, m), 4.57 and 4.55 (total 1H, d, J=8.4 Hz), 4.31 (1H, dd, J=4.2, 8.4 Hz), 3.86 (1H, m), 3,42 (1H, m), 3,35 (1H, m), 3,20 (1H, dd, J=6.9, 14.7 Hz), 1.8–2.3 (4H, m), 2.05 (3H, s), 2.04 (3H, s), 1.29 and 1.24 (total 3H, d, J=6.6 Hz). |
| 45-3 | I-45 | CH₂OAc | H | CH₂ | (CD₃OD): 8.97 and 8.94 (1H, d, J=1.8 Hz), 7.47 and 7.39 (total 1H, d, J=1.8 Hz), 5.31 and 5.29 (total 1H, d, J=11.2 Hz), 5.04 (1H, t, J=6.9 Hz), 5.01 and 4.98 (total 1H, d, J=11.1 Hz), 4.80 (1H, m), 4.59 and 4.56 (1H, d, J=8.7 Hz), 4.41 and 4.30 (1H, dd, J=3.9, 8.4 Hz), 3.87 (1H, m), 3.50 (1H, m), 3.40 (1H, dd, J=14.1, 6.6 Hz), 3.22 (1H, dd, J=6.9, 14.1 Hz), 1.7–2.3 (4H, m), 2.05 (3H, s), 1.30 and 1.24 (total 3H, d, J=6.6 Hz). |
| 46 | I-46 | Ac | H | CH₂ | (CD₃OD): 8.94 and 8.93 (total 1H, d, J=1.8 Hz), 7.47 and 7.38 (total 1H, d, J=1.8 Hz), 4.97 (1H, t, J6.9 Hz), 4.8–4.9 (2H, m), 4.41 and 4.25 (total 1H, dd, J=3.9, 8.7 Hz), 3.85 (1H, m), 3.44 (1H, m), 3,39 (1H, dd, J=7.2, 15 Hz), 3.23 (1H, dd, J=6.9, 15 hz), 2.46 (3H, s), 1.8–2.3 (4H, m), 1.2–1.4 (3H, m). |
| 47 | I-47 | CH₂OAc | H | S | (CD₃OD): 8.94 and 8.99 (total 1H, d, J=2.1 Hz), 7.42 and 7.48 (total 1H, d, J=2.1 Hz), 5.32 (1H, d, J=11.4 Hz), 5.13 (1H, t, J=6.9 Hz), 5.09 (1H, d, J=8.7 Hz), 5.03 (1H, d, J=11.4 Hz), 4.70–4.90 (2H, m), 4.57 (1H, d, J=8.7 Hz), 4.48 (1H, d, J=8.7 Hz), 3.43 (1H, dd, J=6.9, 14.4 Hz), 3.10–3.40 (3H, m), 2.05 (3H, s), 1.25 and 1.32 (total 3H, d, J=6.6 Hz) |

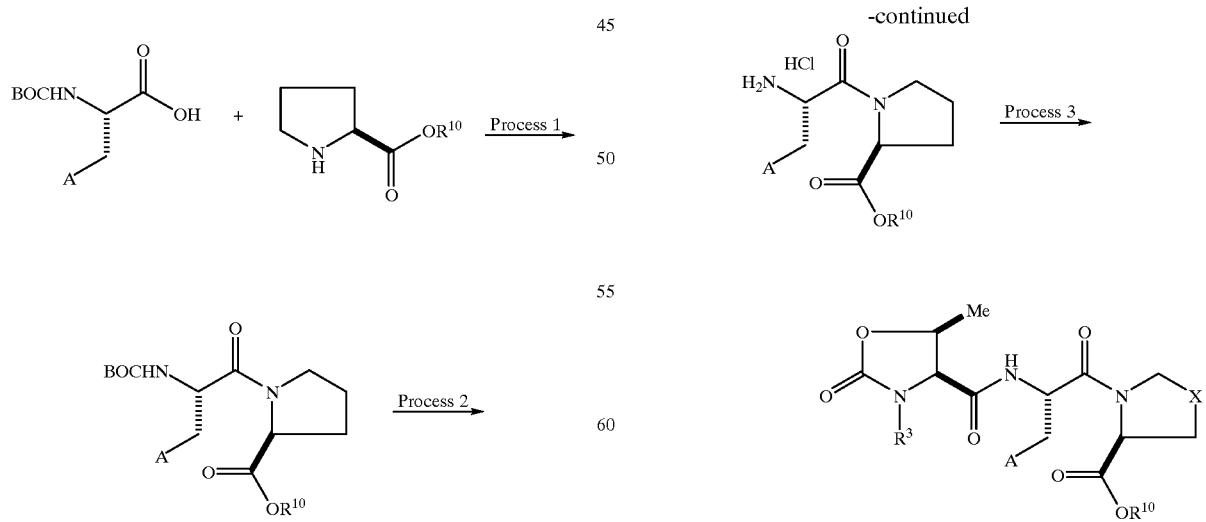

Example 48

Process 1

Preparation of N-(tert-butyloxycarbonyl)-3-(4-thiazolyl)-L-alanyl-L-proline benzyl ester (30)

A solution of N-(tert-butyloxycarbonyl)-3-(4-thiazolyl)-L-alanine (2.72 g, 10 mmol), L-proline benzyl ester hydrochloric acid (2.42 g, 10 mmol), and HOBT (135 mg, 1 mmol) in tetrahydrofuran (60 ml) was added triethylamine (1.4 ml, 10 mmol) and DCC (2.43 g, 11.8 mmol) and the resulting mixture was stirred for 18 h at room temperature. After the precipitation which appeared was filtered off, the filtrate was concentrated in vacuo. The residue (5.5 g) was subjected to silica gel column chromatography with Lobar® column C (Merck inc.) (toluene:acetone=9:1) to give 4.16 g of the compound (30).

Example 48

Process 2

Preparation of 3-(4-thiazolyl)-L-alanyl-L-proline benzyl ester hydrochloride (32)

To a solution of the compound (30) (3 g, 6.528 mmol) in ethyl acetate (10 ml) was added a solution of 4N hydrogen chloride in ethyl acetate (33 ml) under ice-cooling and the resulting mixture was stirred for 3 h. To the reaction mixture was added diethyl ether and the precipitation which apl) eare(d was filtered off to give 2.77 g of compound (32). This compound was used in the next reaction without purification.

The compounds (31) and (33) are synthesized in a manner similar to that described in the above method. The results were shown in Table 20.

TABLE 20

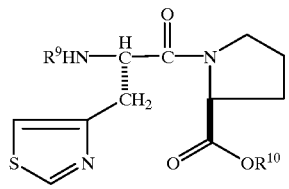

| Example No. | Compound No. | $R^9$ | $R^{10}$ | salt | $[\alpha]_D$ | NMR |
|---|---|---|---|---|---|---|
| 48-1 | 30 | BOC | Bzl | — | −55.6° (c = 1.03, MeOH, 23° C.) | (CDCl$_3$): 8.75 and 8.72 (total 1H, d, J=1.8 Hz), 7.35 (5H, m, Ph), 7.10 and 7.08 (total 1H, d, J=1.8 Hz), 5.39 (1H, d, J=9 Hz), 5.19 (1H, d, J=12.4 Hz), 5.27 (1H, d, J=12.3 Hz), 4.81 (1H, m), 4.58 (1H, dd, J=3.9, 8.4 Hz), 3.73 and 3.51 (total 2H, m), 3.26 (1H, dd, J=5.7 Hz, 14.1 Hz), 3.02 (1H, dd, J=7.5, 14.1 Hz), 2.19 (1H, m), 1.97 (3H, m), 1.37 (9H, s). |
| 48-2 | 32 | H | Bzl | HCl |  | (CD$_3$OD): 9.41 (1H, d, J=1.8 Hz), 7.68 (1H, d, J=1.8 Hz), 5.17 (1H, s), 4.60 (2H, m), 3.75 (1H, m), 3.45 (3H, m), 2.30 (1H, m), 2.00 (3H, m). |
| 49-1 | 31 | BOC | iso-Pr | — | −40.8° (c = 1.015, CHCl$_3$, 26° C.) | (CDCl$_3$): 8.77 (1H, d, J=2 Hz), 7.19 (1H, s), 5.40 (1H, d, J=8.6 Hz), 5.03 (1H, q, J=6.2 Hz), 4.83 (1H, m), 4.48 (1H, m), 3.73 (1H, m), 3.59 (1H, m), 3.32 (1H, dd, J=5.2 Hz, 14.4 Hz), 3.04 (1H, dd, J=7.8, 14.4 Hz), 2.20 (1H, m), 1.97 (3H, m), 1.36 (9H, s), 1.26 (3H, d, J=6.4 Hz), 1.22 (3H, d, J=6.4 Hz). |
| 49-2 | 33 | H | iso-Pr | HCl |  |  |

Example 48

Process 3

Preparation of cis-L-5-metyhyl-2-oxo-oxazolidine-4-yl-carbonyl-3-(4-thiazolyl)-L-alanyl-L-proline benzyl ester (I-48)

A solution of cis-L-5-methyl-2-oxo-oxazoline-4-carboxylic acid (316 mg, 2.17 mmol) and N-hydroxysuccinimide (249 mg, 2.17 mmol) in N, N-dimethylformamide (5 ml) was added DCC (448 mg, 2.17 mmol) and the resulting mixture was stirred for 4 h at room temperature. After the precipitation which appeared was filtered off, to the filtrate was added 865 mg (2.17 mmol) of the compound (32) and triethylamine (1.21 ml, 8.7 mmol). The reaction mixture was stirred for 16 h at room temperature. After the precipitation which appeared was filtered off, the filtrate was concentrated in vacuo. The residue was subjected to gel filtration column chromatography (MCL GEL CHP-20P, 200 ml, aq. MeOH) and to silica gel column chromatography to give 496 mg of the compound (I-48).

The compound (I-49) was synthesized in a manner similar to that described in the above method. The results were shown in Table 21.

Example 50

Preparation of cis-L-5-methyl-2-oxo-oxazolidine-4-yl-carbonyl-3-(4-thiazolyl)-L-alanyl-L-proline (I-50)

A solution of the compound (I-48) (1.99 g, 4.09 mmol) in 50% aqueous methanol was added lithium hydroxide (858 mg, 20.45 mmol) and the resulting mixture was stirred for 35 min. at room temperature. After the reaction mixture was neutralized by adding 1N hydrochloric acid (20.4 ml), the resulting mixture was concentrated in vacuo to about half volume. The aqueous solution was washed with ethyl acetate twice. The aqueous layer was subjected to gel filtration column chromatography (MCI GEL CHP-20P, 200 ml, aq. MeOH) to give 1.29 g of the compound (I-50). The result was shown in Table 21.

TABLE 21

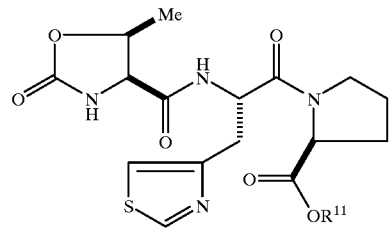

| Example No. | Compound No. | $R^{11}$ | $[\alpha]_D$ | IR (cm$^{-1}$) | NMR |
|---|---|---|---|---|---|
| 48-3 | I-48 | Bzl | −55.9° (c = 0.508, MeOH, 26° C.) | | (CD$_3$OD): 8.93 (1H, d, J=2 Hz), 7.35 (5H, m, Ph), 7.30 (1H, d, J=2 Hz), 5.15 (12H, s), 5.11 (1H, m), 4.90 (1H, m), 4.49 (1H, m), 4.31 (1H, d, J=8.6 Hz), 3.90 (1H, m), 3.60 (1H, m), 3.17 (2H, m), 2.25 (1H, m), 1.97 (3H, m), 1.17 (3H, d, J=6.6 Hz). |
| 49-3 | I-49 | iso-Pr | −53.7° (c = 0.501, MeOH, 25° C.) | | (CD$_3$OD): 8.99 (1H, d, J=2 Hz), 7.44 (1H, d, J=2 Hz), 5.00 (3H, m), 4.40 (1H, m), 4.34 (1H, d, J=8.6 Hz), 3.93 (1H, m), 3.66 (1H, m), 2.30 (1H, m), 2.00 (3H, m), 1.28 (6H, t, J=6.2 Hz), 1.20 (3H, d, J=6.6 Hz). |
| 50 | I-50 | H | −52.0° (c = 1.01, H$_2$O 23° C.) | (KBr) 3398, 3299, 1749, 1636, 1523, 1450, 1230. | (CD$_3$OD): 8.95 (1H, d, J=2.1 Hz), 7.40 and 7.33 (total 1H, d, J=2.1 Hz), 5.09 (1H, dd, J=5.4, 8.4 Hz), 4.90 (1H, m), 4.42 (1H, dd, J=3.6, 8.1 Hz), 4.37 and 4.32 (total 1H, d, J=8.7 Hz), 3.91 (1H, m), 3.61 (1H, m), 3.30 (1H, m), 3.17 (1H, dd, J=8.4, 14.7 Hz), 2.25 (1H, m), 2.01 and 1.83 (total 3H, m), 1.25 and 1.18 (total 3H, d, J=6.9 Hz). |

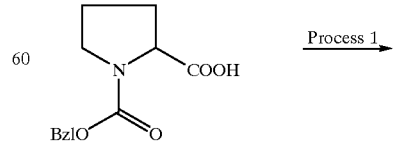

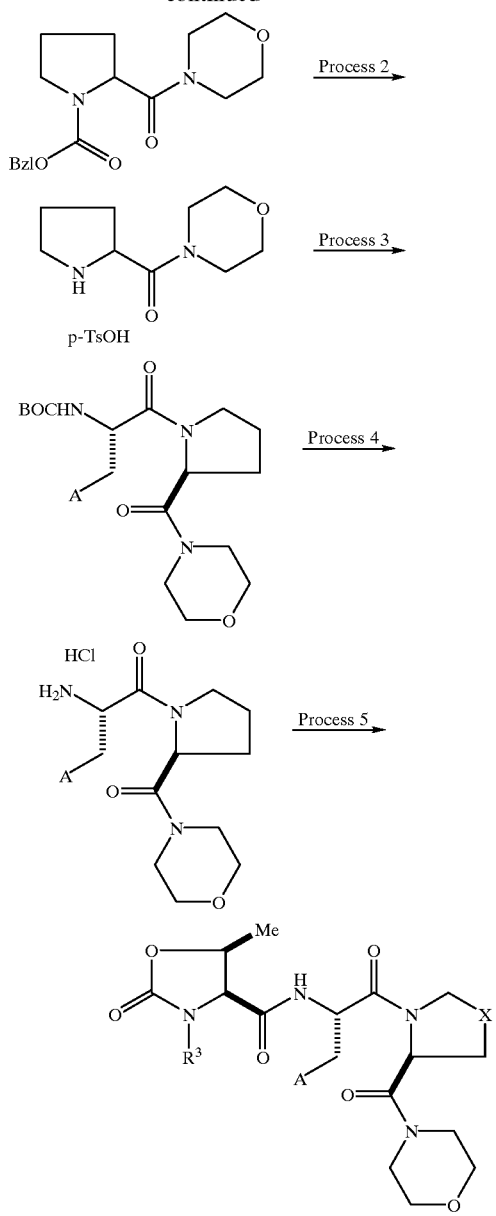

Example 51

Process 1

Preparation of 4-(N-benzyloxycarbonyl-L-prolyl) morpholine (34)

A solution of N-benzyloxycarbonyl-L-proline (5 g, 20.06 mmol), morpholine (1.92 ml, 20.06 mmol), and N-hydroxysuccinimide (2.31 g, 20.06 mmol) in N,N-dimethylformamide (100 ml) was added DCC (4.14 g, 20.06 mmol) and the resulting mixture was stirred for 4 h at room temperature. After the precipitation was filtered off, the filtrate was concentrated in vacuo. The residue was dissolved in ethyl acetate and the resulting precipitation was filtered off. After the filtrate was washed with dilute hydrochloric acid, saturated sodium hydrogencarbonate aq., and water, the organic layer was dried over magnesium sulfate and concentrated in vacuo. The residue was crystallized from the mixed solvents of ethyl acetate-hexane to give the compound (34) (4.44 g, 69.5%).

mp: 142–143° C.

$[\alpha]_D$=−18.0° (c=1, CHCl$_3$, 23° C.)

IR(CHCl$_3$)cm−1: 1700, 1660, 1420.

NMR(CDCl$_3$): 7.35 (5H, m), 5.12 (2H, m), 4.59 and 4.70 (total 1H, dd, J=3.6, 8.4 Hz), 3.20–3.90 (10H, m), 1.80–2.30 (4H, m).

Elemental analysis (C$_{17}$H$_{22}$N$_2$O$_4$) Calcd.: C,64.13; H,6.96; N,8.80. Found: C,53.99; H,6.94; N,8.81.

Example 51

Process 2

Preparation of 4-L-prolyl-morpholine p-toluenesulfonate (35)

A solution of the compound (35) (3.6 g, 11.31 mmol) in methanol (50 ml)-water (10 ml) was hydrogenated using 5% Pd/C (1.6 g) and p-toluenesulfonic acid (2.15 g, 11.31 mmol) for 3 h at room temperature. The catalyst was filtered off and the filtrate was concentrated in vacuo to obtain the compound (35) (4.31 g, 100%).

mp: 130–131° C.

NMR(CD$_3$OD): 7.70 (2H, m), 7.24 (2H, m), 4.65 (1H, dd, J=6.2, 8.4 Hz), 3.20–3.80 (10H, m), 1.80–2.60 (4H, m), 2.37 (3H, s).

Elemental analysis (C$_{16}$H$_{24}$N$_2$O$_5$S) Calcd.: C,53.92; H,6.79: N,7.86: S,9.00. Found: C,53.91; H,6.73; N,7.97; S,8.99.

Example 51

Process 3

Preparation of 4-[N-{N-(tert-butoxycarbonyl)-3-(4-theiazolyl)-L-alanyl}-L- prolyl]morpholine (36)

In a manner similar to that described in the method of synthesis of the compound (34), the compound (35) (2.7 g, 7.57 mmol) was condensed with N-(tert-butoxycarbonyl)-3-(4-thiazolyl)-L-alanine (2.03 g, 7.57 mmol) in the presence of HOBT (200 mg, 1.498 mmol), triethylamine (2.1 ml, 14.98 mmol), and DCC (1.55 g, 7.49 mmol) in N,N-dimethylformamide. The product was subjected to silica gel column chromatography (chloroform:methanol=50:1) to give the compound (36) (2.23 g, 67.1%).

$[\alpha]_D$=−23.1° (c=0.91, CHCl$_3$, 25° C.)

IR(CHCl$_3$)cm$^{-1}$: 3433, 1707, 1644, 1501, 1441, 1232, 1167, 1115.

NMR(CDCl$_3$): 8.76 (1H, d, J=2 Hz), 7.21 (1H, d, J=2 Hz), 5.46 (1H, d, J=9 Hz), 4.83 (2H, m), 3.40–4.00 (10H, m), 3.35 (1H, dd, J=5, 14.6 Hz), 3.08 (1H, dd, J=7.8, 14.6 Hz), 1.70–2.30 (4H, m), 1.37 (9H, s).

Elemental analysis (C$_{20}$H$_{30}$N$_4$O$_5$S 0.5H$_2$O) Calcd.: C,53.67; H,6.98; N,12.52; S,7.16. Found: C,53.71; H,7.07; N,12.34; S,7.17.

Example 51

Process 4

Preparation of 4-[N-{3-(4-thiazolyl-L-alanyl}-L-prolyl]morpholine hydrochloride (37)

To a solution of the compound (36) (1.5 g, 3.42 mmol) in ethyl acetate (17 ml) was added a solution of 4N hydrochloric acid in ethyl acetate (17 ml) under ice-cooling and the resulting mixture was stirred for 3 h at the same temperature with stirring. The precipitation which appeared was filtered off and washed with ethyl acetate to give the compound (37) (1.33 g, 94.4%).

$[\alpha]_D$=−39.1° (c=1, MeOH, 25° C.)

IR(CHCl$_3$)cm$^{-1}$: 3429, 1741, 1654, 1610, 1465, 1370, 1238, 1111.

NMR(CD$_3$OD): 9.86 (1H, d, J=2 Hz), 8.06 (1H, d, J=2 Hz), 4.98 (1H, dd, J=6.0, 8.4 Hz), 4.76 (1H, t, J=5.4 Hz), 3.40–4.00 (12H, m), 1.80–2.40 (4H, m).

Example 51

Process 5

Preparation of 4-[N-{N-(cis-L-5-methyl-2-oxo-oaxzolidine-4-yl-carbonyl)-3-(4-thiazolyl)-L-alanyl}-L-prolyl]morpholine (I-51)

In a manner similar to that described in the method of synthesis of the compound (34), cis-L-5-methyl-2-oxo-oxazolidine-4-carboxylic acid (300 mg, 2.07 mmol) was condensed with the compound (37) (850 mg, 2.07 mmol) in the presence of N-hydroxysuccinimide (240 mg, 2.07 mmol), DCC (470 mg, 2.28 mmol), and triethylamine (1.16 ml, 8.28 mmol) in N,N-dimethylformamide to give 560 mg of the compound (I-51).
The result was shown in Table 22.

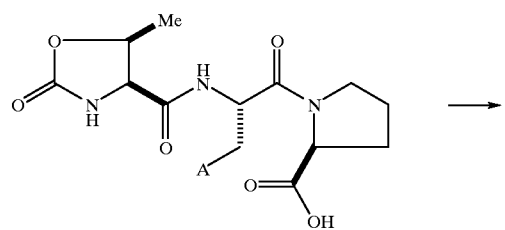

→

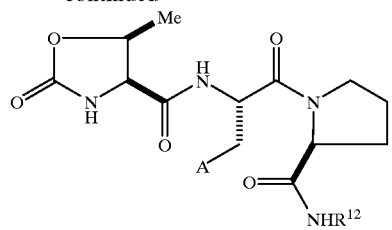

Example 52

Preparation of cis-L-5-methyl-2-oxo-oxazolidine-4-yl-carbonyl-3-(4-thiazolyl)-L-alanyl-N-(tert-butyl)-L-prolineamide (I-52)

In a manner similar to that described in the method of synthesis of the compound (34), the compound (I-50) (300 mg, 0.76 mmol) was condensed with tert-butylamine (110 mg, 1.52 mmol) in the presence of N-hydroxysuccinimide (87 mg, 0.76 mmol) and DCC (170 mg, 0.84 mmol) in N,N-dimethylformamide to give 210 mg of the compound (I-52).

In the manner to that described in the above method, the compound (I-53) was synthesized.
The above results were shown in Table 22.

TABLE 22

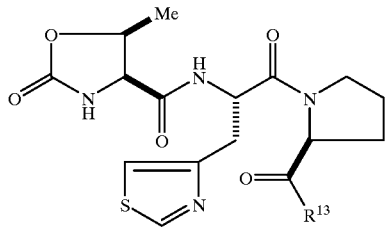

| Example No. | Compound No. | $R^{13}$ | $[\alpha]_D$ | NMR |
|---|---|---|---|---|
| 51-5 | I-51 | -N(morpholine) | -55.9° (c = 0.508, MeOH, 26° C.) | (CD$_3$OD): 8.94 and 8.98 (total 1H, d, J2 Hz), 7.32 and 7.42 (total 1H, d, J=2 Hz), 5.09 (1H, dd, J=4.6, 9.4 Hz), 4.70–5.00 (2H, m), 4.30 and 4.33 (total 1H, d, J=8.6 Hz), 3.50–4.10 (10H, m), 3.38 (1H, dd, J=4.6, 15 Hz), 3.15 (1H, dd, J=9.4, 15 Hz), 1.60–2.40 (4H, m), 1.17 and 1.21 (total 3H, d, J=6.6 Hz). |
| 52 | I-52 | t-BuNH | -53.7° (c = 0.501, MeOH, 25° C.) | (CD$_3$OD): 8.95 and 8.97 (total 1H, d, J=1.8 Hz), 7.57 and 7.71 (total 1H, s), 7.34 and 7.42 (total 1H, d, J=1.8 Hz), 5.06 (1H, dd, J=5.4, 8.1 Hz), 4.90 (1H, m), 4.34 (1H, t, J=8.7 Hz), 4.31 (1H, d, J=8.7 Hz), 3.60–3.91 (2H, m), 3.37 (1H dd, J=5.4, 15.3 Hz), 3.19 (1H, dd, J=8.1, 15.3 Hz), 1.70–2.30 (4H, m), 1.33 (9H, s), 1.18 and 1.25 (total 3H, d, J6.3 Hz) |
| 53 | I-53 | n-PenNH | -52.0° (c = 1.01, H$_2$O, 23° C.) | (CD$_3$OD): 8.97 (1H, d, J=2.1 Hz), 7.35 and 7.44 (total 1H, d, J=2.1 Hz), 5.00 (1H, t, J=6.9 Hz), 4.91 (1H, m), 4.37 (1H, dd, J=4.2, 10.5 Hz), 4.33 and 4.35 (total 1H, d, J=9 Hz), 3.87 (1H, m), 3.30–3.60 (5H, m), 1.70–2.30 (4H, m), 1.51 (2H, m), 1.31 (4H, m), 1.20 and 1.25 (total 3H, d, J=6.6 Hz), 0.90 (3H, t, J=6.9 Hz). |

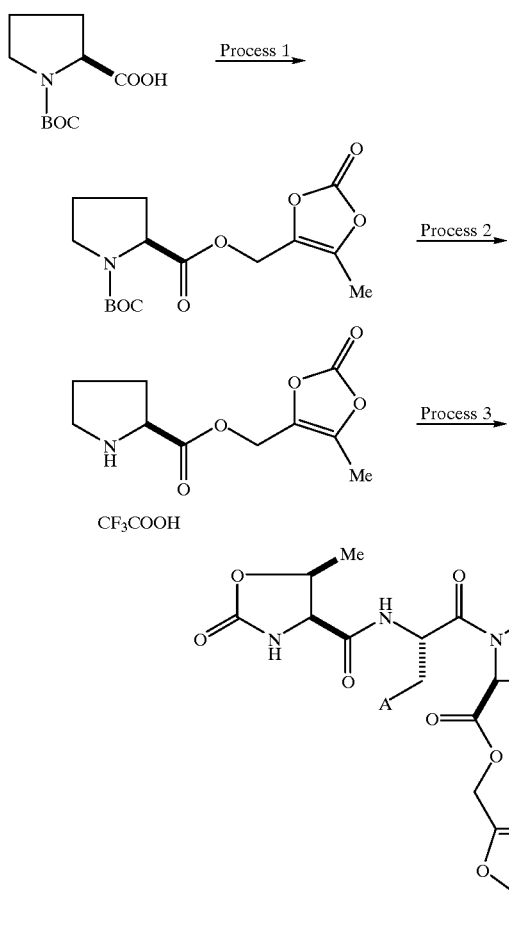

Example 54
Process 1

Preparation of N-(tert-butoxycarbonyl)-L-proline 5-methyl-2-oxo-1,3-dioxolene-4-ylmethyl ester (38)

A solution of 4-hydroxymethyl-5-methyl-2-oxo-1,3-dioxolene (651 mg, 5 mmol) which was synthesized in accordance with the method described in Synthetic Commun., 22, 1277 (1992), tert-butyloxycarbonyl-L-proline (1.07 g, 5 mmol), and 4-dimethylaminopyridine (61 mg, 0.5 mmol) in THF (20 ml) was added DCC (1.14 g, 5.5 mmol) and the resulting mixture was stirred for 16 h at room temperature. After the precipitation which appeared was filtered off, the filtrate was concentrated in vacuo. The residue was subjected to silica gel column chromatography (hexane:acetone=4:1) to give the compound (38) (1.33 g, 81.2%).

NMR(CDCl$_3$): 4.8–5.0 (2H, m), 4.2–4.4 (1H, m), 3.3–3.6 (2H, m), 2.19 and 2.17 (total 3H, s), 1.93 (2H, m), 1.66 (2H, m), 1.45–1.39 (9H, s).

Example 54
Process 2

Preparation of L-proline 5-methyl-2-oxo-1,3-dioxolene-4-ylmethyl ester trifuluoroacetate (39)

Trifluoroacetic acid (2.5 ml) was added to the compound (38) (360 mg, 1.1 mmol) under ice-cooling and the resulting mixture was stood for 45 min. To the reaction mixture was added toluene and the mixture was concentrated in vacuo to give 490 mg of the compound (39). This compound was used in the next reaction without purification.

NMR(CDCl$_3$): 5.03 (1H, d, J=14.1 Hz), 4.97 (1H, d, J=14.1 Hz), 4.53 (1H, m), 3.52 (2H, m), 2.51 (1H, m), 2.18 (3H, s), 2.18 (3H, s).

Example 54
Process 3

Preparation of cis-L-5-methyl-2-oxo-oxazolidine-4-yl-carbonyl-3-(4-thiazolyl)-L-alanyl-L-proline 5-methyl-L-proline 5-methyl-2-oxo-1,3-dioxolene-4-ylmethyl ester (I-54)

In a manner similar to that described in the synthetic method of the compound (34), the compound (29) (299 mg, 1 mmol) was condensed with the compound (39) (130 mg, 0.76 mmol) in the presence of N-hydroxysuccinimide (127 mg, 1.1 mmol), DCC (227 mg, 1.1 mmol), and triethylamine (0.56 ml, 4 mmol) in N,N-dimethylformamide to give 162 mg (30%) of the compound (I-54). The chemical formula was shown below.

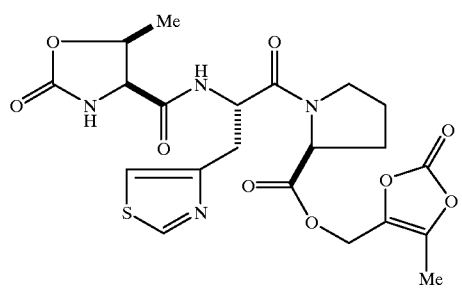

$[\alpha]_D = -56.2°$ (c=0.502, H$_2$O, 26° C.).

NMR(CD$_3$OD): 8.97 and 8.96 (total 1H, d, J=2.1 Hz), 7.39 and 7.32 (total 1H, d, J=2.1 Hz), 5.09 (1H, m), 4.96 (2H, s), 4.90 (1H, m), 4.46 (t 1H, m), 4.31(1H, t, J=8.7 Hz), 3.92 (1H, m), 3.61 (1H, m), 3.29 (1H, dd, J=5.4, 14.7 Hz), 3.16 (1H, dd, J=8.4, 14.7 Hz), 2.27 (1H, m), 2.17 (3H, s), 2.00 (3H, m), 1.23 and 1.18 (total 3H, d, J=6.6 Hz).

Elemental analysis (C$_{21}$H$_{24}$N$_4$O$_9$S 1.1H$_2$O) Calcd.: C,47.74; H,5.00; N,10.60; S,6.07. Found: C,47.78; H,5.04; N,10.67; S,5.97.

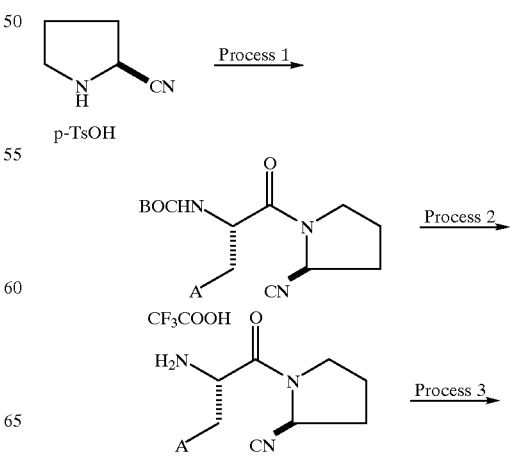

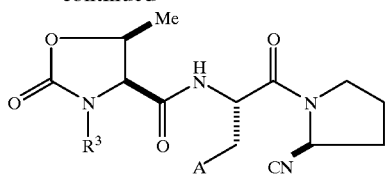

Example 55
Process 1

Preparation of N-(tert-butoxycarbonyl)-3-(4-thiazolyl)-L-alanyl-2S-cyanopyrrolidine (40)

2S-Cyanopyrrolidine p-toluenesulfonate (440 mg, 1.62 mmol) which was synthesized in accordance with Bioorg, Med. Chem. Lett., 6, 1163 (1996) was condensed with N-(tert-butoxycarbonyl)-3-(4-thiazolyl)-L-alanine (440 mg, 1.62 mmol) in the presence of N-hydroxysuccinimide (190 mg, 1.62 mmol), DCC (370 mg, 1.78 mmol), and triethylamine (0.46 ml, 3.24 mmol) to give 180 mg (31.5%) of the compound (40).

$[\alpha]_D = -37.2°$ (c=0.503, CHCl$_3$, 26° C.)

IR(Nujol)cm$^{-1}$: 2246, 1697, 1645, 1162.

NMR(CDCl$_3$): 8.79 (1H, d, J=2 Hz), 7.15 (1H, d, J=2 Hz), 5.41 (1H, d, J=8.2 Hz), 4.79 (1H, dd, J=7, 8.2 Hz), 4.72 (1H, dd, J=3.6, 6.9 Hz), 3.62 (1H, m), 3.35 (1H, m), 3.22 (2H, d, J=7 Hz), 1.90–2.3 (4H, m), 1.40(9H, s).

Elemental analysis (C$_{16}$H$_{22}$N$_4$O$_3$S) Calcd.: C,54.84; H,6.33; N,15.99: S,9.15. Found: C,54.64; H,6.30; N,15.80; S,8.95.

Example 55
Process 2

Preparation of 3-(4-thiazolyl)-L-alanyl-2(S)-cyanopyrrolidine trifluoroacetate (41)

Trifluoroacetic acid (5 ml) was added to the compound (40) (500 mg, 1.43 mmol) under ice-cooling and the resulting mixture was stirred for 90 min. Toluene was added to the reaction mixture and the mixture was concentrated in vacuo to give 970 mg of the compound (41). This compound was used in the next reaction without purification.

NMR(CDCl$_3$): 8.85 (1H, d, J=2 Hz), 7.31 (1H, d, J=2 Hz), 4.78 (1H, dd, J=4.8, 6.6 Hz), 4.62 (1H, t, J=6.6 Hz), 3.10–3.70 (4H, m), 1.80–2.3 (4H, m).

Example 55
Process 3

Preparation of Cis-L-5-methyl-2-oxo-oxazolidine-4-yl-carbonyl-3-(4-thiazolyl)-L-alanyl-2(S)-cyanopyrrolidine (I-55)

In a manner similar to that described in the synthetic method of the compound (34), cis-L-5-methyl-2-oxo-oxazolidine-4-carboxylic acid (210 mg, 1.43 mmol) was condensed with the compound (41) (970 mg, 1.43 mmol) in the presence of N-hydroxysuccinimide (160 mg, 1.43 mmol), DCC (320 mg, 1.57 mmol), and triethylamine (0.6 ml, 4.29 mmol) in N,N-dimethylformamide to 330 mg of compound (I-55). The result was shown in Table 23.

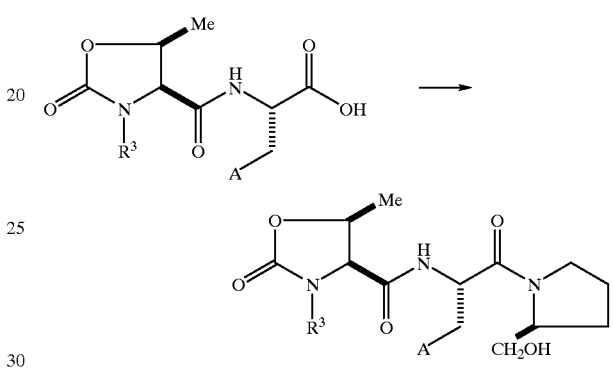

Example 56

Preparation of cis-L-5-methyl-2-oxo-oxazolidine-4-yl-carbonyl-3-(4-thiazolyl)-L-alanyl-L-prolinol (I-56)

In a manner similar to that described in the synthetic method of the compound of (34), the compound of (29) (299 mg, 1 mmol) was condensed with L-prolinol (101 mg, 1 mmol) in the presence of N-hydroxysuccinimide (127 mg, 1.1 mmol), DCC (227 mg, 1.1 mmol), and triethylamine (0.15 ml, 1.1 mmol) in N, N-dimethylformamide to give 162 mg of the compound (I-56). The result was shown in Table 23.

TABLE 23

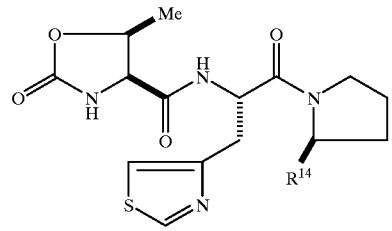

| Example No. | Compound No. | R$^{14}$ | $[\alpha]_D$ | NMR |
|---|---|---|---|---|
| 55-3 | I-55 | —CN | −35.0° (c = 1.007, MeOH, 25° C.) | (CD$_3$OD): 8.98 (1H, d, J=2 Hz), 7.35 (1H, d, J=2.1 Hz), 4.90–5.00 (2H, m), 4.70 (1H, dd, J=8, 3.6 Hz), 4.34 (1H, d, J=8.4 Hz), 3.77 (1H, m), 3.43 (1H, m), 3.30 (1H, m), |

TABLE 23-continued

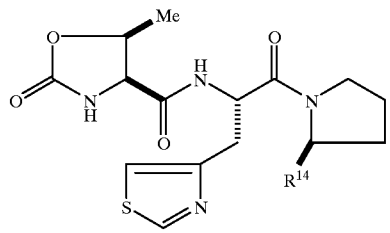

| Example No. | Compound No. | R[14] | [α]$_D$ | NMR |
|---|---|---|---|---|
| 56 | I-56 | —CH$_2$OH | −10.7° (c = 0.506, H$_2$O, 26° C.) | 3.24 (1H, dd, J=7.2, 14.1 Hz), 2.10 (4H, m), 1.23 (3H, d, J=6.3 Hz). (CD$_3$OD): 8.98 and 8.95 (total 1H, d, J=2.1 Hz), 7.36 and 7.35 (1H, d, J=2.1 Hz), 5.21 and 5.06 (1H, t, J=7.5 Hz), 4.91 (1H, m), 4.37 and 4.35 (total 1H, d, J=8.7 Hz), 4.06 (1H, m), 3.7–3.9 (1H, m), 3.51 (1H, dd, J=3.9, 10.8 Hz), 3.43 (1H, dd, J=6.3, 10.8 Hz), 3.40 (1H, m), 3.25 (2H, m), 1.6–2.0 (4H, m), 1.25 and 1.22 (total 3H, d, J=6.3 Hz). |

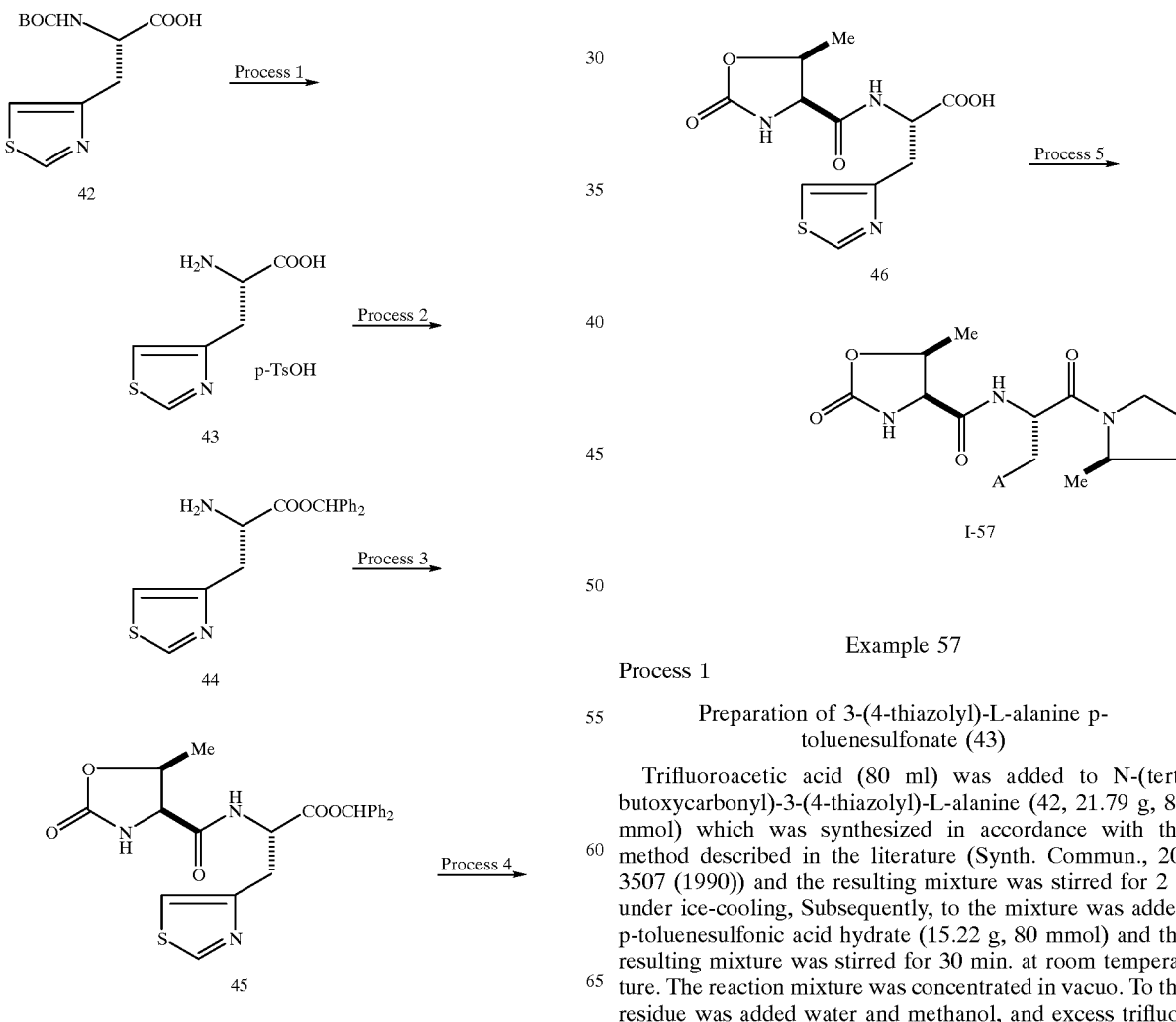

Example 57

Process 1

Preparation of 3-(4-thiazolyl)-L-alanine p-toluenesulfonate (43)

Trifluoroacetic acid (80 ml) was added to N-(tert-butoxycarbonyl)-3-(4-thiazolyl)-L-alanine (42, 21.79 g, 80 mmol) which was synthesized in accordance with the method described in the literature (Synth. Commun., 20, 3507 (1990)) and the resulting mixture was stirred for 2 h under ice-cooling, Subsequently, to the mixture was added p-toluenesulfonic acid hydrate (15.22 g, 80 mmol) and the resulting mixture was stirred for 30 min. at room temperature. The reaction mixture was concentrated in vacuo. To the residue was added water and methanol, and excess trifluoroacetic acid was removed by concentrating in vacuo. To the residue was added diethyl ether and the precipitation which appeared was filtered off to give 29.8 g (quantitative) of the compound (43).

NMR(CD$_3$OD): 9.01 (1H, d, J=1.8 Hz), 7.70 (2H, m), 7.46 (1H, d, J=1.8 Hz), 7.23 (2H, m), 4.38 (1H, dd, J=4.8 and 7.6 Hz), 3.45 (2H, m), 2.37 (3H, s).

Example 57
Process 2

Preparation of 3-(4-thiazolyl)-L-alanine diphenylmethylester p-toluenesulfonate (44)

To a solution of 38.85 g of the compound (43) (112.8 mmol) in ethanol (200 ml)-THF (600 ml) was added diphenyldiazomethane (39 g, 201 mmol) little, by little over 30 min. at room temperature with stirring. After the reaction mixture was stirred for 1 h at room temperature, to the mixture was added diphenyldiazomethane (10 g, 51.5 mmol) and the resulting mixture was stirred for 1 h. To the reaction mixture was added acetic acid (0.1 ml) for quenching the excess reagent and the mixture was concentrated in vacuo. The residue (92 g) was crystallized by adding ether (1 L) to give 49.05 g (96.1%) of the compound (44).

mp: 139–140° C.

$[\alpha]_D$=−34.7° (c=1.006, CHCl$_3$, 23° C.)

IR(KBr)cm$^{-1}$: 1753, 1602, 1512, 1496, 1260, 1224, 1171, 1124, 1036, 1012.

NMR(CD$_3$OD): 8.92 (1H, d, J=2 Hz), 7.70 (2H, m), 7.2–7.4 (13H, m), 6.91 (1H, s), 4.62 (1H, t, J=5.8 Hz), 3.47 (2H, d, J=5.8 Hz), 2.36 (3H, s).

Elemental analysis (C$_{26}$H$_{26}$N$_2$O$_5$S$_2$) Calcd.: C,61.16; H,5.13; N,5.49; S,12.56. Found: C,61.14; H,5.32; N,5.41; S,12.46.

Example 57
Process 3

Preparation of cis-L-5-methyl-2-oxo-oxazolidine-4-yl-carbonyl-3-(4-thiazolyl)-L-alanine diphenylmethyl ester (45)

A solution of 13.95 g (96.14 mmol) of cis-L-5-methyl-2-oxo-oxazolidine-4-carboxylic acid, 49.09 g (96.14 mmol) of the compound (44), 2.6 g (19.23 mmol) of N-hydroxybenzotriazole, and 14.1 ml (101 mmol) of triethylamine in THF (1 L) was added DCC (20.83 g, 101 mmol) under ice-cooling. After the mixture was stirred for 10 min. at the same temperature, the ice-cooling bath was removed and the reaction mixture was stirred for 20 h at room temperature. After the precipitation which appeared was filtered off, the filtrate was concentrated in vacuo to give oily residue (82.7 g). The reside was dissolved in ethyl acetate (700 ml) with heating and the precipitation which appeared was filtered off. The filtrate was washed with sodium carbonate aq. and water. After methanol (20 ml) was added to the organic layer, the organic layer was dried over magnesium sulfate and concentrated in vacuo. The precipitated crystal was filtered off and washed with ethyl acetate-ether (2:3) to give 35.69 g (79.8%) of the compound (45). After the mother liquor was concentrated in vacuo, the residue was crystallized from ethyl acetate-ether to give 2.62 g (5.9%) of the compound (45).

mp: 176–177° C.

$[\alpha]_D$=−39.2° (c=1.007, CHCl$_3$, 24° C.)

IR(KBr)cm$^{-1}$: 1739, 1681, 1508, 1453, 1386, 1237, 1193, 1089.

NMR(CDCl$_3$): 8.71(1H, d, J=1.8 Hz), 8.18 (1H, d, J=7.8 Hz), 7.2–7.4 (10H, m), 6.82 (1H, s), 6.66 (1H, d, J=1.8 Hz), 5.79 (1H, s), 5.12 (1H, m), 4.94 (1H, m), 4.35 (1H, dd, J=1.8 and 9.0 Hz), 3.40 (1H, dd, J=5.7 and 15 Hz), 3.29 (1H, dd, J=4.5 and 15 Hz), 1.27 (3H, d, J=6.3 Hz).

Elemental analysis (C$_{24}$H$_{23}$N$_3$O$_5$S) Calcd.: C,61.92; H,4.98; N,9.03; S,6.89. Found: C,61.95; H,5.01; N,8.94; S,6.62.

Example 57
Process 4

Preparation of cis-L-5-methyl-2-oxo-oxazolidine-4-yl-carbonyl-3-(4-thiazolyl)-L-alanine(46)

Anisole (240 ml) and trifluoroacetic acid (120 ml) was added to 41.24 g (88.59 mmol) of the compound (45) under ice-cooling and the resulting mixture was stirred for 15 min. After the cooling bath was removed, the mixture was stirred for 2.5 h at room temperature. The reaction mixture was concentrated in vacuo to give oily residue. To the residue was added ether (500 ml) and the precipitation which appeared was filtered off as powder. The powder was dissolved in water (50 ml)—methanol (300 ml) with heating and the precipitation which appeared was filtered off. The filtrate was concentrated in vacuo. To the residue was added the seed crystal and methanol and the resulting mixture was stood for 3 days at room temperature. The precipitated crystal was filtered off to give 14.89 g (56.1%) of the compound (46). The mother liquor was concentrated in vacuo and the residue was crystallized from methanol-ether to give 10.3 g (38%) of the compound (46).

mp: 214–215° C.

IR(KBr)cm$^{-1}$: 1753, 1707, 1655, 1548, 1529, 1409, 1343, 1264, 1236, 1102, 1092.

NMR(DMSO-d6): 9.02 (1H, d, J=1.8 Hz), 8.46 (1H, d, J=7.8 Hz), 7.74 (1H, s), 7.38 (1H, d, J=1.8 Hz), 4.77 (1H, dq, J=6.6 and 8.7 Hz), 4.66 (1H, m), 4.21 (1H, d, J=8.7 Hz), 3.24 (1H, dd, J=5.1 and 15 Hz), 3.13 (1H, dd, J=8.4 and 15 Hz), 1.13 (3H, d, J=6.6 Hz).

Elemental analysis (C$_{11}$H$_{13}$N$_3$O$_5$S) Calcd.: C,44.14; H,4.38; N,14.04; S,10.71. Found: C,43.94; H,4.478; N,14.09; S,110.58.

Example 57
Process 5

Preparation of cis-L-5-methyl-2-oxo-oxazolidine-4-yl-carbonyl-3-(4-thiazolyl)-L-alanyl-2(R)-methylpyrrolidine (I-57)

(Method A) To a suspension of 12.1 (40.48 mM) of the compound (46) and N-hydroxysuccinimide (4.66 g, 40.48 mM) in THF (242 ml) was added DCC (8.35 g, 40.48 mM) under ice-cooling and the resulting mixture was stirred for 30 min. The cooling bath was removed and the reaction mixture was stirred for 2 h at room temperature additionally. To a suspension of (R)-(+)-2-methylpyrrolidine hydrochloride (5.42 g) which was synthesized in accordance with the method described in the literature (Tetrahedron, 27, 2599 (1971)) and triethylamine (8.46 ml, 60.72 mM) in THF (121 ml) was added the solution containing N-hydroxysuccinimide ester of the compound (46) at room temperature. The reaction mixture was stirred for additional 15 h. After the precipitation which appeared was filtered off, the filtrate was concentrated in vacuo. The residue (24.6 g) was subjected to gel filtration column chromatography (MCI Gel CHP-20P, 600 ml). The fractions eluting with 40% aqueous methanol were collected to give 8.87 g of the crude compound (I-57). After the crude compound was subjected to silica gel column chromatography (chloroform-methanol), the purified compound was freeze-dried to give 5.37 g (35.7%) of the compound (I-57).

mp: 192–194° C.

$[\alpha]_D = -1.9°$ (c=1.005, $H_2O$, 25° C.)

IR(KBr)$cm^{-1}$: 1755, 1675, 1625, 1541, 1516, 1448, 1232, 1097.

NMR($CD_3OD$): 8.97 (1H, t, J=2.1 Hz), 7.34 (1H, t, J=2.1 Hz), 5.19 and 5.04 (total 1H, each t, J=7.5 Hz), 4.92 (1H, dq, J=6.6 and 8.7 Hz), 4.36 and 4.35 (1H, d, J=8.7 Hz), 4.07 and 3.92 (total 1H, each m), 3.78 (1H, m), 3.42 (1H, m), 3.22 (2H, m), 1.5–2.0 (4H, m), 1.28 and 1.22 (total 3H, each d, J=6.6 Hz), 1.21 and 1.02 (total 3H, each d, J=6.6 Hz).

Elemental analysis ($C_{16}H_{22}N_4O_4S \cdot H_2O$) Calcd.: C,49.99; H,6.29; N,14.57; S,8.34. Found: C,49.99; H,6.29: N,14.79: S,8.36.

(Method B) To a solution of 10 g (33.41 mol) of the compound (46) and N-hydroxysuccinimide (4.04 g, 35.08 mM) in DMF (45 ml)-THF (360 ml) was added DCC (7.24 g, 35.08 mM) under ice-cooling and the resulting mixture was stirred for 4 h. To this reaction mixture was added a solution of (R)-(+)-2-methylpyrrolidine p-toluenesulfonate (8.6 g) which was synthesized in accordance with the method described in the literature (Helv. Chim. Acta, 34, 2202 (1951)) and triethylamine (9.32 mL 66.82 mmol) in THF (11 ml) under ice-cooling. After the mixture was stirred for 4 h at the same temperature, the cooling bath was removed and the mixture was stirred for 48 h. After the precipitation which appeared was filtered off, the filtrate was concentrated in vacuo. The residue (38 g) was dissolved in water (220 ml) and the precipitation which appeared was filtered off. The filtrate was subjected to gel column chromatography (MCI Gel CHP-20P, 600 ml). The fractions eluting with 40% aqueous methanol were collected and crystallized from water to give 6.94 g (56.7%) of the same compound (I-56) that the compound had been synthesized in Method A.

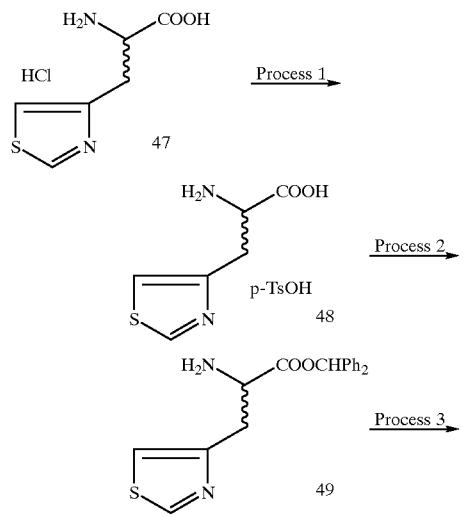

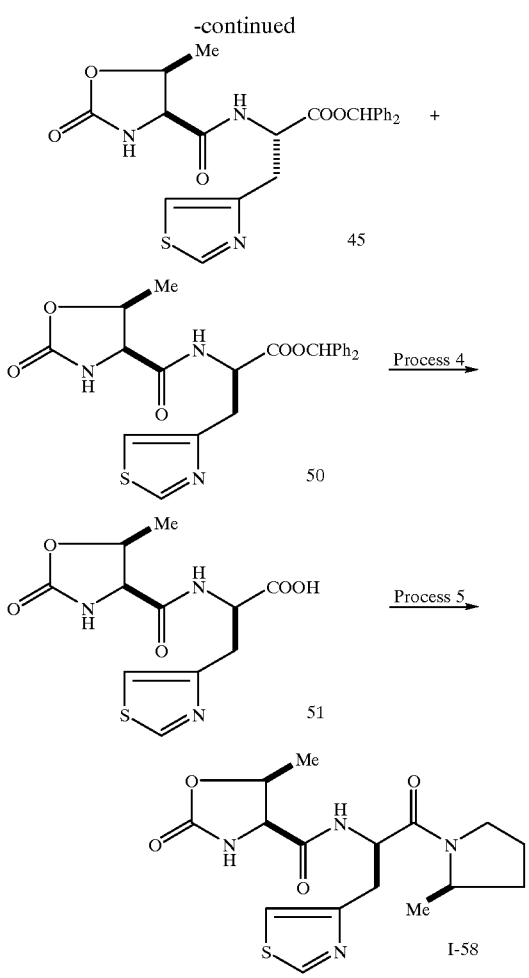

Example 58

Process 1

Preparation of 3-(4-thiazolyl)-DL-alanine p-toluenesulfonate (48)

17.16 g (70 mmol) of 3-(4-Thiazolyl)-DL-alanine hydrochloride (47) was dissolved in purified water (100 ml) and the resulting mixture was adsorbed on ion exchange resin Amberlite IR-120 B (Organo inc.) (120 ml, Type-H) column. The column was washed with water and the fractions eluting with ammonia water to yield the free base of the compound (47) (11.04 g).

NMR($D_2O$): 8.98(1H, d, J=1.8 Hz), 7.42 (1H, d, J=1.8 Hz), 4.08(1H, dd, J=4.8 and 7.8 Hz), 3.45 (1H, dd, J=4.8 and 15.3 Hz), 3.33 (1H, dd, J=7.8 and 15.3 Hz).

After the free base (11.04 g) was suspended in water (50 ml), to the suspension was added a solution of p-toluenesulfonic acid hydrate (12.19 g) in water (50 ml). The mixture was concentrated in vacuo to give syrupy residue (24.43 g). To the residue was added methanol (10 ml) and ether (300 ml) and the precipitated crystal was filtered off to give 21.84 g (98.9%) of the compound (48).

NMR($CD_3OD$): 9.00 (1H, d, J=2.1 Hz), 7.71 (2H, m), 7.46 (1H, J=2.1 Hz), 7.23 (2H, m), 4.37 (1H, dd, J=4.5 and 7.5 Hz), 3.50 (1H, dd, J=4.5 and 15.9 Hz), 3.38 (1H, dd, J=7.5 and 15.9 Hz), 2.36 (3H, s).

Example 58
Process 2

Preparation of 3-(4-thiazolyl)-DL-alanine diphenylmethyl ester p-toluenesulfonate (49)

After 21.84 g (123.6 mmol) of the compound (48) was dissolved in ethanol (200 ml) and THF (100 ml) with heating to the solution was added diphenyldiazomethane (24 g, 123.6 mmol) under ice-cooling over 35 min. little by little. The cooling bath was removed and the mixture was stirred for 1 h at room temperature. To the reaction mixture was added acetic acid (0.1 ml) for quenching the excess reagent, and the mixture was concentrated in vacuo. The residue was crystallized from ether and ethanol to yield 31.63 g (97.7%) of the compound (49).

mp: 148–149° C.

IR(KBr)cm$^{-1}$: 1755, 1607, 1516, 1493, 1216, 1202, 1181, 1125, 1088, 1066, 1036, 1011.

NMR(CD$_3$OD): 8.92 (1H, d, J=2.1 Hz), 7.70 (2H, m), 7.2–7.4 (13H, m), 6.91 (1H, s), 4.62 (1H, t, J=6 Hz), 3.47 (2H, d, J=6 Hz), 2.36 (3H, s).

Elemental analysis (C$_{26}$H$_{26}$N$_2$O$_5$S$_2$) Calcd.: C,61.16; H,5.13; N,5.49; S,12.56. Found: C,60.98; H,5.06; N,5.45; S,12.40.

Example 58
Process 3

Preparation of cis-L-5-methyl-2-oxo-oxazolidine-4-yl-carbonyl-3-(4-thiazolyl)-L-alanine diphenylmethyl ester (45) and cis-L-5-methyl-2-oxo-oxazolidine-4-carbonyl-3-(4-thiazolyl)-D-alanine diphenylmethyl ester (50)

In a manner similar to that described in the above process 3, cis-L-5-methyl-2-oxo-oxazoline-4-carboxylic acid (8.14 g, 56.07 mmol) was condensed with 28.63 g (56.07 mmol) of the compound (49) using DCC (12.15 g, 68.87 mmol) in the presence of N-hydroxybenzotriazole (1.52 g, 11.21 mmol) and triethylamine (8.21 ml, 58.87 mmol) in the mixed solvents of DMF (100 ml)-THF (680 ml). After the precipitation which appeared was filtered off the filtrate was concentrated in vacuo. The residue was dissolved in ethyl acetate (400 ml) with heating and the precipitation which appeared was filtered off. The filtrate was washed with sodium carbonate aq. and water. After the ethyl acetate layer was stood overnight and the precipitated crystal was filtered off, the crystal was recrystallized from ethyl acetate-methanol to give 4.6 g (17.6%) of the compound (50).

mp: 203–204° C.

[α]$_D$=+27.5° (c=1, DMF, 22° C.) IR(KBr)cm$^{-1}$: 1754, 1738, 1664, 1523, 1381, 1228, 1207, 1171, 1100.

NMR(DMSO-d6): 9.02 (1H, d, J=1.8 Hz), 8.67 (1H, d, J=7.8 Hz), 7.82 (1H, s) 7.2–7.4 (1H, m), 6.79 (1H, s), 5.00 (1H, m), 4.68 (1H, m), 4.19 (1H, d, J=8.4 Hz), 3.2–3.4 (1H, M), 3.16 (1H, dd, J=9.3 and 14.4 Hz), 0.81 (3H, d, J=6.3 Hz).

Elemental analysis (C$_{24}$H$_{23}$N$_3$O$_5$S) Calcd.: C,61.92; H,4.98; N,9.03: S,6.89. Found: C,61.60; H,5.04; N,9.22; S,6.96.

The mother liquor which was obtained by collecting the crystals was concentrated in vacuo, the precipitated crystal was filtered off to give 17.26 g (76.1%) of the mixture of the compounds (50) and (45). The mixture was crystallized from methanol-ethyl acetate to yield 3.92 g (15%) of the compound (50). After the mother liquor was concentrated in vacuo, the residue was crystallized from acetone-ether to give 6.21 g (23.7%) of the same compound (45) that the compound had been synthesized in Example 57—process 3.

Example 58
Process 4

Preparation of cis-L-5-methyl-2-oxo-oxazolidine-4-yl-carbonyl-3-(4-thiazolyl)-D-alanine (51)

In a manner similar to that described in the method of Example 57—process 4, 4.1 g (8.81 mmol) of the compound (50) was de-diphenylmethylesterificated by treating with trifluoroacetic acid-anisole to give 206 g (78.3%) of the compound (51).

mp: 214° C.

[α]$_D$=+6.9° (c=0.5, DMF, 22° C.) IR(KBr)cm$^{-1}$: 1753, 1708, 1657, 1560, 1413, 1343, 1280, 1241, 1175, 1095.

NMR(DMSO-d6): 9.02 (1H, d, J=2.1 Hz), 8.46 (1H, d, J=8.1 Hz), 7.78 (1H, s), 7.40 (1H, d, J=8.4 Hz), 4.6–4.8 (2H, m), 4.18 (1H, d, J=8.4 Hz), 3.25 (1H, dd, J=4.2 and 15 Hz), 3.10 (1H, dd, J=9.9 Hz and 15 Hz), 0.80 (3H, d, J=6.6 Hz).

Elemental analysis (C$_{11}$H$_{13}$N$_3$O$_5$S) Calcd.: C,44.14; H,4.38; N,14.04; S,10.71. Found: C,44.08; H,4.39; N,14.04; S,10.71.

Example 58
Process 5

Preparation of cis-L-5-methyl-2-oxo-oxazolidine-4-yl-carbonyl-3-(4-thiazolyl)-D-alanyl-2(R)-methylpyrrolidine (I-58)

In a manner similar to that described in the method of Example 57—process 5, the compound (51) was condensed with 2(R)-methylpyrrolidine p-toluenesulfonate in the presence of N-hydroxysuccinimide, DCC, and triethylamine in DMF-THF to give the compound (I-58).

mp: 170–172° C.

[α]$_D$=−16.2° (c=1.014, MeOH, 25° C.)

IR(KBr)cm$^{-1}$: 1749, 1661, 1637, 1538, 1441, 1381, 1264.

NMR(CD$_3$OD): 8.97 (1H, t, J=2.1 Hz), 7.34 (1H, t, J=2.1 Hz), 5.19 and 5.04 (total 1H, each t, J=7.5 Hz), 4.92 (1H, dq, J=6.6 and 8.7 Hz), 4.36 and 4.35 (1H, d, J=8.7 Hz), 4.07 and 3.92 (total 1H, each m), 3.78 (1H, m), 3.42 (1H, m), 3.22 (2H, m), 1.5–2.0 (4H, m), 1.28 and 1.22 (total 3H, each d, J=6.6 Hz), 1.21 and 1.02 (total 3H, each d, J=6.6 Hz).

Elemental analysis (C$_{16}$H$_{22}$N$_4$O$_4$S H$_2$O) Calcd.: C,49.99; H,6.29; N,14.57; S,8.34. Found: C,52.40; H,5.98; N,15.19; S,8.77.

In a manner similar to that, described in the method of the above, the compounds below may be able to be synthesized.

TABLE 24

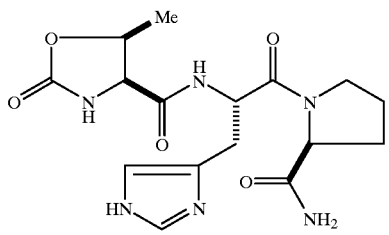

| Example No. | Y | Example No. | Y |
|---|---|---|---|
| 59 | Et | 83 | —CONHMe |
| 60 | n-Pr | 84 | —CON(Me)₂ |
| 61 | i-Pr | 85 | —CON(Me)(Et) |
| 62 | c-Pr | 86 | —CON(Et)₂ |
| 63 | n-Bu | 87 | —CH₂-(c-Pr) |
| 64 | sec-Bu | 88 | —CH₂-(c-Bu) |
| 65 | i-Bu | 89 | —CH₂-(c-Pen) |
| 66 | t-Bu | 90 | —CH₂-(c-Hex) |
| 67 | c-Bu | 91 | —CH₂CN |
| 68 | n-Pen | 92 | —CH₂CHO |
| 69 | c-Pen | 93 | —CH₂COOH |
| 70 | n-Hex | 94 | —CH₂COOMe |
| 71 | c-Hex | 95 | —CH₂COOEt |
| 72 | —COOMe | 96 | —CH₂COO(n-Pr) |
| 73 | —COOEt | 97 | —CH₂COO(i-Pr) |
| 74 | —COO(n-Pr) | 98 | —CH₂COO(c-Pr) |
| 75 | —COO(c-Pr) | 99 | —CH₂CF₃ |
| 76 | —COO(n-Bu) | 100 | —CH₂CONH₂ |
| 77 | —COO(c-Bu) | 101 | —CH₂C(O)CH₃ |
| 78 | —COO(c-Pen) | 102 | —CH₂C(O)Et |
| 79 | —COO(c-Hex) | 103 | —CH₂C(O)Pr |
| 80 | —COO(n-Dec) | 104 | —CH₂Ph |
| 81 | —COO(4-Me-Ph) | 105 | —CH₂(4-Me-Ph) |
| 82 | —COOPh | 106 | —CH₂SH |

TABLE 25

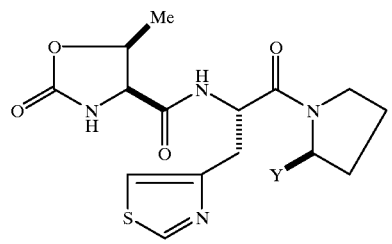

| Example No. | Y | Example No. | Y |
|---|---|---|---|
| 107 | —CH₂SMe | 131 | —CH₂PO(OH)₂ |
| 108 | —CH₂NO₂ | 132 | —CH₂PO(OH) |
| 109 | —CH₂NH₂ | 133 | —CH₂PO(OMe)₂ |
| 110 | —CH₂NHMe | 134 | —CH₂CH₂OH |
| 111 | —CH₂N(Me)₂ | 135 | —CH₂CH₂OMe |
| 112 | —CH₂N(Me)(Et) | 136 | —CH₂CH₂CN |
| 113 | —CH₂OC(O)CH₃ | 137 | —CH₂CH₂CHO |
| 114 | —CH₂OC(O)Et | 138 | —CH₂CH₂COOH |
| 115 | —CH₂OC(O)Ph | 139 | —CH₂CH₂COOMe |
| 116 | —CH₂OMe | 140 | —CH₂CH₂CONH₂ |
| 117 | —CH₂OEt | 141 | —CH₂CH₂NO₂ |
| 118 | —CH₂O(n-Pr) | 142 | —(CH₂)₃CN |
| 119 | —CH₂O(c-Pr) | 143 | —(CH₂)₃CHO |
| 120 | —CH₂O(n-Bu) | 144 | —(CH₂)₃COOH |
| 121 | —CH₂O(t-Bu) | 145 | —(CH₂)₃COOMe |
| 122 | —CH₂O(c-Pen) | 146 | —(CH₂)₃CONH₂ |
| 123 | —CH₂O(c-Hex) | 147 | —(CH₂)₃NO₂ |
| 124 | —CH₂OPh | 148 | —CH₂-(1-Pyrrolidinyl) |
| 125 | —CH₂SO₃H | 149 | —CO-(1-Piperidyl) |
| 126 | —CH₂SO₃Me | 150 | —CO-(1-Piperazinyl) |
| 127 | —CH₂SO₂Me | 151 | —CO-(1-Pyrrolyl) |

TABLE 25-continued

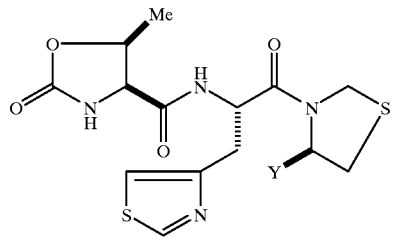

| Example No. | Y | Example No. | Y |
|---|---|---|---|
| 128 | —CH₂SO₂Ph | 152 | —CO-(1-Imidazolizinyl) |
| 129 | —CH₂SOMe | 153 | —CO-(1-Indolyl) |
| 130 | —CH₂SOEt | 154 | —CO-(1-Imidazolyl) |

TABLE 26

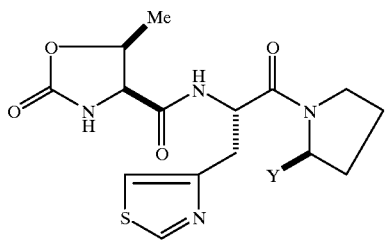

| Example No. | Y | Example No. | Y |
|---|---|---|---|
| 155 | Me | 179 | —CH₂CN |
| 156 | Et | 180 | —CH₂CHO |
| 157 | n-Pr | 181 | —CH₂COOH |
| 158 | i-Pr | 182 | —CH₂COOMe |
| 159 | c-Pr | 183 | —CH₂COOEt |
| 160 | n-Bu | 184 | —CH₂COO(n-Pr) |
| 161 | i-Bu | 185 | —CH₂COO(i-Pr) |
| 162 | sec-Bu | 186 | —CH₂COO(c-Pr) |
| 163 | c-Bu | 187 | —CH₂COOPh |
| 164 | n-Pen | 188 | —CH₂CONH₂ |
| 165 | c-Pen | 189 | —CH₂C(O)CH₃ |
| 166 | n-Hex | 190 | —CH₂C(O)Et |
| 167 | c-Hex | 191 | —CH₂C(O)Pr |
| 168 | —COOMe | 192 | —CH₂SH |
| 169 | —COOEt | 193 | —CH₂SMe |
| 170 | —COO(n-Pr) | 194 | —CH₂NO₂ |
| 171 | —COO(c-Pr) | 195 | —CH₂NH₂ |
| 172 | —COO(n-Bu) | 196 | —CH₂NHMe |
| 173 | —COO(c-Bu) | 197 | —CH₂N(Me)₂ |
| 174 | —COO(c-Pen) | 198 | —CH₂OC(O)CH₃ |
| 175 | —COO(c-Hex) | 199 | —CH₂OC(O)Et |
| 176 | —CONHMe | 200 | —CH₂OC(O)Ph |
| 177 | —CON(Me)₂ | 201 | —CH₂-(1-Pyrrolidinyl) |
| 178 | —CON(Me)(Et) | 202 | —CO-(1-Piperidyl) |

TABLE 27

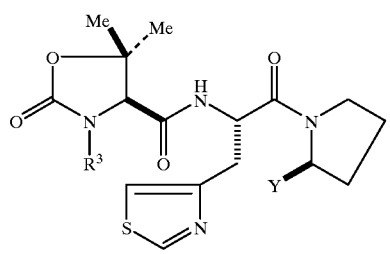

| Example No. | R³ | Y | Example No. | R³ | Y |
|---|---|---|---|---|---|
| 203 | H | Me | 227 | Me | Me |
| 204 | H | Et | 228 | Me | Et |
| 205 | H | n-Pr | 229 | Me | n-Pr |
| 206 | H | i-Pr | 230 | Me | i-Pr |
| 207 | H | c-Pr | 231 | Me | c-Pr |
| 208 | H | n-Bu | 232 | Me | n-Bu |
| 209 | H | i-Bu | 233 | Me | i-Bu |
| 210 | H | sec-Bu | 234 | Me | sec-Bu |
| 211 | H | t-Bu | 235 | Me | t-Bu |
| 212 | H | —COOH | 236 | Me | —COOH |
| 213 | H | —COOMe | 237 | Me | —COOMe |
| 214 | H | —CONH₂ | 238 | Me | —CONH₂ |
| 215 | H | —CONHMe | 239 | Me | —CONHMe |
| 216 | H | —CN | 240 | Me | —CN |
| 217 | H | —CH₂OH | 241 | Me | —CH₂OH |
| 218 | H | —CH₂OMe | 242 | Me | —CH₂OMe |
| 219 | H | —CH₂COOH | 243 | Me | —CH₂COOH |
| 220 | H | —CH₂COOMe | 244 | Me | —CH₂COOMe |
| 221 | H | —CH₂COPh | 245 | Me | —CH₂COPh |
| 222 | H | —CH₂CONH₂ | 246 | Me | —CH₂CONH₂ |
| 223 | H | —CH₂CN | 247 | Me | —CH₂CN |
| 224 | H | —CH₂CHO | 248 | Me | —CH₂CHO |
| 225 | H | —CH₂CF₃ | 249 | Me | —CH₂CF₃ |
| 226 | H | —CH₂SH | 250 | Me | —CH₂SH |

TABLE 28

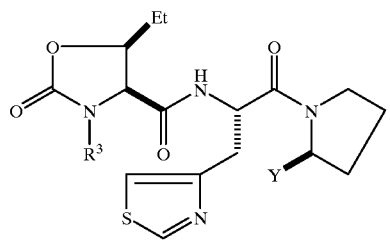

| Example No. | R³ | Y | Example No. | R³ | Y |
|---|---|---|---|---|---|
| 251 | H | Me | 275 | Me | Me |
| 252 | H | Et | 276 | Me | Et |
| 253 | H | n-Pr | 277 | Me | n-Pr |
| 254 | H | i-Pr | 278 | Me | i-Pr |
| 255 | H | c-Pr | 279 | Me | c-Pr |
| 256 | H | n-Bu | 280 | Me | n-Bu |
| 257 | H | i-Bu | 281 | Me | i-Bu |
| 258 | H | sec-Bu | 282 | Me | sec-Bu |
| 259 | H | t-Bu | 283 | Me | t-Bu |
| 260 | H | —COOH | 284 | Me | —COOH |
| 261 | H | —COOMe | 285 | Me | —COOMe |
| 262 | H | —CONH₂ | 286 | Me | —CONH₂ |
| 263 | H | —CONHMe | 287 | Me | —CONHMe |
| 264 | H | —CN | 288 | Me | —CN |
| 265 | H | —CH₂OH | 289 | Me | —CH₂OH |
| 266 | H | —CH₂OMe | 290 | Me | —CH₂OMe |
| 267 | H | —CH₂COOH | 291 | Me | —CH₂COOH |
| 268 | H | —CH₂COOMe | 292 | Me | —CH₂COOMe |

TABLE 28-continued

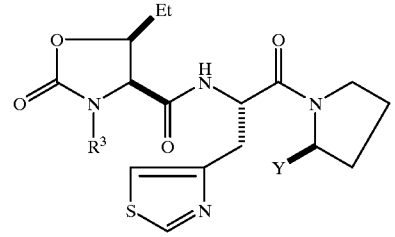

| Example No. | R³ | Y | Example No. | R³ | Y |
|---|---|---|---|---|---|
| 269 | H | —CH₂COPh | 293 | Me | —CH₂COPh |
| 270 | H | —CH₂CONH₂ | 294 | Me | —CH₂CONH₂ |
| 271 | H | —CH₂CN | 295 | Me | —CH₂CN |
| 272 | H | —CH₂CHO | 296 | Me | —CH₂CHO |
| 273 | H | —CH₂CF₃ | 297 | Me | —CH₂CF₃ |
| 274 | H | —CH₂SH | 298 | Me | —CH₂SH |

TABLE 29

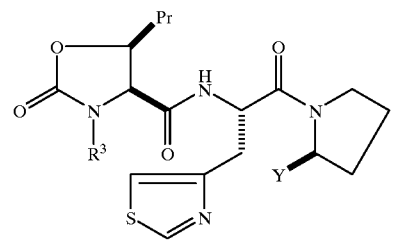

| Example No. | R³ | Y | Example No. | R³ | Y |
|---|---|---|---|---|---|
| 299 | H | Me | 323 | Me | Me |
| 300 | H | Et | 324 | Me | Et |
| 301 | H | n-Pr | 325 | Me | n-Pr |
| 302 | H | i-Pr | 326 | Me | i-Pr |
| 303 | H | c-Pr | 327 | Me | c-Pr |
| 304 | H | n-Bu | 328 | Me | n-Bu |
| 305 | H | i-Bu | 329 | Me | i-Bu |
| 306 | H | sec-Bu | 330 | Me | sec-Bu |
| 307 | H | t-Bu | 331 | Me | t-Bu |
| 308 | H | —COOH | 332 | Me | —COOH |
| 309 | H | —COOMe | 333 | Me | —COOMe |
| 310 | H | —CONH₂ | 334 | Me | —CONH₂ |
| 311 | H | —CONHMe | 335 | Me | —CONHMe |
| 312 | H | —CN | 336 | Me | —CN |
| 313 | H | —CH₂OH | 337 | Me | —CH₂OH |
| 314 | H | —CH₂OMe | 338 | Me | —CH₂OMe |
| 315 | H | —CH₂COOH | 339 | Me | —CH₂COOH |
| 316 | H | —CH₂COOMe | 340 | Me | —CH₂COOMe |
| 317 | H | —CH₂COPh | 341 | Me | —CH₂COPh |
| 318 | H | —CH₂CONH₂ | 342 | Me | —CH₂CONH₂ |
| 319 | H | —CH₂CN | 343 | Me | —CH₂CN |
| 320 | H | —CH₂CHO | 345 | Me | —CH₂CHO |
| 321 | H | —CH₂CF₃ | 346 | Me | —CH₂CF₃ |
| 322 | H | —CH₂SH | 347 | Me | —CH₂SH |

TABLE 30

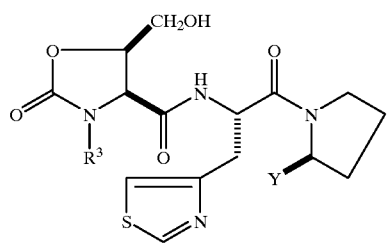

| Example No. | R³ | Y | Example No. | R³ | Y |
|---|---|---|---|---|---|
| 348 | H | Me | 372 | Me | Me |
| 349 | H | Et | 373 | Me | Et |
| 350 | H | n-Pr | 374 | Me | n-Pr |
| 351 | H | i-Pr | 375 | Me | i-Pr |
| 352 | H | c-Pr | 376 | Me | c-Pr |
| 353 | H | n-Bu | 377 | Me | n-Bu |
| 354 | H | i-Bu | 378 | Me | i-Bu |
| 355 | H | sec-Bu | 379 | Me | sec-Bu |
| 356 | H | t-Bu | 380 | Me | t-Bu |
| 357 | H | —COOH | 381 | Me | —COOH |
| 358 | H | —COOMe | 382 | Me | —COOMe |
| 359 | H | —CONH₂ | 383 | Me | —CONH₂ |
| 360 | H | —CONHMe | 384 | Me | —CONHMe |
| 361 | H | —CN | 385 | Me | —CN |
| 362 | H | —CH₂OH | 386 | Me | —CH₂OH |
| 363 | H | —CH₂OMe | 387 | Me | —CH₂OMe |
| 364 | H | —CH₂COOH | 388 | Me | —CH₂COOH |
| 365 | H | —CH₂COOMe | 389 | Me | —CH₂COOMe |
| 366 | H | —CH₂COPh | 390 | Me | —CH₂COPh |
| 367 | H | —CH₂CONH₂ | 391 | Me | —CH₂CONH₂ |
| 368 | H | —CH₂CN | 392 | Me | —CH₂CN |
| 369 | H | —CH₂CHO | 393 | Me | —CH₂CHO |
| 370 | H | —CH₂CF₃ | 394 | Me | —CH₂CF₃ |
| 371 | H | —CH₂SH | 395 | Me | —CH₂SH |

TABLE 31

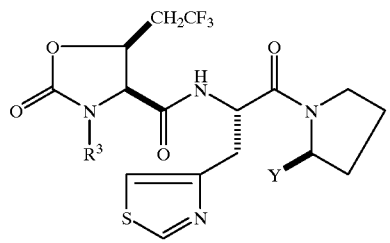

| Example No. | R³ | Y | Example No. | R³ | Y |
|---|---|---|---|---|---|
| 396 | H | Me | 420 | Me | Me |
| 397 | H | Et | 421 | Me | Et |
| 398 | H | n-Pr | 422 | Me | n-Pr |
| 399 | H | i-Pr | 423 | Me | i-Pr |
| 400 | H | c-Pr | 424 | Me | c-Pr |
| 401 | H | n-Bu | 425 | Me | n-Bu |
| 402 | H | i-Bu | 426 | Me | i-Bu |
| 403 | H | sec-Bu | 427 | Me | sec-Bu |
| 404 | H | t-Bu | 428 | Me | t-Bu |
| 405 | H | —COOH | 429 | Me | —COOH |
| 406 | H | —COOMe | 430 | Me | —COOMe |
| 407 | H | —CONH₂ | 431 | Me | —CONH₂ |
| 408 | H | —CONHMe | 432 | Me | —CONHMe |
| 409 | H | —CN | 433 | Me | —CN |
| 410 | H | —CH₂OH | 434 | Me | —CH₂OH |
| 411 | H | —CH₂OMe | 435 | Me | —CH₂OMe |
| 412 | H | —CH₂COOH | 436 | Me | —CH₂COOH |
| 413 | H | —CH₂COOMe | 437 | Me | —CH₂COOMe |

TABLE 31-continued

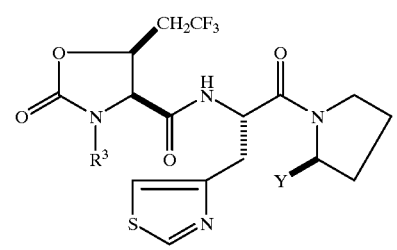

| Example No. | R³ | Y | Example No. | R³ | Y |
|---|---|---|---|---|---|
| 414 | H | —CH₂COPh | 438 | Me | —CH₂COPh |
| 415 | H | —CH₂CONH₂ | 439 | Me | —CH₂CONH₂ |
| 416 | H | —CH₂CN | 440 | Me | —CH₂CN |
| 417 | H | —CH₂CHO | 441 | Me | —CH₂CHO |
| 418 | H | —CH₂CF₃ | 442 | Me | —CH₂CF₃ |
| 419 | H | —CH₂SH | 443 | Me | —CH₂SH |

TABLE 32

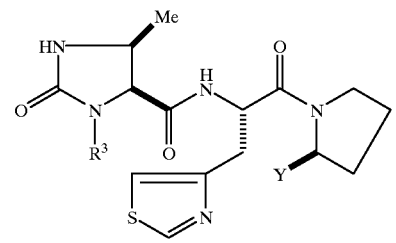

| Example No. | R³ | Y | Example No. | R³ | Y |
|---|---|---|---|---|---|
| 444 | H | Me | 468 | Me | Me |
| 445 | H | Et | 469 | Me | Et |
| 446 | H | n-Pr | 470 | Me | n-Pr |
| 447 | H | i-Pr | 471 | Me | i-Pr |
| 448 | H | c-Pr | 472 | Me | c-Pr |
| 449 | H | n-Bu | 473 | Me | n-Bu |
| 450 | H | i-Bu | 474 | Me | i-Bu |
| 451 | H | sec-Bu | 475 | Me | sec-Bu |
| 452 | H | t-Bu | 476 | Me | t-Bu |
| 453 | H | —COOH | 477 | Me | —COOH |
| 454 | H | —COOMe | 478 | Me | —COOMe |
| 455 | H | —CONH₂ | 479 | Me | —CONH₂ |
| 456 | H | —CONHMe | 480 | Me | —CONHMe |
| 457 | H | —CN | 481 | Me | —CN |
| 458 | H | —CH₂OH | 482 | Me | —CH₂OH |
| 459 | H | —CH₂OMe | 483 | Me | —CH₂OMe |
| 460 | H | —CH₂COOH | 484 | Me | —CH₂COOH |
| 461 | H | —CH₂COOMe | 485 | Me | —CH₂COOMe |
| 462 | H | —CH₂COPh | 486 | Me | —CH₂COPh |
| 463 | H | —CH₂CONH₂ | 487 | Me | —CH₂CONH₂ |
| 464 | H | —CH₂CN | 488 | Me | —CH₂CN |
| 465 | H | —CH₂CHO | 489 | Me | —CH₂CHO |
| 466 | H | —CH₂CF₃ | 490 | Me | —CH₂CF₃ |
| 467 | H | —CH₂SH | 491 | Me | —CH₂SH |

TABLE 33

| Example No. | R³ | Y | Example No. | R³ | Y |
|---|---|---|---|---|---|
| 492 | H | Me | 516 | Me | Me |
| 493 | H | Et | 517 | Me | Et |
| 494 | H | n-Pr | 518 | Me | n-Pr |
| 495 | H | i-Pr | 519 | Me | i-Pr |
| 496 | H | c-Pr | 520 | Me | c-Pr |
| 497 | H | n-Bu | 521 | Me | n-Bu |
| 498 | H | i-Bu | 522 | Me | i-Bu |
| 499 | H | sec-Bu | 523 | Me | sec-Bu |
| 500 | H | t-Bu | 524 | Me | t-Bu |
| 501 | H | —COOH | 525 | Me | —COOH |
| 502 | H | —COOMe | 526 | Me | —COOMe |
| 503 | H | —CONH₂ | 527 | Me | —CONH₂ |
| 504 | H | —CONHMe | 528 | Me | —CONHMe |
| 505 | H | —CN | 529 | Me | —CN |
| 506 | H | —CH₂OH | 530 | Me | —CH₂OH |
| 507 | H | —CH₂OMe | 531 | Me | —CH₂OMe |
| 508 | H | —CH₂COOH | 532 | Me | —CH₂COOH |
| 509 | H | —CH₂COOMe | 533 | Me | —CH₂COOMe |
| 510 | H | —CH₂COPh | 534 | Me | —CH₂COPh |
| 511 | H | —CH₂CONH₂ | 535 | Me | —CH₂CONH₂ |
| 512 | H | —CH₂CN | 536 | Me | —CH₂CN |
| 513 | H | —CH₂CHO | 537 | Me | —CH₂CHO |
| 514 | H | —CH₂CF₃ | 538 | Me | —CH₂CF₃ |
| 515 | H | —CH₂SH | 539 | Me | —CH₂SH |

TABLE 34

| Example No. | R³ | Y | Example No. | R³ | Y |
|---|---|---|---|---|---|
| 540 | H | Me | 564 | Me | Me |
| 541 | H | Et | 565 | Me | Et |
| 542 | H | n-Pr | 566 | Me | n-Pr |
| 543 | H | i-Pr | 567 | Me | i-Pr |
| 544 | H | c-Pr | 568 | Me | c-Pr |
| 545 | H | n-Bu | 569 | Me | n-Bu |
| 546 | H | i-Bu | 570 | Me | i-Bu |
| 547 | H | sec-Bu | 571 | Me | sec-Bu |
| 548 | H | t-Bu | 572 | Me | t-Bu |
| 549 | H | —COOH | 573 | Me | —COOH |
| 550 | H | —COOMe | 574 | Me | —COOMe |
| 551 | H | —CONH₂ | 575 | Me | —CONH₂ |
| 552 | H | —CONHMe | 576 | Me | —CONHMe |
| 553 | H | —CN | 577 | Me | —CN |
| 554 | H | —CH₂OH | 578 | Me | —CH₂OH |
| 555 | H | —CH₂OMe | 579 | Me | —CH₂OMe |
| 556 | H | —CH₂COOH | 580 | Me | —CH₂COOH |
| 557 | H | —CH₂COOMe | 581 | Me | —CH₂COOMe |
| 558 | H | —CH₂COPh | 582 | Me | —CH₂COPh |
| 559 | H | —CH₂CONH₂ | 583 | Me | —CH₂CONH₂ |
| 560 | H | —CH₂CN | 584 | Me | —CH₂CN |
| 561 | H | —CH₂CHO | 585 | Me | —CH₂CHO |
| 562 | H | —CH₂CF₃ | 586 | Me | —CH₂CF₃ |
| 563 | H | —CH₂SH | 587 | Me | —CH₂SH |

TABLE 35

| Example No. | R³ | Y | Example No. | R³ | Y |
|---|---|---|---|---|---|
| 588 | H | Me | 612 | Me | Me |
| 589 | H | Et | 613 | Me | Et |
| 590 | H | n-Pr | 614 | Me | n-Pr |
| 591 | H | i-Pr | 615 | Me | i-Pr |
| 592 | H | c-Pr | 616 | Me | c-Pr |
| 593 | H | n-Bu | 617 | Me | n-Bu |
| 594 | H | i-Bu | 618 | Me | i-Bu |
| 595 | H | sec-Bu | 619 | Me | sec-Bu |
| 596 | H | t-Bu | 620 | Me | t-Bu |
| 597 | H | —COOH | 621 | Me | —COOH |
| 598 | H | —COOMe | 622 | Me | —COOMe |
| 599 | H | —CONH₂ | 623 | Me | —CONH₂ |
| 600 | H | —CONHMe | 624 | Me | —CONHMe |
| 601 | H | —CN | 625 | Me | —CN |
| 602 | H | —CH₂OH | 626 | Me | —CH₂OH |
| 603 | H | —CH₂OMe | 627 | Me | —CH₂OMe |
| 604 | H | —CH₂COOH | 628 | Me | —CH₂COOH |
| 605 | H | —CH₂COOMe | 629 | Me | —CH₂COOMe |
| 606 | H | —CH₂COPh | 630 | Me | —CH₂COPh |
| 607 | H | —CH₂CONH₂ | 631 | Me | —CH₂CONH₂ |
| 608 | H | —CH₂CN | 632 | Me | —CH₂CN |
| 609 | H | —CH₂CHO | 633 | Me | —CH₂CHO |
| 610 | H | —CH₂CF₃ | 634 | Me | —CH₂CF₃ |
| 611 | H | —CH₂SH | 635 | Me | —CH₂SH |

TABLE 36

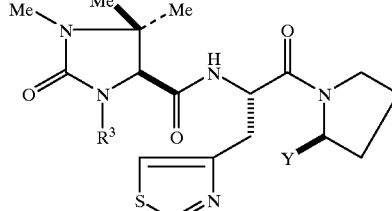

| Example No. | R³ | Y | Example No. | R³ | Y |
|---|---|---|---|---|---|
| 636 | H | Me | 661 | Me | Me |
| 637 | H | Et | 662 | Me | Et |
| 638 | H | n-Pr | 663 | Me | n-Pr |
| 639 | H | i-Pr | 664 | Me | i-Pr |
| 640 | H | c-Pr | 665 | Me | c-Pr |
| 641 | H | n-Bu | 666 | Me | n-Pu |
| 642 | H | i-Bu | 667 | Me | i-Bu |
| 643 | H | sec-Bu | 668 | Me | sec-Bu |
| 645 | H | t-Bu | 669 | Me | t-Bu |
| 646 | H | —COOH | 670 | Me | —COOH |
| 647 | H | —COOMe | 671 | Me | —COOMe |
| 648 | H | —CONH₂ | 672 | Me | —CONH₂ |
| 649 | H | —CONHMe | 673 | Me | —CONHMe |
| 650 | H | —CN | 674 | Me | —CN |
| 651 | H | —CH₂OH | 675 | Me | —CH₂OH |
| 652 | H | —CH₂OMe | 676 | Me | —CH₂OMe |
| 653 | H | —CH₂COOH | 677 | Me | —CH₂COOH |
| 654 | H | —CH₂COOMe | 678 | Me | —CH₂COOMe |
| 655 | H | —CH₂COPh | 679 | Me | —CH₂COPh |
| 656 | H | —CH₂CONH₂ | 680 | Me | —CH₂CONH₂ |
| 657 | H | —CH₂CN | 681 | Me | —CH₂CN |
| 658 | H | —CH₂CHO | 682 | Me | —CH₂CHO |
| 659 | H | —CH₂CF₃ | 683 | Me | —CH₂CF₃ |
| 660 | H | —CH₂SH | 684 | Me | —CH₂SH |

TABLE 37

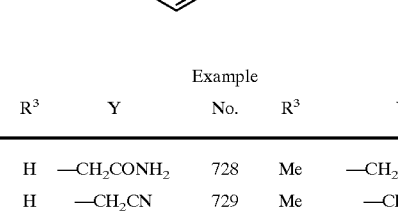

| Example No. | R³ | Y | Example No. | R³ | Y |
|---|---|---|---|---|---|
| 685 | H | Me | 709 | Me | Me |
| 686 | H | Et | 710 | Me | Et |
| 687 | H | n-Pr | 711 | Me | n-Pr |
| 688 | H | i-Pr | 712 | Me | i-Pr |
| 689 | H | c-Pr | 713 | Me | c-Pr |
| 690 | H | n-Bu | 714 | Me | n-Bu |
| 691 | H | i-Bu | 715 | Me | i-Bu |
| 692 | H | sec-Bu | 716 | Me | sec-Bu |
| 693 | H | t-Bu | 717 | Me | t-Bu |
| 694 | H | —COOH | 718 | Me | —COOH |
| 695 | H | —COOMe | 719 | Me | —COOMe |
| 696 | H | —CONH₂ | 720 | Me | —CONH₂ |
| 697 | H | —CONHMe | 721 | Me | —CONHMe |
| 698 | H | —CN | 722 | Me | —CN |
| 699 | H | —CH₂OH | 723 | Me | —CH₂OH |
| 700 | H | —CH₂OMe | 724 | Me | —CH₂OMe |
| 701 | H | —CH₂COOH | 725 | Me | —CH₂COOH |
| 702 | H | —CH₂COOMe | 726 | Me | —CH₂COOMe |
| 703 | H | —CH₂COPh | 727 | Me | —CH₂COPh |

TABLE 37-continued

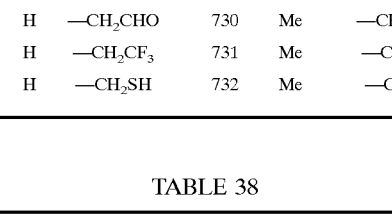

| Example No. | R³ | Y | Example No. | R³ | Y |
|---|---|---|---|---|---|
| 704 | H | —CH₂CONH₂ | 728 | Me | —CH₂CONH₂ |
| 705 | H | —CH₂CN | 729 | Me | —CH₂CN |
| 706 | H | —CH₂CHO | 730 | Me | —CH₂CHO |
| 707 | H | —CH₂CF₃ | 731 | Me | —CH₂CF₃ |
| 708 | H | —CH₂SH | 732 | Me | —CH₂SH |

TABLE 38

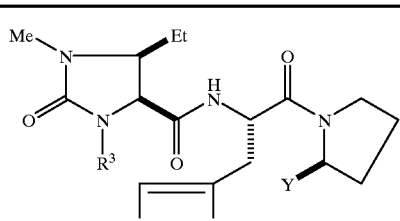

| Example No. | R³ | Y | Example No. | R³ | Y |
|---|---|---|---|---|---|
| 733 | H | Me | 757 | Me | Me |
| 734 | H | Et | 758 | Me | Et |
| 735 | H | n-Pr | 759 | Me | n-Pr |
| 736 | H | i-Pr | 760 | Me | i-Pr |
| 737 | H | c-Pr | 761 | Me | c-Pr |
| 738 | H | n-Bu | 762 | Me | n-Bu |
| 739 | H | i-Bu | 763 | Me | i-Bu |
| 740 | H | sec-Bu | 764 | Me | sec-Bu |
| 741 | H | t-Bu | 765 | Me | t-Bu |
| 742 | H | —COOH | 766 | Me | —COOH |
| 743 | H | —COOMe | 767 | Me | —COOMe |
| 744 | H | —CONH₂ | 768 | Me | —CONH₂ |
| 745 | H | —CONHMe | 769 | Me | —CONHMe |
| 746 | H | —CN | 770 | Me | —CN |
| 747 | H | —CH₂OH | 771 | Me | —CH₂OH |
| 748 | H | —CH₂OMe | 772 | Me | —CH₂OMe |
| 749 | H | —CH₂COOH | 773 | Me | —CH₂COOH |
| 750 | H | —CH₂COOMe | 774 | Me | —CH₂COOMe |
| 751 | H | —CH₂COPh | 775 | Me | —CH₂COPh |
| 752 | H | —CH₂CONH₂ | 776 | Me | —CH₂CONH₂ |
| 753 | H | —CH₂CN | 777 | Me | —CH₂CN |
| 754 | H | —CH₂CHO | 778 | Me | —CH₂CHO |
| 755 | H | —CH₂CF₃ | 779 | Me | —CH₂CF₃ |
| 756 | H | —CH₂SH | 780 | Me | —CH₂SH |

TABLE 39

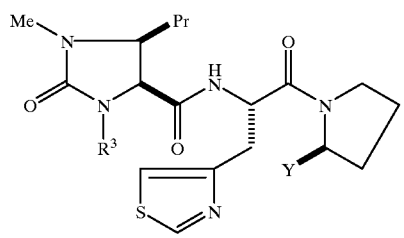

| Example No. | R³ | Y | Example No. | R³ | Y |
|---|---|---|---|---|---|
| 781 | H | Me | 805 | Me | Me |
| 782 | H | Et | 806 | Me | Et |
| 783 | H | n-Pr | 807 | Me | n-Pr |
| 784 | H | i-Pr | 808 | Me | i-Pr |
| 785 | H | c-Pr | 809 | Me | c-Pr |
| 786 | H | n-Bu | 810 | Me | n-Bu |
| 787 | H | i-Bu | 811 | Me | i-Bu |
| 788 | H | sec-Bu | 812 | Me | sec-Bu |
| 789 | H | t-Bu | 813 | Me | t-Bu |
| 790 | H | —COOH | 814 | Me | —COOH |
| 791 | H | —COOMe | 815 | Me | —COOMe |
| 792 | H | —CONH₂ | 816 | Me | —CONH₂ |
| 793 | H | —CONHMe | 817 | Me | —CONHMe |
| 794 | H | —CN | 818 | Me | —CN |
| 795 | H | —CH₂OH | 819 | Me | —CH₂OH |
| 796 | H | —CH₂OMe | 820 | Me | —CH₂OMe |
| 797 | H | —CH₂COOH | 821 | Me | —CH₂COOH |
| 798 | H | —CH₂COOMe | 822 | Me | —CH₂COOMe |
| 799 | H | —CH₂COPh | 823 | Me | —CH₂COPh |
| 800 | H | —CH₂CONH₂ | 824 | Me | —CH₂CONH₂ |
| 801 | H | —CH₂CN | 825 | Me | —CH₂CN |
| 802 | H | —CH₂CHO | 826 | Me | —CH₂CHO |
| 803 | H | —CH₂CF₃ | 827 | Me | —CH₂CF₃ |
| 804 | H | —CH₂SH | 828 | Me | —CH₂SH |

TABLE 40

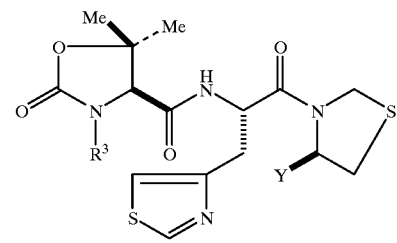

| Example No. | R³ | Y | Example No. | R³ | Y |
|---|---|---|---|---|---|
| 829 | H | Me | 853 | Me | Me |
| 830 | H | Et | 854 | Me | Et |
| 831 | H | n-Pr | 855 | Me | n-Pr |
| 832 | H | i-Pr | 856 | Me | i-Pr |
| 833 | H | c-Pr | 857 | Me | c-Pr |
| 834 | H | n-Bu | 858 | Me | n-Bu |
| 835 | H | i-Bu | 859 | Me | i-Bu |
| 836 | H | sec-Bu | 860 | Me | sec-Bu |
| 837 | H | t-Bu | 861 | Me | t-Bu |
| 838 | H | —COOH | 862 | Me | —COOH |
| 839 | H | —COOMe | 863 | Me | —COOMe |
| 840 | H | —CONH₂ | 864 | Me | —CONH₂ |
| 841 | H | —CONHMe | 865 | Me | —CONHMe |
| 842 | H | —CN | 866 | Me | —CN |
| 843 | H | —CH₂OH | 867 | Me | —CH₂OH |
| 844 | H | —CH₂OMe | 868 | Me | —CH₂OMe |
| 845 | H | —CH₂COOH | 869 | Me | —CH₂COOH |
| 846 | H | —CH₂COOMe | 870 | Me | —CH₂COOMe |

TABLE 40-continued

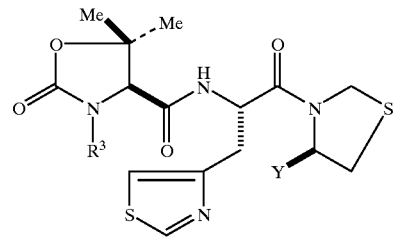

| Example No. | R³ | Y | Example No. | R³ | Y |
|---|---|---|---|---|---|
| 847 | H | —CH₂COPh | 871 | Me | —CH₂COPh |
| 848 | H | —CH₂CONH₂ | 872 | Me | —CH₂CONH₂ |
| 849 | H | —CH₂CN | 873 | Me | —CH₂CN |
| 850 | H | —CH₂CHO | 874 | Me | —CH₂CHO |
| 851 | H | —CH₂CF₃ | 875 | Me | —CH₂CF₃ |
| 852 | H | —CH₂SH | 876 | Me | —CH₂SH |

TABLE 41

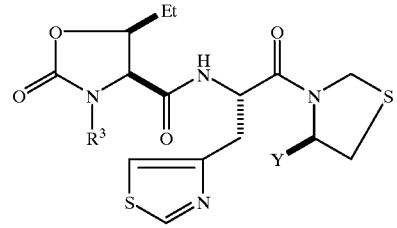

| Example No. | R³ | Y | Example No. | R³ | Y |
|---|---|---|---|---|---|
| 877 | H | Me | 901 | Me | Me |
| 878 | H | Et | 902 | Me | Et |
| 879 | H | n-Pr | 903 | Me | n-Pr |
| 880 | H | i-Pr | 904 | Me | i-Pr |
| 881 | H | c-Pr | 905 | Me | c-Pr |
| 882 | H | n-Bu | 906 | Me | n-Bu |
| 883 | H | i-Bu | 907 | Me | i-Bu |
| 884 | H | sec-Bu | 908 | Me | sec-Bu |
| 885 | H | t-Bu | 909 | Me | t-Bu |
| 886 | H | —COOH | 910 | Me | —COOH |
| 887 | H | —COOMe | 911 | Me | —COOMe |
| 888 | H | —CONH₂ | 912 | Me | —CONH₂ |
| 889 | H | —CONHMe | 913 | Me | —CONHMe |
| 890 | H | —CN | 914 | Me | —CN |
| 891 | H | —CH₂OH | 915 | Me | —CH₂OH |
| 892 | H | —CH₂OMe | 916 | Me | —CH₂OMe |
| 893 | H | —CH₂COOH | 917 | Me | —CH₂COOH |
| 894 | H | —CH₂COOMe | 918 | Me | —CH₂COOMe |
| 895 | H | —CH₂COPh | 919 | Me | —CH₂COPh |
| 896 | H | —CH₂CONH₂ | 920 | Me | —CH₂CONH₂ |
| 897 | H | —CH₂CN | 921 | Me | —CH₂CN |
| 898 | H | —CH₂CHO | 922 | Me | —CH₂CHO |
| 899 | H | —CH₂CF₃ | 923 | Me | —CH₂CF₃ |
| 900 | H | —CH₂SH | 924 | Me | —CH₂SH |

TABLE 42

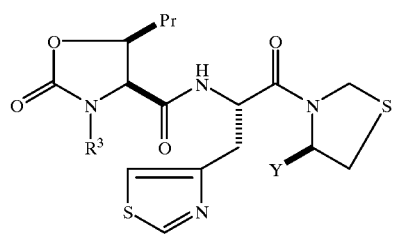

| Example No. | R³ | Y | Example No. | R³ | Y |
|---|---|---|---|---|---|
| 925 | H | Me | 949 | Me | Me |
| 926 | H | Et | 950 | Me | Et |
| 927 | H | n-Pr | 951 | Me | n-Pr |
| 928 | H | i-Pr | 952 | Me | i-Pr |
| 929 | H | c-Pr | 953 | Me | c-Pr |
| 930 | H | n-Bu | 954 | Me | n-Bu |
| 931 | H | i-Bu | 955 | Me | i-Bu |
| 932 | H | sec-Bu | 956 | Me | sec-Bu |
| 933 | H | t-Bu | 957 | Me | t-Bu |
| 934 | H | —COOH | 958 | Me | —COOH |
| 935 | H | —COOMe | 959 | Me | —COOMe |
| 936 | H | —CONH₂ | 960 | Me | —CONH₂ |
| 937 | H | —CONHMe | 961 | Me | —CONHMe |
| 938 | H | —CN | 962 | Me | —CN |
| 939 | H | —CH₂OH | 963 | Me | —CH₂OH |
| 940 | H | —CH₂OMe | 964 | Me | —CH₂OMe |
| 941 | H | —CH₂COOH | 965 | Me | —CH₂COOH |
| 942 | H | —CH₂COOMe | 966 | Me | —CH₂COOMe |
| 943 | H | —CH₂COPh | 967 | Me | —CH₂COPh |
| 944 | H | —CH₂CONH₂ | 968 | Me | —CH₂CONH₂ |
| 945 | H | —CH₂CN | 969 | Me | —CH₂CN |
| 946 | H | —CH₂CHO | 970 | Me | —CH₂CHO |
| 947 | H | —CH₂CF₃ | 971 | Me | —CH₂CF₃ |
| 948 | H | —CH₂SH | 972 | Me | —CH₂SH |

Referential Example

Preparation of cis-L-5-methyl-2-oxo-oxazolidine-4-carbonyl-L-hystidyl-L-prolineamide (52)

In a manner similar to that described in the method of Example 1–3, N-hydroxysuccinimide ester of cis-L-5-methyl-2-oxo-oxazolidine-4-carboxylic acid which was synthesized by reacting cis-L-5-methyl-2-oxo-oxazolidine-4-carboxylic acid (226 mg, 1.56 mmol), N-hydroxysuccinimide (179 mg, 1.56 mmol), and DCC (338 mg, 1.63 mmol) in N, N-dimethylformamide (5 ml) was condensed with L-hystidyl-L-prolineamide hydrobromide (870 mg, 1.56 mmol), which was synthesized in accordance with the method described in Bull. Chem. Soc. Jpn. 44, 1689 (1971), in the presence of triethylamine (0.87 ml, 6.24 mmol) to give the referential compound (42) (223 mg, 38%). The chemical formula was shown below.

$[\alpha]_D = -49.9°$ (c=0.505, MeOH, 24° C.).

NMR(CD₃OD): 7.60 (1H, s), 6.97 (1H, s), 4.90 (2H, m), 4.41 (1H, dd, J=3.3, 8.5 Hz), 4.35 (1H, d, J=8.4 Hz), 3.85 (1H, m), 3.43 (1H, m), 3.13 (1H, dd, J=6.6, 14.7 Hz), 2.98 (1H, m), 2.29 (1H, m), 2.00 (3H, m), 1.22 and 1.29 (total 3H, d, J=6.3 Hz).

Elemental analysis (C₁₆H₂₂N₆O₅ 2H₂O) Calcd.: C,46.37; H,6.32; N,20.28. Found: C,46.30; H,6.27; N,20.54.

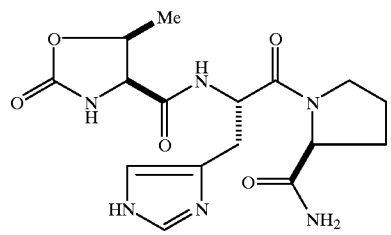

Test Example 1

Anti-recerpine Action After Oral Administration of Test Compounds

Reserpine-induced hypothemia mice (ddY, male, body weight: 30 to 40 g) were prepared by the subcutaneous administration of reserpine in back side of the rat (3 mg/kg) at 18 hours before test compounds administration. Mice with their body temperature about 25° C. were used in the experiment. Test compounds were solubilized in saline and 0.2 ml (10 μmol/kg) of them were administered by sonde for oral administration. After the administration, rectal temperature was measured at, 30, 60, 120, 180, 240, 300, and 360 min. The area under curve (AUC) of the body temperature-time profile was calculated by the general trapezoidal method. In the control experiment, vehicle (saline) was administered to mice and the rectal temperature was measured by the same protocol. The effective dose, which can increase the average of body temperature at 1° C. for 420 min in reserpine-induced hypothermia mice after oral administration of the test compounds, is calculated by the following equation:

$$\text{Effective dose} = \frac{\text{Orally administered dose}}{\text{AUC(test compounds)} - \text{AUC(vehicle)}/420}$$

Effective dose: Dose which can increase the average of body temperatures at 1° C. for 420 min in reserpine-induced hypothermia mice.

AUC (test compounds): The area under curve (AUC) of the body temperature-time profile for 420 min after oral administration of test compounds was calculated by the general trapezoidal method.

AUC (vehicle): The area under curve (AUC) of the body temperature-time profile for 420 min after oral administration of saline was calculated by the general trapezoidal method.

The results were shown in Table 43.

TABLE 43

| | Dose which can increase the average of body temperatures at 1° C. for 420 min in reserpine-induced hypothermia mice by oral) (μmol / kg) |
|---|---|
| TRH | 42.68 |
| I-4 | 0.86 |
| I-5 | 1.22 |
| I-10 | 1.14 |
| I-11 | 2.03 |
| I-30 | 2.59 |
| I-40 | 1.65 |

Test Example 2

Anti Recerpine Action After Intravenous and Intracerebroventicular Administration of Test Compounds Recerpine-induced hypothermia mice (ddY, male) were prepared by the administration of reserpine (3 mg/kg) at 18 hours before test compounds administration. Mice with their body temperature about 25° C. were used in the experiment. Test compounds were solubilized in saline and 0.1 ml (1 µmol/kg) of them were administered intravenously and 0.005 ml (0.21 µmol/kg) of them were administered intracerebroventicularly, respectively. After the administration, rectal temperature was measured at 30, 60, 120, and 180 min. The area under curve (AUC) of the body temperature-time profile was calculated by the general trapezoidal method. In the control experiment, vehicle (saline) was administered to mice intravenously or intracerebroventicularly and the rectal temperature was measured by the same protocol. The effective dose, which can increase the average of body temperatures at 1° C. for 180 min in reserpine-induced hypothermia mice after intravenous or intracerebroventicular administration of the test compounds, is calculated by the following equation:

$$\text{Effective dose} = \frac{\text{Orally administered dose}}{\text{AUC(test compounds)} - \text{AUC(vehicle)}}$$

$$\text{Effective dose} = \frac{\text{Orally administered dose}}{\text{AUC(test compounds)} - \text{AUC(vehicle)}/180}$$

Effective dose: Dose which can increase the average of body temperatures at 1° C. for 180 min in reserpine-induced hypothermia mice.

AUC (test compounds): The area under curve (AUC) of the body temperature-time profile for 180 min after intravenous or intracerebroventicular administration of test, compounds was calculated by the general trapezoidal method.

AUC (vehicle): The area under curve (AUC) of the body temperature-time profile for 180 min after intravenous or intracerebroventicular administration of saline was calculated by the general trapezoidal method.

The results were shown in Table 44.

TABLE 44

| | Dose which can increase the average of body temperatures at 1° C. for 180 min in reserpine-induced hypothermia mice (µmol / kg) | |
|---|---|---|
| | administered intracerebroventicularly | administered intravenously |
| TRH | 0.033 | 9.84 |
| I-10 | 0.025 | 0.11 |

Test Example 3
Effect on Acetylcholine Release

Male Wister rats (body weight: 250 to 300 g) which were fasted over night and anesthetized with uretane were placed in stereotaxic frame for rats. After the skin of scalp was incised and the skull was exposed, the cortex of frontal lobe was drilled (A 3.7, L 3.0, H 4.0). The dialysis probe used in the present experiment was I-shaped with a 3 mm long polycarbonate membrane tubing (CMA-12, BAS Co., LTD). Body temperature of rats were kept at 37° C. by a hot blanket. Perfusion was performed at a constant rate of 2 µl/min with Ringer's solution containing 10 µM physostigmine. Perfusate were collected every 30 min. After the perfusion for 2 hours, test compounds (24 µmol/kg) solubilized in saline were administered orally to rats and then perfusion was continued for 6 hours. The concentrations of acetylcholine in perfusate were determined by a HPLC/ECD. The acetylcholine level before the administration of test compound was defined as the average baseline level (100%). Data represent the increase of acetylcholine content of each fraction, expressed as a percentage compared to the average baseline level. The result was shown in FIG. 1.

Figure 2:
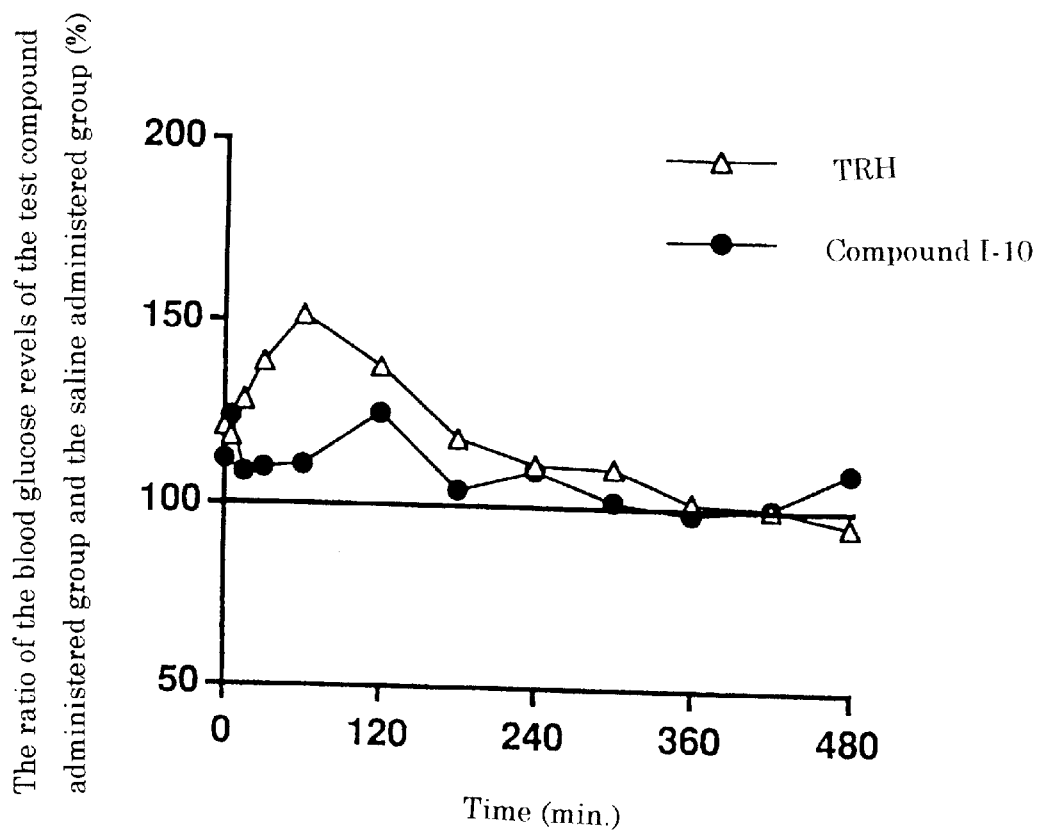
FIG. 2 shows the transition of the blood glucose level by intravenous injection to rats (the horizontal axis shows time course and the vertical axis shows the blood glucose level).

Test Example 4
The Change of Blood Glucose Levels After the Duodenal Administration of the Test Compounds to Rats Fasted male Wistar rats (250–350 g) were anesthetized with urethane. Test compounds were solubilized in saline and administered intravenously (50 µmol/kg). Body temperature of rats were kept at 37° C. by a hot blanket. After the administration, blood was collected from jugular vein at 5, 15, 30, 60, 120, 180, 240, 300, 360, 420, and 480 min and blood glucose levels were measured (BM Test blood sugar, Wako Chemical Indus.) The blood glucose levels at each sampling time in vehicle (saline)-treated rats were defined as the baseline level (100%). Data represent the changes of blood glucose levels after the duodenal administration of test compounds to rats, expressed as a percentage compared to the baseline level. The results was shown in FIG. 2. The date was shown in Table 45.

TABLE 45

| Time (min) | TRU | Compound (I-10) |
|---|---|---|
| 0 | 116.3 | 107.7 |
| 5 | 114.6 | 119.9 |
| 15 | 123.3 | 104.3 |
| 30 | 137.9 | 109.1 |
| 60 | 153.5 | 112.1 |
| 120 | 139.1 | 126.5 |
| 180 | 119.1 | 105.3 |
| 240 | 112.6 | 110.9 |
| 300 | 113.2 | 104.0 |
| 360 | 103.5 | 100.4 |
| 420 | 102.6 | 102.6 |
| 480 | 97.1 | 111.8 |

Formulation Example

Formulation Example 1

Granules are prepared using the following ingredients.

| Ingredients | |
|---|---|
| The compound represented by the formula (I) | 10 mg |
| Lactose | 700 mg |
| Corn Starch | 274 mg |
| HPC-L | 16 mg |
| | 1000 mg |

The compound represented by the formula (I) and lactose were made pass through a 60 mesh sieve. Corn starch was made pass through a 120 mesh sieve. They were mixed by a twin shell blender. An aqueous solution of HPC-L (low mucosity hydroxypropylcellulose) was added to the mixture and the resulting mixture was kneaded, granulated (by the extrusion with pore size 0.5 to 1 mm mesh), and dried. The dried granules thus obtained were sieved by a swing sieve (12/60 mesh) to yield the granules.

Formulation 2

Powders for filling capsules are prepared using the following ingredients.

| Ingredients | |
|---|---|
| The compound represented by the formula (I) | 10 mg |
| Lactose | 79 mg |
| Corn starch | 10 mg |
| Magnesium stearate | 10 mg |
| | 100 mg |

The compound represented by the formula (I) and lactose were made pass through a 60 mesh sieve. Corn starch was made pass through a 120 mesh sieve. These ingredients and magnesium stearate were mixed by a twin shell blender. 100 mg of the 10-fold trituration was filled into a No. 5 hard gelatin capsule.

Formulation 3

Granules for filling capsules are prepared using the following ingredients.

| Ingredients | |
|---|---|
| The compound represented by the formula (I) | 15 mg |
| Lactose | 90 mg |
| Corn starch | 42 mg |
| HPC-L | 3 mg |
| | 150 mg |

The compound represented by the formula (I) and lactose were made pass through a 60 mesh sieve. Corn starch was made pass through a 120 mesh sieve. After mixing them, an aqueous solution of HPC-L was added to the mixture and the resulting mixture was kneaded, granulated, and dried. After the dried granules were lubricated, 150 mg of that, were filled into a No. 4 hard gelatin capsule.

Formulation 4

Tablets are prepared using the following ingredients.

| Ingredients | |
|---|---|
| The compound represented by the formula (I) | 10 mg |
| Lactose | 90 mg |
| Microcrystal cellulose | 30 mg |
| CMC-Na | 15 mg |
| Magnesium stearate | 5 mg |
| | 150 mg |

The compound represented by the formula (I), lactose, microcrystal cellulose, and CMC-Na (carboxymethylcellulose sodium salt) were made pass through a 60 mesh sieve and then mixed. The resulting mixture was mixed with magnesium stearate to obtain the mixed powder for the tablet formulation. The mixed powder was compressed to yield tablets of 150 mg.

Formulation Example 5

Sustained release tablets are prepared using the following ingredients.

| Ingredients | |
|---|---|
| The compound represented by the formula (I) | 15 mg |
| Lactose | 20 mg |
| Microcrystal cellulose | 100 mg |
| Magnesium stearate | 5 mg |
| Lovely wax-120 H | 110 mg |
| | 250 mg |

The compound represented by the formula (I), lactose, and microcrystal cellulose were made pass through a 60 mesh sieve and were mixed. Mixpowders were heated and solubilized with lovely wax-120 H (Froint Inds.) and then granulated. Magnesium stearate previously made pass through a 60 mesh sieve was added to the obtained granules and the resulting granules were compressed to yield sustained-release tablets.

Formulation Example 6

Sustained release double layered tablet are prepared using the following ingredients.

| Ingredients | |
|---|---|
| Immediately release layer | |
| The compound represented by the formula (I) | 15 mg |
| Lactose | 25 mg |
| Microcrystal cellulose | 100 mg |
| Methylcellulose | 5 mg |
| Magnesium stearate | 5 mg |
| | 150 mg |
| Sustained layer | |
| The compound represented by the formula (I) | 15 mg |
| Lactose | 25 mg |
| Microcrystal cellulose | 90 mg |
| Stearic acid | 10 mg |
| Methylcellulose | 5 mg |
| Magnesium stearate | 5 mg |
| | 150 mg |

Immediately release layer: The compound represented by the formula (I), lactose, and microcrystal cellulose were made pass through a 60 mesh sieve and were mixed. A solution of methylcellulose was added to the mixture and the resulting mixture was kneaded, granulated and dried to yield the granules.

Sustained release layer: The compound represented by the formula (I) lactose, and microcrystal cellulose were made pass through a 60 mesh sieve and were mixed. Stearic acid was added to the mixture and the resulting mixture was heated and dissolved. They were kneaded, were granulated, and were dried to yield the granules.

Double layered tablet formation: Magnesium stearate was added to the granules of immediately release layer and the resulting mixture was compressed. Subsequently, magnesium stearate was added to the granules of immediately release layer and the resulting mixture was compressed on to yield sustained release double layered tablets.

Formulation Example 7

Enteric coated granules are prepared using the following ingredients.

| Ingredients | |
|---|---|
| The compound represented by the formula (I) | 30 mg |
| Microcrystal cellulose | 125 mg |
| Corn starch | 50 mg |
| CMC-Na | 25 mg |
| HPC or MC | 10 mg |
| | 240 mg |
| (Coating solution) | |
| HP-55 | 10.5 mg |
| Fatty acid ester of glycerin | 2.0 mg |
| Ethanol | 41.0 mg |
| Dichloromethane | 46.5 mg |
| Talc | 4 mg |

The active ingredient, microcrystal cellulose, corn starch, and CMC-Na were made pass through a 20 mesh sieve and mixed thoroughly. A solution of HPC (hydroxypropyhlcellulose) or MC (methylcellulose) was added to the mixture and the kneading was made pass through a 16 mesh sieve. The obtained granules were dried at 50 to 60° C. The dried granules were spray-coated with a solution of HP-55 (hydroxypropylmethylcellulose phthalate, Shinetsu Kagaku inc.) in fatty acid ester of glycerin, ethanol, dichloromethane, and talc to yield the enteric coated granules.

Formulation 8

Enteric coated granules are prepared using the following ingredients.

| Ingredients | |
|---|---|
| The compound represented by the formula (I) | 30 mg |
| Microcrystal cellulose | 155 mg |
| Corn starch | 60 mg |
| CMC-Na | 25 mg |
| HPC or MC | 5 mg |
| | 275 mg |
| (Coating solution) | |
| Eudragit L30D-55 | 46.8 mg |
| Polysolvate 80 | 0.7 mg |
| PEG 6000 | 1.4 mg |
| Talc | 4.2 mg |
| Purified water | 46.8 mg |

The granules which are prepared in a manner similar to that described in the method of Formulation example 7 was coated with the coating solution comprising the solution of Eudragit L30D-55 (Röhm Pharma) in polysolvate 80 (polyoxyethylenesorbitan monooleate, Kao inc.), PEG 6000, talc, and purified water. After the obtained granules were dried, the resulting granules were made pass through a 16 mesh sieve to yield the enteric coated granules.

Formulation Example 9

Sublingual tablets are prepared using the following ingredients.

| Ingredients | |
|---|---|
| The compound represented by the formula (I) | 10 mg |
| Lactose | 70 mg |
| Corn starch | 12 mg |
| Methylcellulose | 5 mg |
| Talc | 2 mg |
| Magnesium stearate | 1 mg |
| | 100 mg |

The compound represented by the formula (I), lactose, and corn starch were made pass through a 80 mesh sieve and mixed. Mixpowder was kneaded with methylcellulose solution and granulated, dried, then the granules were lubricated.

Formulation Example 10

Injections are prepared using the following ingredients.

| Ingredients | |
|---|---|
| The compound represented by the formula (I) | 1 mg |
| Glucose | 2 mg |
| Water for injection | 997 mg |
| | 1000 mg |

The above ingredients were filled into ampoules.

Formulation 11

Freeze-dried injections are prepared using the following ingredients.

| Ingredients | |
|---|---|
| The compound represented by the formula (I) | 1 mg |
| D-mannitol | 200 mg |
| Water for injection | 779 mg |
| | 1000 mg |

The above ingredients were filled into ampoules for freeze-drying and the ampoules were freeze-dried to yield the freeze-dried injections.

Formulation 12

Suppositories are prepared using the following ingredients.

| Ingredients | |
|---|---|
| The compound represented by the formula (I) | 30 mg |
| Witepsol | 1470 mg |
| | 1500 mg |

The compound represented by the formula (I) was made pass through a 60 mesh sieve. The compound was dispersed in the solution of the melted witepsol (higher fatty acid triglyceride) at 50 to 60° C. The solution was cooled to 38 to 40° C. with stirring to yield the medical fluid. The medical fluid was filled into a container of aluminum foil, sealed, and then cooled to yield the suppositories.

Formulation Example 13

Nasals are prepared using the following ingredients.

| Ingredients | |
|---|---|
| The compound represented by the formula (I) | 2 mg |
| Carboxyvinylpolymer | 5 mg |
| L-Arginine | 10 mg |
| Sodium chloride | 0.6 mg |
| Purified water | 84.2 mg |
| | 100 mg |

After the compound represented by the formula (I) was dissolved in carboxyvinylpolymer, L-arginine and sodium chloride was added to the solution. The solution's pH was adjusted and the mucosity was adjusted by adding purified water to yield the objective medical fluid.

Formation Example 14

Endermatic formulation was prepared using the following ingredients.

| Ingredients | |
|---|---|
| The compound represented by the formula (I) | 10 mg |
| Iso-propyl myristate | 990 mg |
| | 1000 mg |

After the compound represented by the formula (I) was dispersed in iso-propyl myristate, the mixture was mixed with acrylic adhesive formulation and was attached plastered to a support to yield endermatic formulation.

Formulation Example 15

Ointment was prepared using the following ingredients.

| Ingredients | |
|---|---|
| The compound represented by the formula (I) | 10 mg |
| Liquidparaffin | 7.5 mg |
| Glycerol | 82.5 mg |
| | 100 mg |

The compound represented by the formula (I) was dispersed in liquid paraffin and kneaded to yield the ointment.

Industrial Applicability

The novel peptide derivatives having 3-(4-thiazolyl or 5-thiazolyl)-alanine residue and having an effect of activating the central nervous system were provided.

What is claimed is:

1. A peptide derivative of the formula (I):

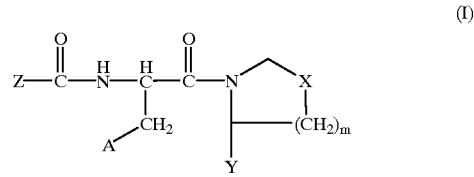

wherein

A is 4-thiazolyl or 5-thiazolyl wherein the nitrogen in the thiazolyl ring may be a quarternary nitrogen which is formed with an optionally substituted alkyl or alkenyl group, X is a bond, oxygen, or sulfur, m is an integer of 0 to 4, Y is an optionally substituted alkyl, an optionally substituted carboxy, a cyano, or a substituent represented by the formula:

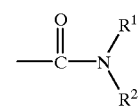

wherein $R^1$ and $R^2$ are independently a hydrogen or an optionally substituted alkyl group, or $R^1$ and $R_2$ taken together with may form a non-aromatic heterocyclic ring with the adjacent nitrogen, which may contain oxygen, nitrogen, or sulfur and may be substituted, Z is the substituent represented by the formula:

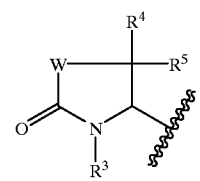

wherein $R^3$ is a hydrogen, an optionally substituted alkyl group, an optionally substituted carboxy group, or an optionally substituted acyl group, $R^4$ and $R_5$ are each independently a hydrogen or an optionally substituted alkyl group, and W is an oxygen, a sulfur, an optionally substituted imino, —(CH$_2$)n- wherein n is 0, 1, 2, or 3, or the substituent represented by the formula:

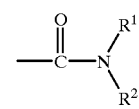

or an acceptable salt or hydrate thereof.

2. A peptide derivative of the formula (II):

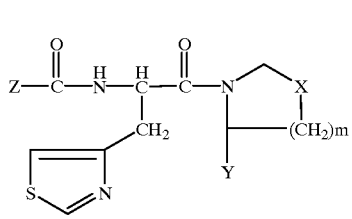

(II)

wherein X, Y, Z, and m are as defined in claim 1, and the nitrogen in the thiazolyl ring may be a quarternary nitrogen which if formed with an optionally substituted alkyl or alkenyl group, or an acceptable salt or hydrate thereof.

3. A peptide derivative of the formula (III):

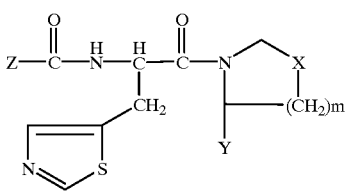

(III)

wherein X, Y, Z, and m are as defined in claim 1, and the nitrogen in the thiazolyl ring may be a quarternary nitrogen which is formed with an optionally substituted alkyl or alkenyl group, or an acceptable salt, or hydrate thereof.

4. A peptide derivative of the formula (IV):

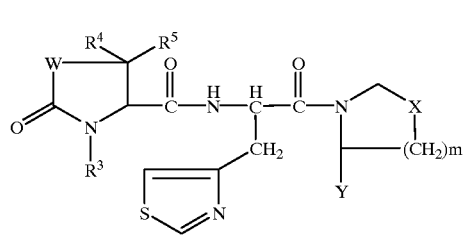

(IV)

wherein W, X, Y, m $R^3$, $R^4$, and $R^5$ are as defined in claim 1, an or hydrate thereof.

5. A peptide derivative of any one of claims 1 to 4 wherein m is 1 or 2, provided that X is not a bond when m is 1, or an acceptable salt or hydrate thereof.

6. A peptide derivative of any one of claims 1 to 4 wherein m is 1 and Y is an optionally substituted alkyl, an optionally substituted carboxy, or an optionally substituted carbamoyl, or an acceptable salt or hydrate thereof.

7. A peptide derivative of any one of claims 1 to 4 wherein m is 2 or 3 and Y is an optionally substituted alkyl, an optionally substituted carboxy, or an optionally substituted carbamoyl, or an acceptable salt or hydrate thereof.

8. A peptide derivative of the formula (V):

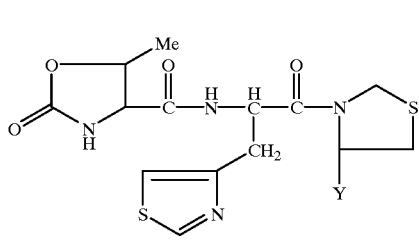

(V)

wherein Y is as defined in claim 1, an or hydrate thereof.

9. A peptide derivative of the formula (VI):

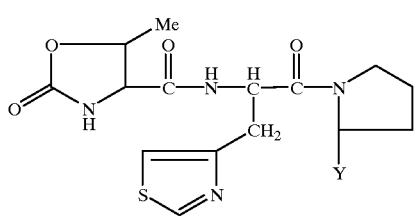

(VI)

wherein Y is as defined in claim 1, an or hydrate thereof.

10. A compound represented by the formula (VII):

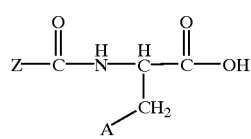

(VII)

wherein A and Z are as defined in claim 1.

11. A compound represented by the formula (VIII):

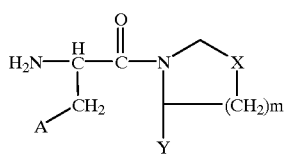

(VIII)

wherein A, X, Y, and m are as defined in claim 1.

12. A composition comprising the peptide derivative of claim 1 as an active ingredient and a suitable carrier.

13. The composition according to claim 12, wherein the active ingredient is present in an amount effective to stimulate release of acetylcholine in the cerebral cortex of a mammal.

14. The composition according to claim 12, wherein the active ingredient is present in an amount effective to antagonize the hypothermic effect of reserpine in a mammal.

* * * * *